(12) United States Patent
Kieffer et al.

(10) Patent No.: US 10,772,917 B2
(45) Date of Patent: Sep. 15, 2020

(54) PANCREATIC ENDOCRINE PROGENITOR CELL THERAPIES FOR THE TREATMENT OF OBESITY AND TYPE 2 DIABETES (T2D)

(71) Applicant: THE UNIVERSITY OF BRITISH COLUMBIA, Vancouver, British Columbia (CA)

(72) Inventors: Timothy J. Kieffer, Vancouver (CA); Jennifer E. Bruin, Vancouver (CA)

(73) Assignee: CCS VENTURES LIMITED, Vancouver, B.C. (CA)

( * ) Notice: Subject to any disclaimer, the term of this patent is extended or adjusted under 35 U.S.C. 154(b) by 16 days.

(21) Appl. No.: 15/556,907

(22) PCT Filed: Mar. 11, 2016

(86) PCT No.: PCT/CA2016/000072
§ 371 (c)(1),
(2) Date: Sep. 8, 2017

(87) PCT Pub. No.: WO2016/141460
PCT Pub. Date: Sep. 15, 2016

(65) Prior Publication Data
US 2018/0055890 A1 Mar. 1, 2018

Related U.S. Application Data

(60) Provisional application No. 62/131,540, filed on Mar. 11, 2015.

(51) Int. Cl.
| | | |
|---|---|---|
| *A61K 35/39* | (2015.01) | |
| *A61K 31/155* | (2006.01) | |
| *A61K 31/4439* | (2006.01) | |
| *A61K 31/4985* | (2006.01) | |
| *A61K 45/06* | (2006.01) | |
| *C12N 5/071* | (2010.01) | |

(52) U.S. Cl.
CPC ............ *A61K 35/39* (2013.01); *A61K 31/155* (2013.01); *A61K 31/4439* (2013.01); *A61K 31/4985* (2013.01); *A61K 45/06* (2013.01); *C12N 5/0677* (2013.01)

(58) Field of Classification Search
None
See application file for complete search history.

(56) References Cited

U.S. PATENT DOCUMENTS

| | | |
|---|---|---|
| 5,843,780 A | 12/1998 | Thomson |
| 7,510,873 B2 | 3/2009 | Mistry et al. |
| 2005/0058631 A1 | 3/2005 | Kihm et al. |
| 2007/0122903 A1 | 5/2007 | Rezania et al. |
| 2008/0113026 A1 * | 5/2008 | McKinney ............ A61K 9/209 424/472 |
| 2009/0170198 A1 | 7/2009 | Rezania |
| 2009/0280096 A1 * | 11/2009 | Kubo ................. C07K 14/4705 424/93.7 |
| 2011/0104805 A1 | 5/2011 | Fung et al. |
| 2012/0039955 A1 | 2/2012 | Xu |

FOREIGN PATENT DOCUMENTS

| | | | | |
|---|---|---|---|---|
| WO | WO-2004023100 A2 * | 3/2004 | ........... | C12N 5/0678 |
| WO | WO-2008054716 A2 * | 5/2008 | ........... | C12N 5/0678 |
| WO | WO 2014160413 | 10/2014 | | |

OTHER PUBLICATIONS

Boden et al (Euro. J. Clin. Invest., 32(3):14-23 (2002) (Year: 2002).*
Bouwens et al., Physiol. Rev., 85:1255-1270 (2005) (Year: 2005).*
Noguchi, Rev. Diabet. Stud., 7(2): 105-111 (2010) (Year: 2010).*
Meneghini et al., AJM, 126:S28-S37 (2013) (Year: 2013).*
Swinnen et al., Diab. Care, 32(2):S253-S259 (2009) (Year: 2009).*
Carver et al., The Diab. Educat., 32(6):910-917 (2006) (Year: 2006).*
Agulnick, A.D. et al. "Insulin-Producing Endocrine Cells Differentiated In Vitro From Human Embryonic Stem Cells Function in Macroencapsulation Devices In Vivo" Stem Cells Trans Med (2015) 2015 4(10):1214-1222.
Bruin, JE, et al. (2013) "Maturation and function of human embryonic stem cell-derived pancreatic progenitors in macroencapsulation devices following transplant into mice"; *Diabetologia* 56(9); pp. 1987-1998.
Bruin, JE., et al. (2014) "Characterization of poly hormonal insulin-producing cells derived in vitro from human embryonic stem cells"; *Stem Cell Res.* 12(1); pp. 194-208.
Bruin et al. (2015) "Treating diet-induced diabetes and obesity with human embryonic stem cell-derived pancreatic progenitor cells and antidiabetic drugs"; *Stem Cell Reports* 4(4); pp. 605-620.
D'Amour, K.A. et al. (2005) "Efficient differentiation of human embryonic stem cells to definitive endoderm"; *Nature Biotechnology 23*; pp. 1534-1541.
D'Amour, KA. et al. (2006) "Production of pancreatic hormone-expressing endocrine cells from human embryonic stem cells"; *Nature Biotechnology* 24(11); pp. 1392-1401; Epub Oct. 19, 2006.
Gafni, O. et al. (2013) "Derivation of novel human ground state naive pluripotent stem cells"; *Nature 504*: pp. 282-286.
Halban; "Cell therapy for type 2 diabetes: is it desirable and can we get it?"; *Diabetes, Obesity and Metabolism*, vol. 10 (Suppl4), Nov. 1, 2008; pp. 205-211.
Heit, JJ. et al. (2006) "Calcineurin/NFAT signalling regulates pancreatic β-cell growth and function" *Nature 443*(7109): 345-349.

(Continued)

*Primary Examiner* — Thomas J. Visone
(74) *Attorney, Agent, or Firm* — Bozicevic, Field & Francis LLP; Shweta Chandra

(57) ABSTRACT

Provided herein are therapies, and methods using that therapy, in the treatment of one or more of Type 2 diabetes (T2D), obesity, glucose intolerance and insulin resistance or to control weight gain in subjects. In particular, the subject may be candidates for treatment with one or more small molecule anti-diabetic drugs and the therapy may include implanting a population of pancreatic endocrine progenitor cells into the subject, where the cells are allowed to mature in vivo to produce a population.

18 Claims, 36 Drawing Sheets

(56) References Cited

OTHER PUBLICATIONS

Kahraman, S. et al. (2014) "Maternal insulin resistance and transient hyperglycemia impact the metabolic and endocrine phenotypes of offspring"; *Am J Physiol Endocrinol Metab. 307*(10): E906.

Jonas, JC. etal. (1999) "Chronic hyperglycemia triggers loss of pancreatic beta cell differentiation in an animal model of diabetes"; *J Biol Chem. 274*(20):14112-21.

Kelly, OG. et al. (2011) "Cell-surface markers for the isolation of pancreatic cell types derived from human embryonic stem cells"; *Nature Biotechnology 29*(8):pp. 750-756.

Kramer,et al (2013) "Short-term intensive insulin therapy in type 2 diabetes mellitus: a systematic review and meta-analysis"; *Lancet Diabetes Endocrinol. 1*(1); pp. 28-34.

Kroon, E. et al. (2008) "Pancreatic endoderm derived from human embryonic stem cells generates glucose-responsive insulin-secreting cells in vivo"; *Nature Biotechnology 26*; pp. 443-452.

Lee, SH. et al. (2009) "Human β-cell Precursors Mature Into Functional Insulin-producing Cells in an Immunoisolation Device: Implications for Diabetes Cell Therapies"; *Transplantation 87*(7); pp. 983-991.

Li, W. et al. (2009) "Generation of rat and human induced pluripotent stem cells by combining genetic reprogramming and chemical inhibitors"; *Cell Stem Cell 4*(1); pp. 16-19.

Loh, YH. et al. (2011) Genomic approaches to deconstruct pluripotency; *Annu Rev Genomics Hum Genet 12*; pp. 165-185.

Maherali, N. et al. (2007) "Directly reprogrammed fibroblasts show global epigenetic remodeling and widespread tissue contribution"; *Cell Stem Cell 1*(1); pp. 55-70.

Nakagawa, M.et al. (2008) "Generation of induced pluripotent stem cells without Myc from mouse and human fibroblasts"; *Nature Biotechnol 26*(1); pp. 101-106.

Ng, M. et al. (2014) "Global, Regional & National Prevalence of Overweight and Obesity in Children and Adults During 1980-2013: A Systematic Analysis for the Global Burden of Disease Study 2013"; *Lancet 384*(9945); pp. 766-781.

Nir, T., et al (2007) "Recovery from diabetes in mice by beta cell regeneration"; *J. Clin Invest 117*(9); pp. 2553-2561.

O'Dowd, JF. and Stocker, CJ. (2013) "Endocrine pancreatic development: impact of obesity and diet"; *Front Physiol. 4*; pp. 170.

Pagliuca, et al. (2014) "Generation of functional human pancreatic cells in vitro"; *Cell 159*(2); pp. 428-439.

Pepper, AR. et al. "A prevascularized subcutaneous device-less site for islet and cellular transplantation" Nature Biotechnology (2015) 33(s):s18-523.

Rezania, A.. et al. (2011) "Production of functional glucagon-secreting α-cells from human embryonic stem cells"; *Diabetes 60*(1); pp. 239-247.

Rezania, A. et al. (2012) "Maturation of human embryonic stem cell-derived pancreatic progenitors into functional islets capable of treating pre-existing diabetes in mice"; *Diabetes 61*(8); pp. 2016-2029.

Rezania, A. et al. (2013) "Enrichment of human embryonic stem cell-derived NKX6.1-expressing pancreatic progenitor cells accelerates the maturation of insulin-secreting cells in vivo"; *Stem Cells 31*(11); pp. 2432-2442.

Rezania et al.; (2014) "Reversal of diabetes with insulin-producing cells derived in vitro from human pluripotent stem cells"; *Nat Biotechnol. 32*(11); pp. 1121-1133; Epub Sep. 11, 2014.

Russ HA, et al. (2015) "Controlled induction of human pancreatic progenitors produces functional beta-like cells in vitro"; *EMBO J. 34*(13); pp. 1759-1772.

Schulz, T. etal. (2012) "A Scalable System for Production of Functional Pancreatic Progenitors from Human Embryonic Stem Cells" *PLoS One 7*(5):e37004.

Stadtfeld, M. et al. (2008) "Defining molecular cornerstones during :fibroblast to iPS cell reprogramming in mouse"; *Cell Stem Cell 2*(3); pp. 230-240.

Stein et al., "A review of the efficacy and safety of oral antidiabetic drugs", Expert Opinion on Drug Safety, Mar. 10, 2013 (Mar. 1, 2013) vol. 12, No. 2, pp. 153-175, ISSN 1474-0338.

Szot, GL. et al. (2015) "Tolerance induction and reversal of diabetes in mice transplanted with human embryonic stem cell-derived pancreatic endoderm"; *Cell Stem Cell16*(2); pp. 148-157.

Takahashi, K. et al. (2007) "Induction of pluripotent stem cells from adult human fibroblasts by defined factors"; *Cell 131*; pp. 861-872.

Takahashi, K. and Yamanaka, S. (2006) "Induction of pluripotent stem cells from mouse embryonic and adult fibroblast cultures by defined factors"; *Cell 126*(4); pp. 663-676.

Tang, Q. and Desai, TA. (2016) "Approaching a cure for type 1 diabetes"; *Nature Medicine 22*(3); pp. 236-237.

Thomson, JA, et al. (1995) "Isolation of a primate embryonic stem cell line"; *Proc Natl Acad Sci U.S.A. 92*(17); pp. 7844-7848.

Thomson, JA. and Marshall, VS. (1998) "Primate embryonic stem cells"; *Curr Top Dev Biol 38*; pp. 133-165.

Thomson, JA, et al. (1998) "Embzyonic stem cell lines derived from human blastocysts"; *Science 282*(5391); pp. 1145-1147.

Vegas, AJ, et al. (2016) "Long term Glycemic Control Using Polymer Encapsulated, Human Stem-Cell Derived β-cells in Immune Competent mice"; *Nature Medicine 22*(3); pp. 306-311.

Ware, CB, et al. (2014) "Derivation of naive human embryonic stem cells"; *Proc Natl Acad Sci USA. 111*; pp. 4484-4489.

Weng, et al. (2008) "Effect of intensive insulin therapy on beta-cell function and glycaemic control in patients with newly diagnosed type 2 diabetes: a multicentre randomised parallel-group trial"; *Lancet 371*(9626); pp. 1753-1760.

Hua Xiu-Feng, et al (2014) "Pancreatic insulin-producing cells differentiated from human embryonic stem cells correct hyperglycemia in SCID/NOD mice, an animal model of diabetes"; PLoS One 9(7); pp. e102198.

Liang, J., et al (2012) "Combined treatment with a dipeptidyl peptidase-IV inhibitor (sitagliptin) and an angiotensin II type 1 receptor blocker (losartan) promotes islet regeneration via enhanced differentiation of pancreatic progenitor cells"; Diabetes Obes Metab. 14(9); pp. 842-851.

Liang, D., et al (2015) "Embryonic stem cell-derived pancreatic endoderm transplant with MCT1-suppressing miR-495 attenuates type II diabetes in mice"; Endocr J. 62(10); pp. 907-920.

Dankner, Rachel, et. Al., (2009) "Basal-State Hyperinsulinemia in Healthy Normoglycemic Adults Is Predictive of Type 2 Diabetes Over a 24-Year Follow-Up", Diabetes Care, 32(8):1464-1466.

Gregory, Justin, et. al., (2019) "Iatrogenic Hyperinsulinemia, Not Hyperglycemia, Drives Insulin Resistance in Type 1 Diabetes as Revealed by Comparison With GCK-MODY (MODY2)", Diabetes, 68:1565-1576.

Herold, Kevan C., et. al., (2019) "An Anti-CD3 Antibody, Teplizumab, in Relatives at Risk for Type 1 Diabetes", The New England Journal of Medicine, 381(7):603-613.

Kahn, Barbara B. and Flier, Jeffrey S., (2000) "Obesity and insulin resistance", The Journal of Clinical Investigation, 106(4):473-481.

Kieffer, Timothy J. and Habener, Joel Francis, (1999) "The Glucagon-Like Peptides", Endocrine Reviews, 20(6):876-913.

Kieffer, Timothy J., et. al., (1995) "Degradation of Glucose-Dependent Insulinotropic Polypeptide and Truncated Glucagon-Like Peptide 1 in Vitro and in Vivo by Dipeptidyl Peptidase IV*", Endocrinology, 136(8):3585-3596.

Kobayashi, Masashi and Olefsky, Jerrold M., (1978) "Effect of experimental hyperinsulinemia on insulin binding and glucose transport in isolated rat adipocytes", The American Physiological Society, E53-E62.

Mehran, Arya E., et. al., (2012) "Hyperinsulinemia Drives Diet-Induced Obesity Independently of Brain Insulin Production", Cell Metabolism, 16:723-737.

Okamoto, Maristela Mitiko, et. al., (2011) "Intensive insulin treatment induces insulin resistance in diabetic rats by impairing glucose metabolism-related mechanisms in muscle and liver", Journal of Endocrinology, 211:55-64.

Poires, Walter J. and Dohm, G. Lynis, (2012) "Diabetes: Have We Got It All Wrong? Hyperinsulinism as the culprit: surgery provides the evidence", Diabetes Care, 35(12):2438-2442.

(56) References Cited

OTHER PUBLICATIONS

Roberts, Christian K. and Barnard, James R., (2005) "Effects of exercise and diet on chronic disease", J Appl Physiol, 98:3-30.

Templeman, Nicole M., et. al., (2015) "Suppression of hyperinsulinaemia in growing female mice provides long-term protection against obesity", Diabetologia, 58:2392-2402.

Alemezadeh et al., (1999) "Effect of Diazoxide on Brain Capillary Insulin Receptor Binding and Food Intake in Hyperphagic Obese Zucker Rats*", Endocrinology, 140(7): 3197-3202.

Birkeland et al., (1994) "A long-term, randomized, comparative study of insulin versus sulfonylurea therapy in type 2 diabetes", Journal of Internal Medicine, 236: 305-31.

Bruin et al., (2015) "Treating diet-induced diabetes and obesity with human embryonic stem cell-derived pancreatic progenitor cells and antidiabetic drugs", Stem Cell Reports, 4(4): 605-620.

Groop et al., (1989) "Different effects of insulin oral antidiabetic agents on glucose and energy metabolism in Type 2 (non-insulin-dependent) diabetes mellitus", Diabetologia, 32: 599-605.

Harper et al., (2013) "Pharmacologic Management of Type 2 Diabetes", Canadian Journal of Diabetes, 37: S61-S68.

Lipscombe et al., (2018) "Pharmacologic Glycemic Management of Type 2 Diabetes in Adults", Canadian Journal of Diabetes, 42: S88-S103.

Skyler, (1997) "Insulin therapy in type II diabetes", Postgraduate Medicine, 101(2): 89-96.

"Standards of Medical Care in Diabetes—2019 Abridged for Primary Care Providers", American Diabetes Association, (2019), 37(1): 11-34.

Wildman et al., (2008) "The Obese Without Cardiometabolic Risk Factor Clustering and the Normal Weight With Cardiometabolic Risk Factor Clustering", Arch Intern Med, 168(15): 1617-1624.

Yki-Jarvinen et al., (1998) "Clinical Benefits and Mechanisms of a Sustained Response to Intermittent Insulin Therapy in Type 2 Diabetic Patients with Secondary Drug Failure", The American Journal of Medicine, 84(2): 1-9.

McFarlane, S. I., "Insulin Therapy and Type 2 Diabetes: Management of Weight Gain", The Journal of Clinical Hypertension, (2009) 11(10):601-607.

Shanik M. H. et al., "Insulin Resistance and Hyperinsulinemia", Diabetes Care, (2008) 31(supplement 2):S262-S268.

Bruin J. E. et al., "Treating Diet-Induced Diabetes and Obesity with Human Embryonic Stem Cell-Derived Pancreatic Progenitor Cells and Antidiabetic Drugs", Stem Cell Reports, (2015) 4:605-620.

* cited by examiner

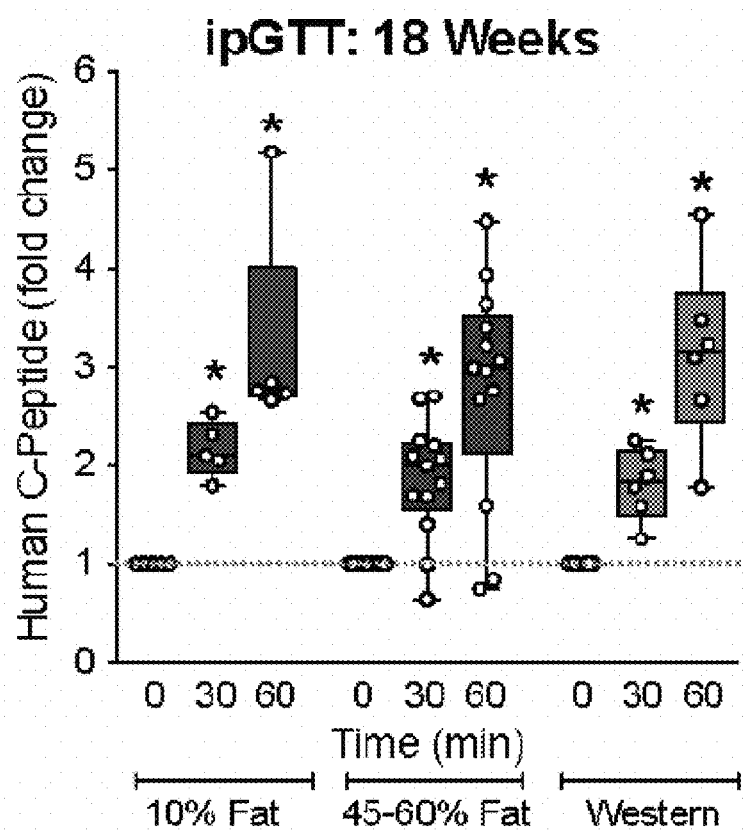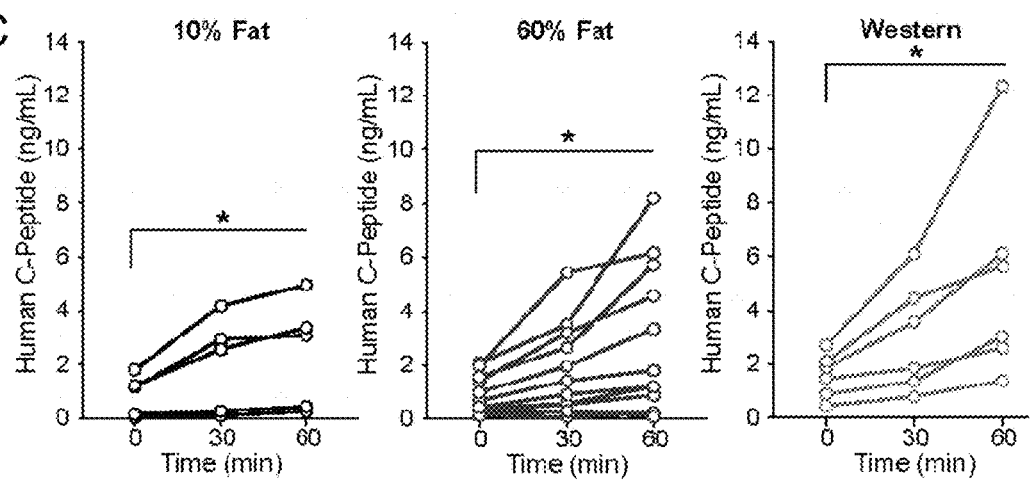

FIG. 3
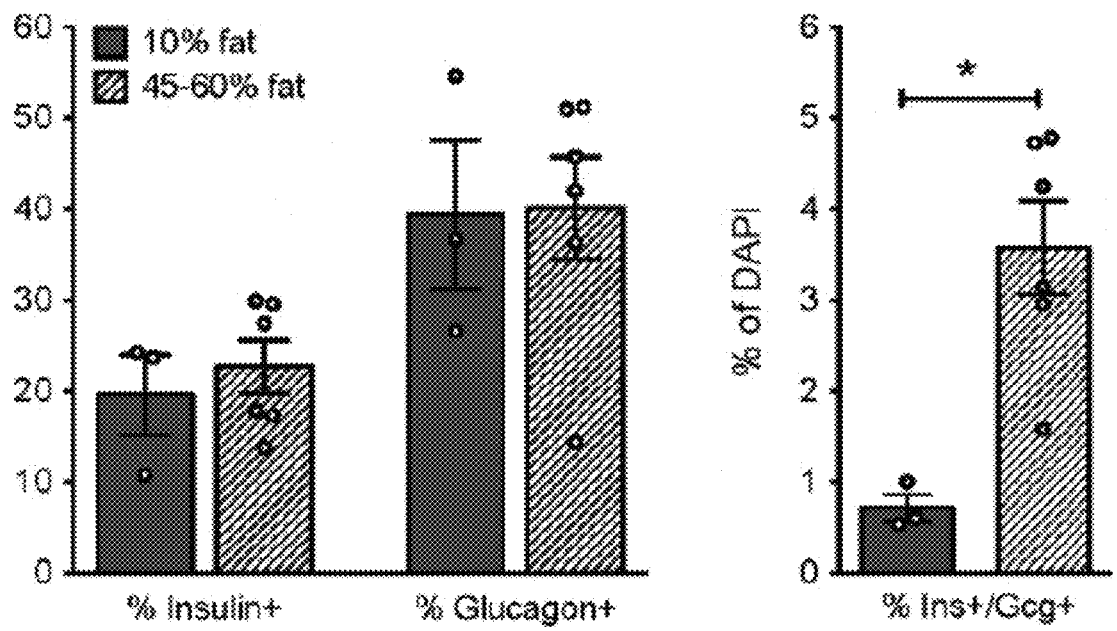
FIG. 4A HbA1C: 12 weeks
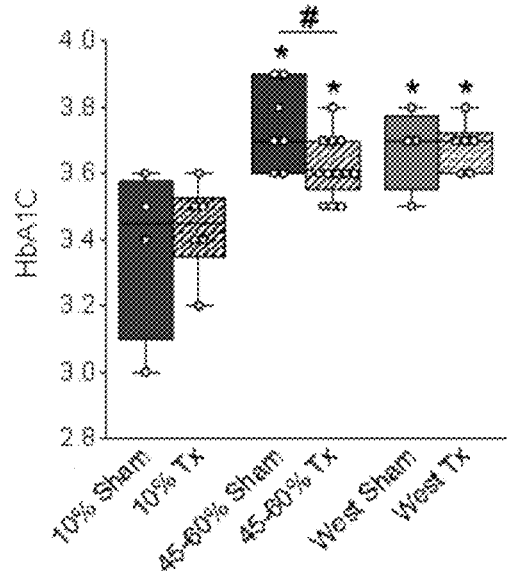
FIG. 4B HbA1C: 24 weeks
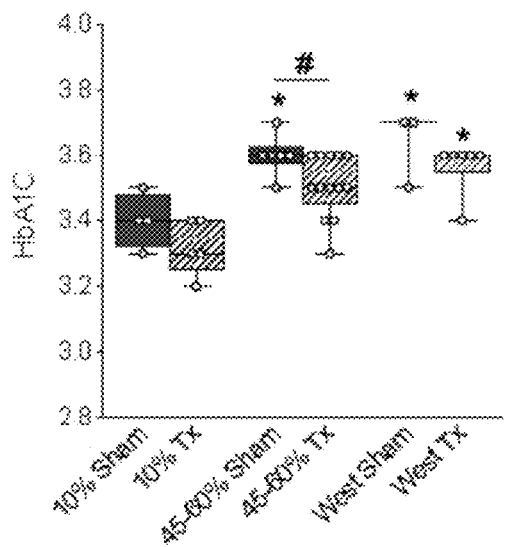

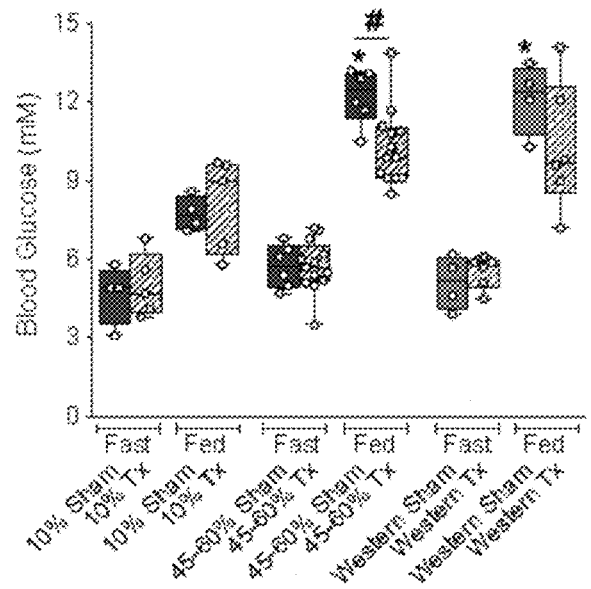
FIG. 4C  Oral Meal Challenge: 20 weeks
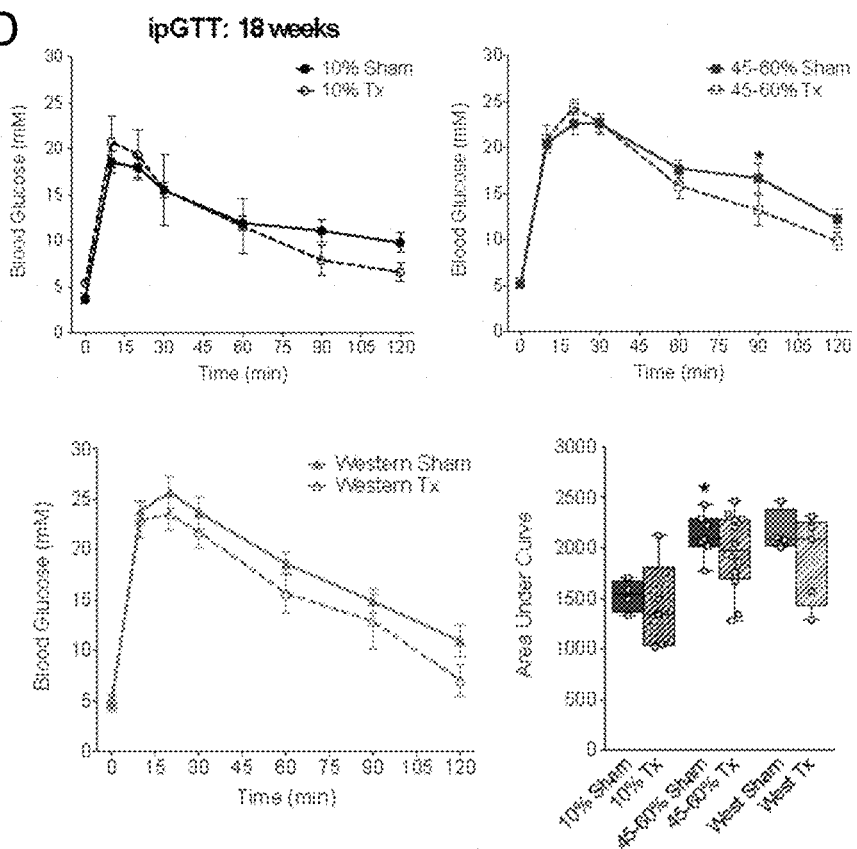
FIG. 4D  ipGTT: 18 weeks

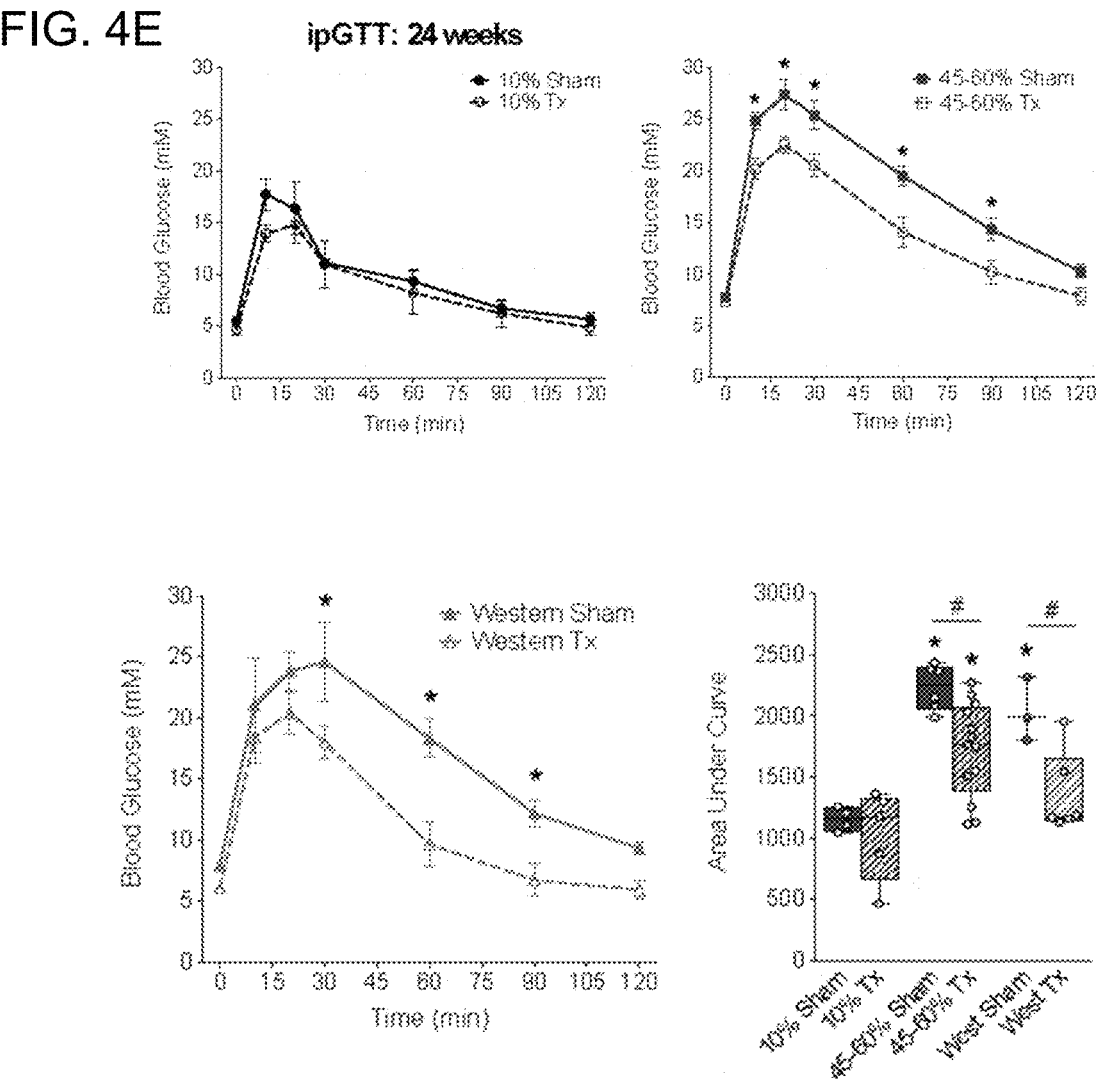

FIG. 4F
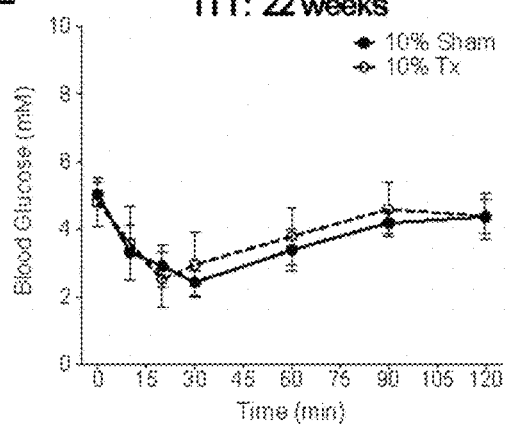
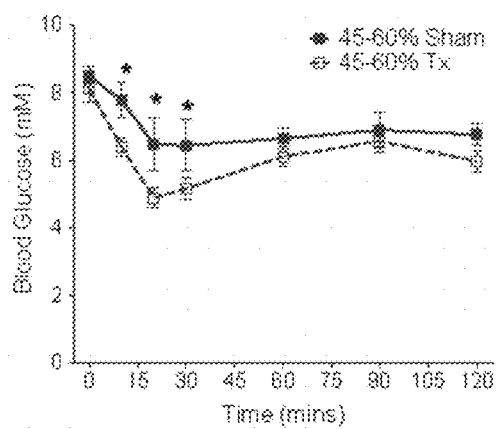
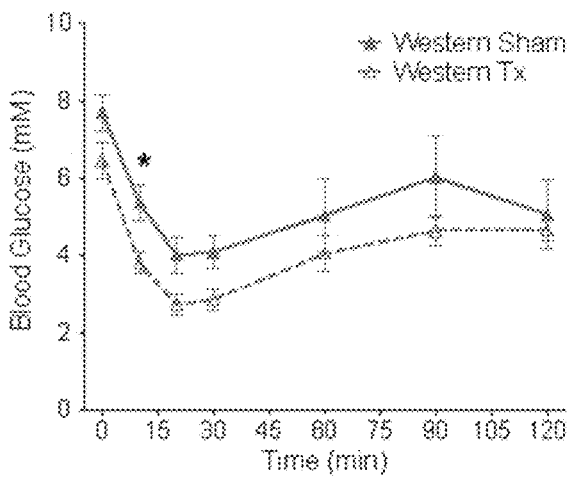
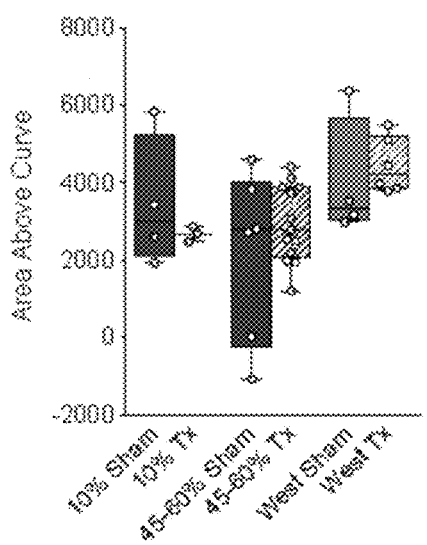

FIG. 6A 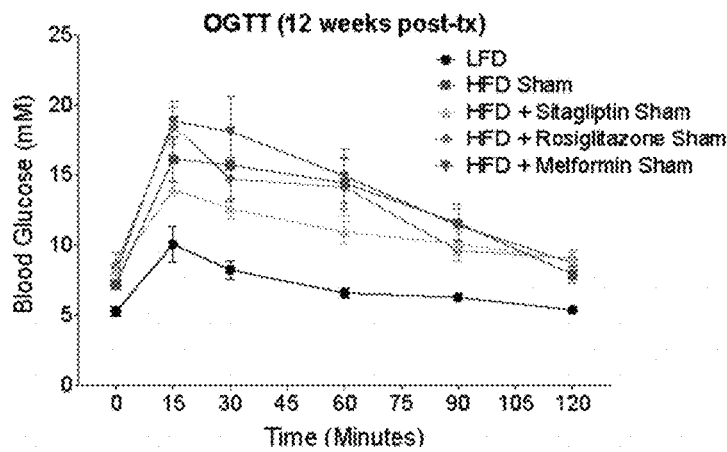 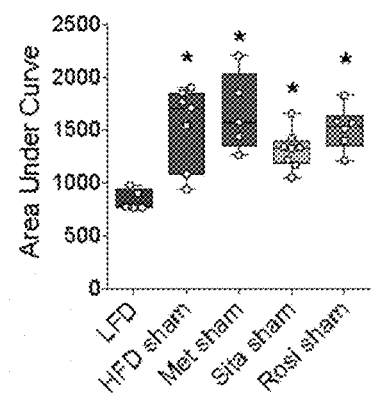
FIG. 6B 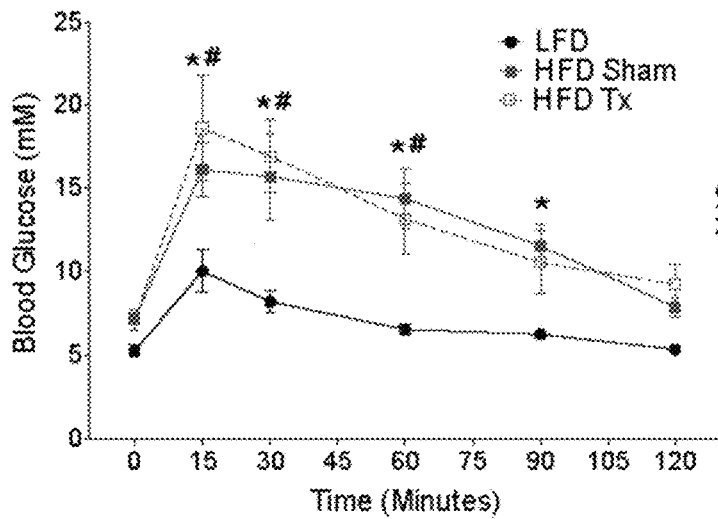 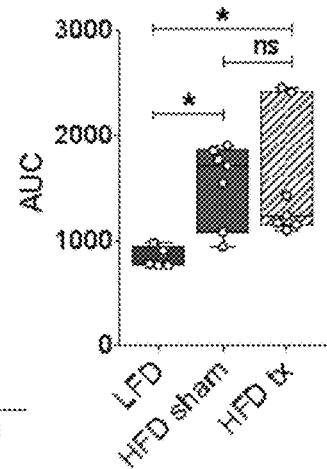

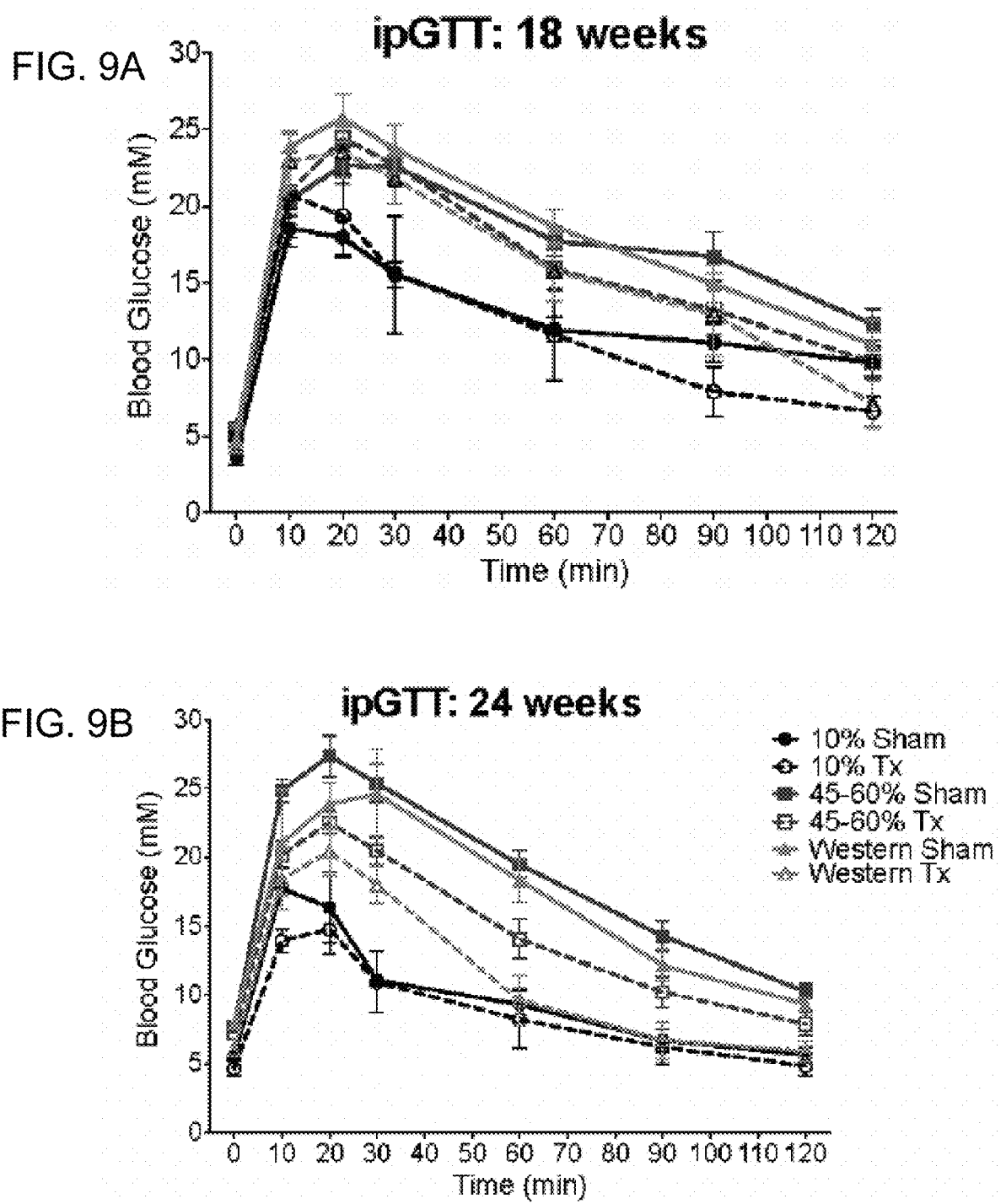

FIG. 11A  Tracking prior to LFD/HFD administration
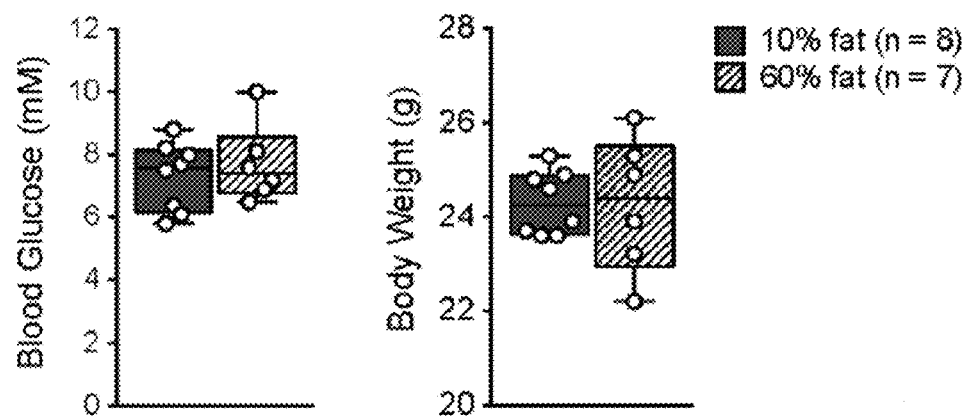
FIG. 11B
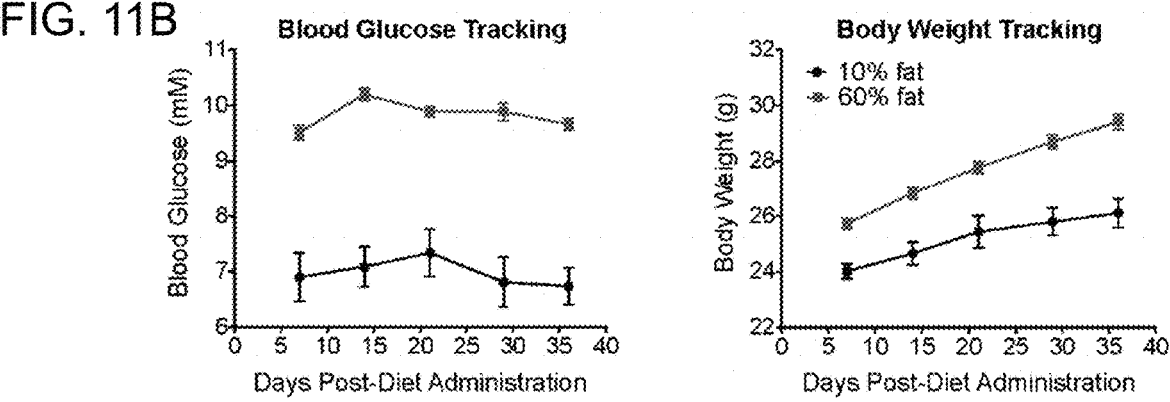

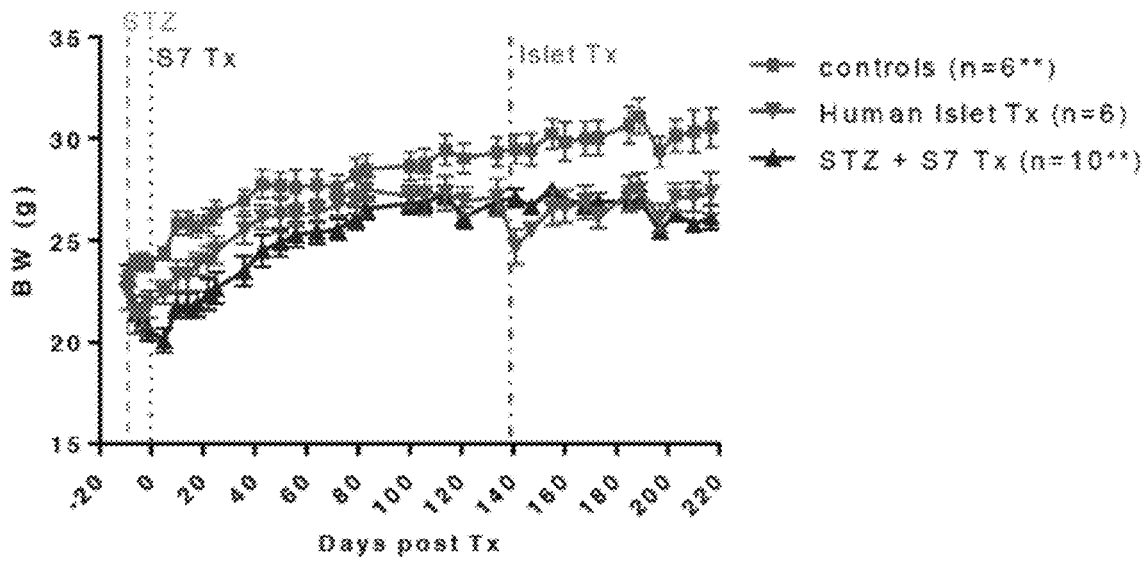
FIG. 14A  S49 - Body weight
(mean, SEM, w.o. C-pept. neg.)
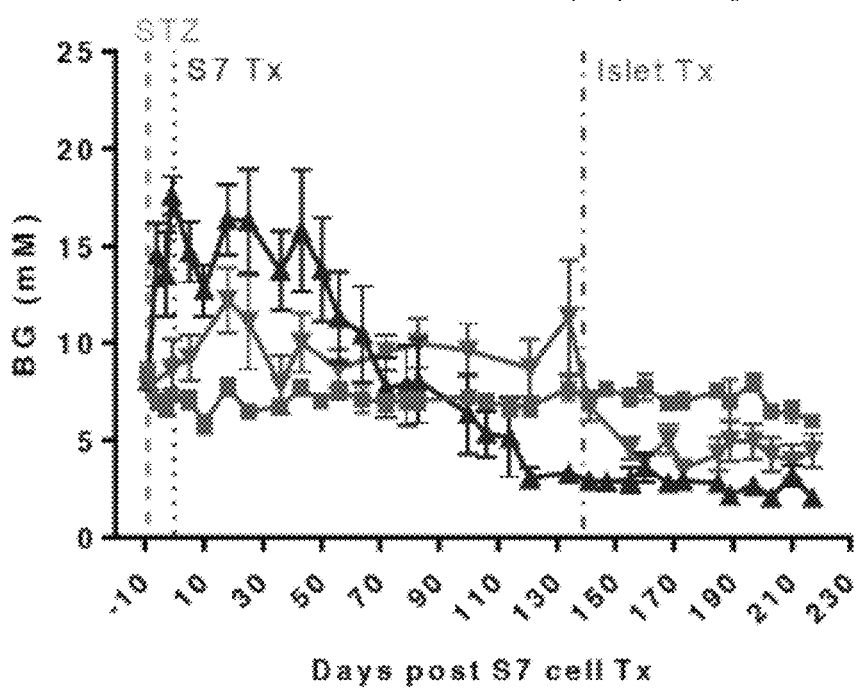
FIG. 14B  S49 - 4h fasting Blood Glucose
(mean SEM, w.o. C-pept. neg.)

PANCREATIC ENDOCRINE PROGENITOR CELL THERAPIES FOR THE TREATMENT OF OBESITY AND TYPE 2 DIABETES (T2D)

CROSS REFERENCE TO RELATED APPLICATIONS

This application is a 35 U.S.C. § 371 national stage entry of International Application No. PCT/CA2016/000072, filed 11 Mar. 2016, which application claims the benefit of U.S. Provisional Patent Application Ser. No. 62/131,540 filed on 11 Mar. 2015, entitled "THERAPY FOR THE TREATMENT OF OBESITY", which applications are incorporated herein by reference in their entireties.

TECHNICAL FIELD

The present invention relates to methods for treating metabolic disorders, medical conditions and associated pathological conditions in subjects. In particular, the invention relates to the use of cells resulting from the differentiation of pluripotent stem cells, alone or in combination with anti-diabetic medications, to achieve weight loss, improvements in glucose tolerance and/ or enhanced insulin sensitivity in subjects.

BACKGROUND

Obesity is quickly becoming a global epidemic, which epidemic crosses all age and socio-economic groups. The number of overweight and obese people worldwide has risen from 857 million in 1980 to 2.1 billion in 2013 (Ng, et al., *Global, Regional & National Prevalence of Overweight and Obesity in Children and Adults During* 1980-2013: *A Systematic Analysis for the Global Burden of Disease Study*, Lancet (2014)). Additionally, obesity is known to be a major risk factor for the development of a number of diseases including Type 2 Diabetes or Type 2 diabetes mellitus (T2D).

The International Diabetes Federation estimates that approximately 380 million people worldwide have diabetes, up to 95% of which suffer from T2D. In T2D, the body fails to properly use insulin, or is insulin resistant. T2D is also generally characterized by hyperglycemia, insulin resistance and low insulin levels. T2D is thought to be primarily due to obesity and lack of exercise in people who are genetically predisposed.

Diet, exercise and weight control are the cornerstones of managing T2D. However, drug therapy may be required in which one or more drugs are used to control blood sugar levels. Current medications for treatment of T2D are oral medications including meglitinides, sulfonylureas, dipeptidyl-peptidase 4 ("DPP-4") inhibitors, biguanides, thiazolidinediones, alpha-glucosidase inhibitors, and sodium-glucose transporter 2 ("SGLT2") inhibitors. Additionally, injectable medications, such as amylin mimetics and incretin mimetics are used to treat T2D.

A second type of diabetes mellitus, Type 1 (T1D), is a chronic condition in which little or no insulin is produced by the pancreas. Historically, T1D was treated with insulin administration in addition to the control of diet, exercise and weight. However, more recently treatment has included the transplantation of islets of Langerhans, which treatment suffers from a shortage of transplantable islets of Langerhans. Thus, even more recently, treatment development focused on developing sources of insulin-producing cells appropriate for engraftment. One such approach is the generation of insulin-producing cells from pluripotent stem cells, such as embryonic stem cells.

The production of enriched cultures of human embryonic stem cell-derived definitive endoderm and the further differentiation of such cells into pancreatic endocrine precursor cells is known (for example, US2009/0170198; Rezania, A. et al. Diabetes 2012; Rezania, A. et al. Stem Cells 2013; Bruin, J. E. et al. 2013; Bruin, J. E. et al. Stem Cell Research 2014). Published patent application, US2012/0039955, also describes a decrease in blood sugar in SCID mice with streptozotocin (STZ) induced T1D like state following transplantation of a population of encapsulated pancreatic endocrine precursor cells. It is also known that subsequent transplant of the pancreatic endocrine precursor cells into a body allows for still further differentiation into functional pancreatic endocrine cells.

SUMMARY

The present invention is based, in part, on the surprising discovery that a combination therapy of pancreatic endocrine precursor cells (Stage 4 cells) and a small molecule anti-diabetic drug was more effective in high-fat diet (HFD) fed mice than either small molecule anti-diabetic drugs or progenitor cell transplants alone. Moreover, surprisingly neither HFDs nor anti-diabetic drugs impacted the ability of human embryonic stem cell (hESC)-derived cells to mature in vivo and appropriately secrete insulin in response to glucose. The environment in which a stem cell matures is critical to the differentiated cells that result from the maturation process. Embodiments of the invention are further based on the discovery that pancreatic endocrine precursor cells may find particular utility as a therapeutic for treatment of Type 2 diabetes (T2D) in a subject, wherein the subject is a candidate for treatment with one or more small molecule anti-diabetic drugs. Embodiments of the invention are further based on the fortuitous finding that treatment with a combination of pancreatic endocrine precursor cells and a small molecule anti-diabetic drug is useful in the treatment of T2D, obesity, glucose intolerance and/or insulin resistance. Alternatively, the methods described herein may be used to improve glycemic control. Additional embodiments of the invention are further based on the fortuitous finding that the transplantation of pancreatic endocrine precursor cells alone produce weight loss in a subject. Furthermore, the weight loss was also achieved by transplanting more differentiated cells (i.e. Stage 5, Stage 6 or Stage 7 cells).

In a first embodiment, there is provided a method for treating Type 2 diabetes (T2D) in a subject, the method including: (a) implanting a population of pancreatic endocrine progenitor cells into the subject; and (b) maturing in vivo the population of pancreatic endocrine progenitor cells to produce a population including pancreatic endocrine cells.

In a further embodiment, there is provided a method for treating Type 2 diabetes (T2D) in a subject, the method including: implanting a population of pancreatic endocrine progenitor cells into the subject.

In a further embodiment, there is provided a method for treating Type 2 diabetes (T2D) in a subject, the method including: (a) implanting a population of pancreatic endocrine progenitor cells into the subject, wherein the subject is a candidate for treatment with one or more small molecule anti-diabetic drugs; and (b) maturing in vivo the population of pancreatic endocrine progenitor cells to produce a population including pancreatic endocrine cells.

In a further embodiment, there is provided a method for treating Type 2 diabetes (T2D) in a subject, the method including: implanting a population of pancreatic endocrine progenitor cells into the subject, wherein the subject is a candidate for treatment with one or more small molecule anti-diabetic drugs.

In a further embodiment, there is provided a method for treating Type 2 diabetes (T2D) in a subject, the method including: (a) implanting a population of pancreatic endocrine progenitor cells into the subject, wherein the subject is being treated with one or more small molecule anti-diabetic drugs; and (b) maturing in vivo the population of pancreatic endocrine progenitor cells to produce a population including pancreatic endocrine cells.

In a further embodiment, there is provided a method for treating Type 2 diabetes (T2D) in a subject, the method including: implanting a population of pancreatic endocrine progenitor cells into the subject, wherein the subject is being treated with one or more small molecule anti-diabetic drugs.

In a further embodiment, there is provided a method for treating obesity in a subject, the method including: (a) implanting a population of pancreatic endocrine progenitor cells into the subject; and (b) maturing in vivo the population of pancreatic endocrine progenitor cells to produce a population including pancreatic endocrine cells.

In a further embodiment, there is provided a method for treating obesity in a subject, the method including: implanting a population of pancreatic endocrine progenitor cells into the subject.

In a further embodiment, there is provided a method for treating control weight gain in a subject, the method including: (a) implanting a population of pancreatic endocrine progenitor cells into the subject; and (b) maturing in vivo the population of pancreatic endocrine progenitor cells to produce a population including pancreatic endocrine cells.

In a further embodiment, there is provided a method for treating control weight gain in a subject, the method including: implanting a population of pancreatic endocrine progenitor cells into the subject.

In a further embodiment, there is provided a method for treating obesity in a subject, the method including: (a) administering a therapeutically effective amount of one or more small molecule anti-diabetic drugs to the subject; (b) implanting a population of pancreatic endocrine progenitor cells into the subject; and (c) maturing in vivo the population of pancreatic endocrine progenitor cells to produce a population including pancreatic endocrine cells.

In a further embodiment, there is provided a method for treating obesity in a subject, the method including: (a) administering a therapeutically effective amount of one or more small molecule anti-diabetic drugs to the subject; and (b) implanting a population of pancreatic endocrine progenitor cells into the subject.

In a further embodiment, there is provided a method for treating control weight gain in a subject, the method including: (a) administering a therapeutically effective amount of one or more small molecule anti-diabetic drugs to the subject; (b) implanting a population of pancreatic endocrine progenitor cells into the subject; and (c) maturing in vivo the population of pancreatic endocrine progenitor cells to produce a population including pancreatic endocrine cells.

In a further embodiment, there is provided a method for treating control weight gain in a subject, the method including: (a) administering a therapeutically effective amount of one or more small molecule anti-diabetic drugs to the subject; and (b) implanting a population of pancreatic endocrine progenitor cells into the subject.

In a further embodiment, there is provided a method for treating obesity, glucose intolerance or insulin resistance in a subject with T2D, the method including: (a) implanting a population of pancreatic endocrine progenitor cells into the subject; and (b) maturing in vivo the population of pancreatic endocrine progenitor cells to produce a population including pancreatic endocrine cells.

In a further embodiment, there is provided a method for treating obesity, glucose intolerance or insulin resistance in a subject with T2D, the method including: implanting a population of pancreatic endocrine progenitor cells into the subject.

In a further embodiment, there is provided a method for treating obesity, glucose intolerance or insulin resistance in a subject with T2D, the method including: (a) administering a therapeutically effective amount of one or more small molecule anti-diabetic drugs to the subject; (b) implanting a population of pancreatic endocrine progenitor cells into the subject; and (c) maturing in vivo the population of pancreatic endocrine progenitor cells to produce a population including pancreatic endocrine cells.

In a further embodiment, there is provided a method for treating obesity, glucose intolerance or insulin resistance in a subject with T2D, the method including: (a) administering a therapeutically effective amount of one or more small molecule anti-diabetic drugs to the subject; and (b) implanting a population of pancreatic endocrine progenitor cells into the subject.

In a further embodiment, there is provided a method improving glycemic control in a subject with T2D, the method including: (a) implanting a population of pancreatic endocrine progenitor cells into the subject, wherein the subject is a candidate for treatment with one or more small molecule anti-diabetic drugs; and (b) maturing in vivo the population of pancreatic endocrine progenitor cells to produce a population including pancreatic endocrine cells.

In a further embodiment, there is provided a method improving glycemic control in a subject with T2D, the method including: implanting a population of pancreatic endocrine progenitor cells into the subject, wherein the subject is a candidate for treatment with one or more small molecule anti-diabetic drugs.

In a further embodiment, there is provided a method improving glycemic control in a subject with T2D, the method including: (a) administering a therapeutically effective amount of one or more small molecule anti-diabetic drugs to the subject; (b) implanting a population of pancreatic endocrine progenitor cells into the subject, wherein the subject is a candidate for treatment with one or more small molecule anti-diabetic drugs; and (c) maturing in vivo the population of pancreatic endocrine progenitor cells to produce a population including pancreatic endocrine cells.

In a further embodiment, there is provided a method improving glycemic control in a subject with T2D, the method including: (a) administering a therapeutically effective amount of one or more small molecule anti-diabetic drugs to the subject; and (b) implanting a population of pancreatic endocrine progenitor cells into the subject, wherein the subject is a candidate for treatment with one or more small molecule anti-diabetic drugs.

In a further embodiment, there is provided a use of a population of pancreatic endocrine progenitor cells for treating Type 2 diabetes (T2D) in a subject, wherein the cells are suitable for implanting into the subject; and maturing in vivo to produce a population including pancreatic endocrine cells.

In a further embodiment, there is provided a use of a population of pancreatic endocrine progenitor cells for treating Type 2 diabetes (T2D) in a subject, wherein the cells are suitable for implanting into the subject.

In a further embodiment, there is provided a use of a population of pancreatic endocrine progenitor cells and one or more small molecule anti-diabetic drugs for treating Type 2 diabetes (T2D) in a subject, wherein the cells are suitable for implanting into the subject; and maturing in vivo to produce a population including pancreatic endocrine cells.

In a further embodiment, there is provided a use of a population of pancreatic endocrine progenitor cells and one or more small molecule anti-diabetic drugs for treating Type 2 diabetes (T2D) in a subject, wherein the cells are suitable for implanting into the subject.

In a further embodiment, there is provided a use of a population of pancreatic endocrine progenitor cells for treating obesity in a subject, wherein the cells are suitable for implanting into the subject; and maturing in vivo to produce a population including pancreatic endocrine cells.

In a further embodiment, there is provided a use of a population of pancreatic endocrine progenitor cells for treating obesity in a subject, wherein the cells are suitable for implanting into the subject.

In a further embodiment, there is provided a use of a population of pancreatic endocrine progenitor cells for treating control weight gain in a subject, wherein the cells are suitable for implanting into the subject; and maturing in vivo to produce a population including pancreatic endocrine cells.

In a further embodiment, there is provided a use of a population of pancreatic endocrine progenitor cells for treating control weight gain in a subject, wherein the cells are suitable for implanting into the subject.

In a further embodiment, there is provided a use of a population of pancreatic endocrine progenitor cells and a therapeutically effective amount of one or more small molecule anti-diabetic drugs for treating obesity in a subject, wherein the cells are suitable for implanting into the subject and maturing in vivo to produce a population including pancreatic endocrine cells.

In a further embodiment, there is provided a use of a population of pancreatic endocrine progenitor cells and a therapeutically effective amount of one or more small molecule anti-diabetic drugs for treating obesity in a subject, wherein the cells are suitable for implanting into the subject.

In a further embodiment, there is provided a use of a population of pancreatic endocrine progenitor cells and a therapeutically effective amount of one or more small molecule anti-diabetic drugs for treating control weight gain in a subject, wherein the cells are suitable for implanting into the subject and maturing in vivo to produce a population including pancreatic endocrine cells.

In a further embodiment, there is provided a use of a population of pancreatic endocrine progenitor cells and a therapeutically effective amount of one or more small molecule anti-diabetic drugs for treating control weight gain in a subject, wherein the cells are suitable for implanting into the subject.

In a further embodiment, there is provided a use of a population of pancreatic endocrine progenitor cells for treating obesity, glucose intolerance or insulin resistance in a subject with T2D, wherein the cells are suitable for implanting into the subject and maturing in vivo to produce a population including pancreatic endocrine cells.

In a further embodiment, there is provided a use of a population of pancreatic endocrine progenitor cells for treating obesity, glucose intolerance or insulin resistance in a subject with T2D, wherein the cells are suitable for implanting into the subject.

In a further embodiment, there is provided a use of a population of pancreatic endocrine progenitor cells and a therapeutically effective amount of one or more small molecule anti-diabetic drugs for treating obesity, glucose intolerance or insulin resistance in a subject with T2D, wherein the cells are suitable for implanting into the subject and maturing in vivo to produce a population including pancreatic endocrine cells.

In a further embodiment, there is provided a use of a population of pancreatic endocrine progenitor cells and a therapeutically effective amount of one or more small molecule anti-diabetic drugs for treating obesity, glucose intolerance or insulin resistance in a subject with T2D, wherein the cells are suitable for implanting into the subject.

In a further embodiment, there is provided a use of a population of pancreatic endocrine progenitor cells for improving glycemic control in a subject with T2D, wherein the cells are suitable for implanting into the subject and maturing in vivo to produce a population including pancreatic endocrine cells.

In a further embodiment, there is provided a use of a population of pancreatic endocrine progenitor cells for improving glycemic control in a subject with T2D, wherein the cells are suitable for implanting into the subject.

In a further embodiment, there is provided a use of a population of pancreatic endocrine progenitor cells and a therapeutically effective amount of one or more small molecule anti-diabetic drugs for improving glycemic control in a subject with T2D, wherein the cells are suitable for implanting into the subject and maturing in vivo to produce a population including pancreatic endocrine cells.

In a further embodiment, there is provided a use of a population of pancreatic endocrine progenitor cells and a therapeutically effective amount of one or more small molecule anti-diabetic drugs for improving glycemic control in a subject with T2D, wherein the cells are suitable for implanting into the subject.

In a further embodiment, there is provided a commercial package including: (a) a population of pancreatic endocrine progenitor cells; and (b) a therapeutically effective amount of one or more small molecule anti-diabetic drugs.

In a further embodiment, there is provided a commercial package including: (a) a population of pancreatic endocrine progenitor cells; and (b) a therapeutically effective amount of one or more small molecule anti-diabetic drugs.

The method may further include treating the subject with one or more small molecule anti-diabetic drugs. The one or more small molecule anti-diabetic drugs may be selected from the following: of dipeptidyl-peptidase 4 (DPP-4) inhibitors; thiazolidinediones; and biguanides. The anti-diabetic drug may be selected from the group including of: sitagliptin; metformin; and rosiglitazone. The one or more small molecule anti-diabetic drugs may be selected from the following: meglitinides; sulfonylureas; dipeptidyl-peptidase 4 (DPP-4) inhibitors; biguanides; thiazolidinediones; alpha-glucosidase inhibitors; sodium-glucose transporter 2 (SGLT-2) inhibitors; and bile acid sequestrants. The small molecule anti-diabetic drug may be selected from the group including of: repaglinide; nateglinide; glipizide; glimepiride; glyburide; saxagliptin; sitagliptin; linagliptin; metformin; rosiglitazone; pioglitazone; acarbose; miglitol; canagliflozin; dapagliflozin; empagliflozin; and colsevelam. The anti-diabetic drug may be sitagliptin. The anti-diabetic drug may be metformin. The anti-diabetic drug may be rosiglitazone.

The pancreatic endocrine progenitor cells may mature in vivo to produce a population comprising at least 2% pancreatic endocrine cells. The pancreatic endocrine progenitor cells may be encapsulated. The pancreatic endocrine progenitor cells may be unencapsulated. The pancreatic endocrine progenitor cells may be macro-encapsulated. The pancreatic endocrine progenitor cells may be micro-encapsulated. The population including pancreatic endocrine cells may be a mixed population. The population including pancreatic endocrine cells may include mature islet cells. The population including pancreatic endocrine cells may include mature pancreatic endocrine cells. The population including pancreatic endocrine cells may include beta-cells. The population including pancreatic endocrine cells may include alpha-cells.

The commercial package may further include instructions for the treatment of T2D. The commercial package may further include instructions for the treatment of obesity. The commercial package may further include instructions for glycemic control.

BRIEF DESCRIPTION OF THE DRAWINGS

FIGS. 2B and 2C show the results of human C-peptide measurement at 18 weeks post-transplant following an intraperitoneal glucose tolerance test (ipGTT) for mice of Example 2 wherein FIG. 2B are the normalized baseline levels and FIG. 2C are the raw levels (ng/mL).

FIG. 3 shows a graph with the percentage of cells with devices that were immuno-reactive for insulin, glucagon, or both hormones (Ins+/Gcg+).

FIGS. 4A and 4B show graphs depicting the HbA1C levels in the mice of Example 4 measured at 12 and 24 weeks post-transplant.

FIG. 4C shows a graph depicting blood glucose levels 20 weeks post-transplant and measured after an overnight fast and 40 minutes following an oral meal challenge in the mice of Example 4.

FIGS. 4D and 4E show graphs depicting the results of intraperitoneal glucose tolerance testing performed 18 weeks (4D) and 24 weeks (4E) post-transplant in the mice of Example 4.

FIG. 4F shows a graph depicting the results of insulin tolerance testing performed 22 weeks post-transplant in the mice of Example 4.

FIGS. 6A-6E show graphs depicting the results of oral glucose tolerance testing performed on Example 6 mice 12 weeks post-transplant.

FIGS. 9A and 9B show graphs of the results of intraperitoneal glucose tolerance tests performed on the mice of Example 4 at 18 weeks (9A) and 24 weeks (9B) post-transplant.

FIG. 11A shows 2 graphs of fasting blood glucose (left) and body weight levels (right) of a subset of the Example 6 mice.

FIG. 11B shows 2 graphs of fasting blood glucose (left) and body weight levels (right) following administration of either a low fat diet or a high fat diet to the Example 6 mice.

FIGS. 14A and 14B show two graphs of body weight in grams (BW—14A) and blood glucose in mM (BG—4 hour fast —14B) comparing transplanted Stage 7 cells to human islet transplants in mice and non-diabetic mice, wherein a subset of human islet transplant mice were non-diabetic (i.e. not STZ treated) and the remainder were "diabetic" (i.e. STZ treated).

FIGS. 17B-D are the weights of the epididymal fat, mesenteric fat, and all fat pads combined, respectively.

DETAILED DESCRIPTION OF THE INVENTION

Figure 1A:
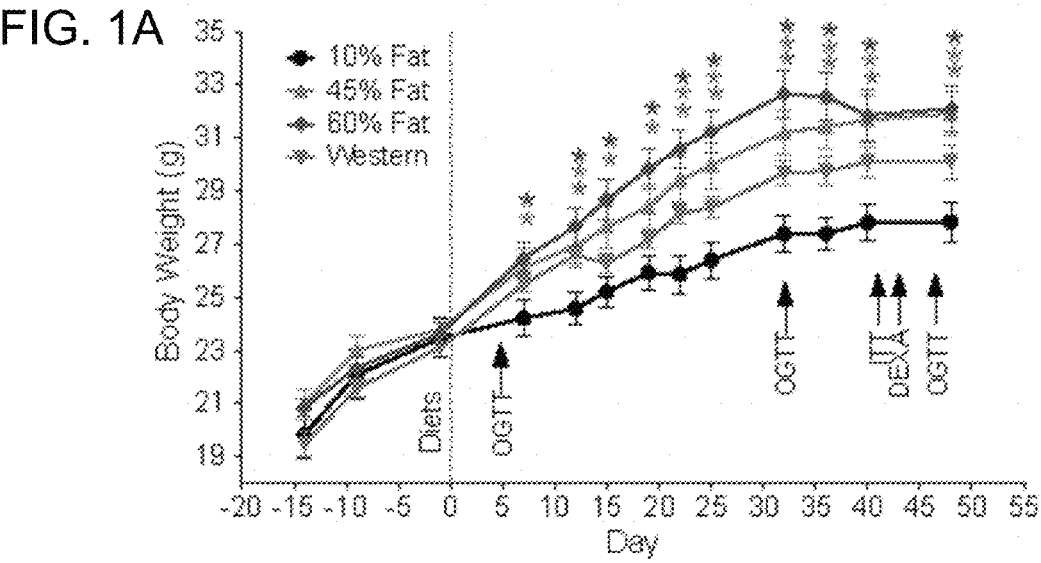
FIG. 1A shows a graph depicting the fasting body weights of the mice from Example 1 at the specified days following administration of a low fat diet (10% Fat), diets high in fat (45% Fat; 60% Fat), or a high fat, high carbohydrate diet (Western).
Figure 1B:
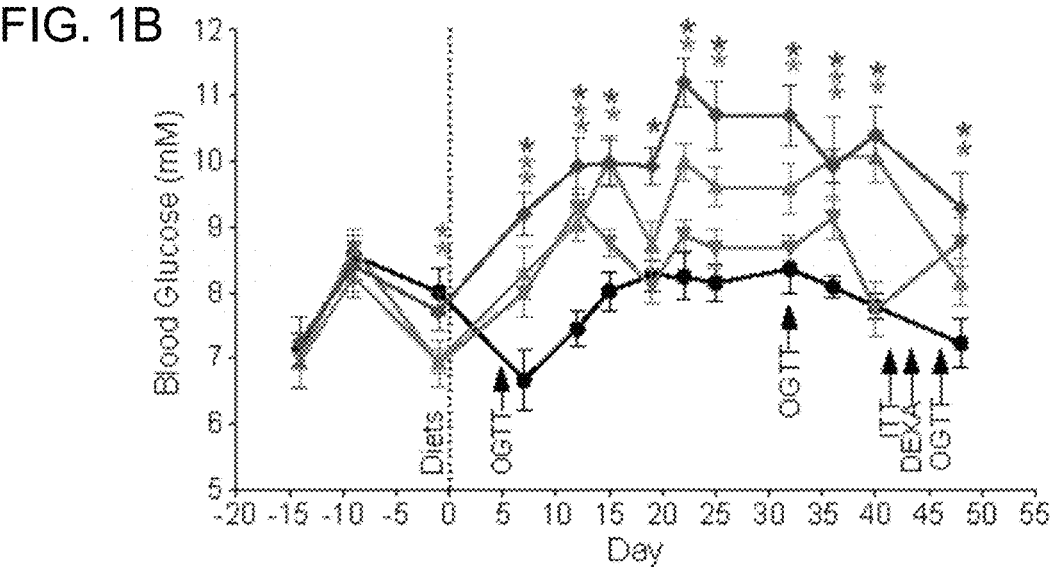
FIG. 1B shows a graph depicting the fasting blood glucose levels of the mice from Example 1 at the specified days following administration of a low fat diet (10% Fat), diets high in fat (45% Fat; 60% Fat), or a high fat, high carbohydrate diet (Western).
Figure 1C:
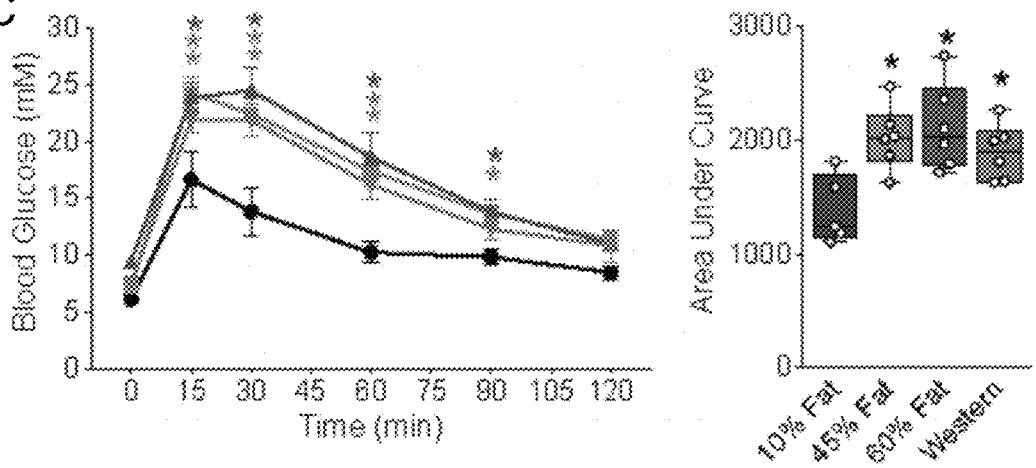
FIG. 1C shows a graph of the raw values and area under the curve of the blood glucose values during an oral glucose challenge of the mice in Example 1 mice at Day 47

The following detailed description of the invention will be better understood when read in conjunction with the appended figures. For the purpose of illustrating the invention, the figures demonstrate embodiments of the present invention. However, the invention is not limited to the precise arrangements, examples, and instrumentalities shown.

The present invention is directed to the discovery that transplantation of pancreatic endocrine precursor cells into a subject for further differentiation into functional pancreatic endocrine cells, alone or in combination with the administration of a therapeutically effective amount of an anti-diabetic drug, results in weight loss in the subject. Additionally, co-therapy that includes transplantation of pancreatic endocrine precursor cells for further differentiation into functional pancreatic endocrine cells, alone or in combination with the administration of a therapeutically effective amount of selected anti-diabetic drugs, results in improvement in glucose tolerance and insulin resistance in Type 2 diabetes (T2D) model mammals.

Thus, embodiments of the present invention provide a method for treating obesity in a subject comprising: (a) implanting a population of pancreatic endocrine progenitor cells into the subject; and (b) maturing in vivo the population of pancreatic endocrine precursor cells. Optionally, the method may include administering a therapeutically effective amount of one or more anti-diabetic drugs to the subject. Alternatively, embodiments of the present invention provide a method for treating obesity in a subject comprising: (a) implanting a population of pancreatic endocrine progenitor cells into the subject; and (b) maturing in vivo the population of pancreatic endocrine precursor cells to produce a population of cells comprising about 2% or more of pancreatic endocrine cells. Optionally, the method may include administering a therapeutically effective amount of one or more anti-diabetic drugs to the subject. Additionally, embodiments of the invention may provide a method for treating obesity, glucose intolerance and insulin resistance in a subject with T2D comprising: (a) implanting a population of pancreatic endocrine progenitor cells into the subject; (b) maturing in vivo the population of pancreatic endocrine precursor cells; and (c) administering a therapeutically effective amount of one or more anti-diabetic drugs to the subject, wherein the anti-diabetic drugs are selected from the group consisting of dipeptidyl-peptidase 4 inhibitors, thiazolidinediones, and biguanides. Alternatively, other embodiments of the present invention provide a method for treating obesity in a subject comprising: (a) implanting a population of pancreatic endocrine progenitor cells into the subject; (b) maturing in vivo the population of pancreatic endocrine precursor cells to produce a population of cells comprising about 2% or more of pancreatic endocrine cells. Optionally, the method includes administering a therapeutically effective amount of one or more anti-diabetic drugs to the subject. Additionally, the invention provides a method for treating obesity, glucose intolerance and insulin resistance in a subject with T2D comprising: (a) implanting a population of pancreatic endocrine precursor cells into the subject; (b) maturing in vivo the population of pancreatic endocrine precursor cells to produce a population comprising about 2% or more of pancreatic endocrine cells; and (c) administering a therapeutically effective amount of one or more anti-diabetic drugs to the subject, wherein the anti-diabetic drugs are selected from the group consisting of dipeptidyl-peptidase 4 inhibitors, thiazolidinediones, and biguanides. Still in some embodiments, the various indicated pancreatic endoderm-lineage cells or as defined herein as pancreatic progenitor cells, which includes cells of Stages 4, 5, 6 and 7 or pancreatic endocrine cells derived from an in vitro maturation process as described herein may be used alone or in combination, but independent of any anti-diabetic drug, and used to treat obesity, glucose intolerance, glycemic control and insulin resistance.

The stem cells or pluripotent stem cells used to provide the pancreatic endocrine precursor cells useful in the invention are undifferentiated cells defined by their ability, at the single cell level, to both self-renew and differentiate including but not limited to human embryonic stem cells, induced pluripotent stem cells, human umbilical cord tissue-derived cells, human amniotic fluid-derived cells, human placental-derived cells, and human parthenote-derived stem cells. The stem cells are also characterized by their ability to differentiate in vitro into functional cells of various cell lineages from multiple germ layers (endoderm, mesoderm, and ectoderm). The stem cells also give rise to tissues of multiple germ layers following transplantation and contribute substantially to most, if not all, tissues following injection into blastocysts.

The stem cells are differentiated, which differentiation is the process by which an unspecialized ("uncommitted") or less specialized cell acquires the features of a specialized cell. A differentiated cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type.

Markers may be used to characterize the stem cells and the various differentiated cells. "Markers", as used herein, are nucleic acid or polypeptide molecules that are differentially expressed in a cell of interest. In this context, differential expression means an increased level for a positive marker and a decreased level for a negative marker as compared to an undifferentiated cell, a cell at another stage of differentiation within the same lineage, or a cell of a different lineage. The detectable level of the marker nucleic acid or polypeptide is sufficiently higher or lower in the cells of interest compared to other cells, such that the cell of interest can be identified and distinguished from other cells using any of a variety of methods known in the art.

The differentiation process is often viewed as progressing through a number of consecutive stages. For purposes of one embodiment of this invention, in the step-wise differentiation, "Stage 1" refers to the first step in the differentiation process in which pluripotent stem cells are differentiated into cells expressing markers characteristic of the definitive endoderm ("Stage 1 cells"). "Stage 2" refers to the second step, the differentiation of cells expressing markers characteristic of the definitive endoderm cells into cells expressing markers characteristic of gut tube cells ("Stage 2 cells"). "Stage 3" refers to the third step, differentiation of cells expressing markers characteristic of gut tube cells into cells expressing markers characteristic of foregut endoderm cells ("Stage 3 cells"). "Stage 4" refers to the fourth step, the differentiation of cells expressing markers characteristic of foregut endoderm cells into cells expressing markers characteristic of pancreatic endocrine precursor cells ("Stage 4 cells"). In other embodiments, the step-wise differentiation process includes differentiating pancreatic foregut precursor cells into pancreatic endocrine precursor cells ("Stage 5 cells") or immature endocrine cells ("Stage 6 cells") and, subsequently, further differentiation into more mature endocrine cells ("Stage 7 cells"), each stage identified by specific markers characteristic of the cells at the given stage. The actual numbered stage, however, is not limiting as a particular population of cells is defined by any of cell types in the population, which cell types are identified by the markers they express relative to other cell types in the same population.

It is to be noted that not all cells in a particular population progress through the stages at the same rate. Consequently, it is not uncommon in in vitro cell cultures to detect the presence of cells that have progressed less, or more, down the differentiation pathways than the majority of cells present in the population, particularly at the later differentiation stages. For purposes of illustrating the present invention, characteristics of the various cell types associated with the above-identified stages are described herein.

"Definitive endoderm" or "endoderm-lineage cells" or equivalents thereof as used herein, refers to cells that express at least one of the following markers: FOXA2 (also known as hepatocyte nuclear factor 3-beta ("HNF3-beta")), GATA 4, SOX17, CXCR4, Brachyury, Cerberus, OTX2, goosecoid, C-Kit, CD99, and MIXL1. Markers characteristic of the definitive endoderm cells are CXCR4, FOXA2, and SOX17.

"Gut tube cells" or equivalents thereof, as used herein, refers to cells derived from definitive endoderm that may be characterized by their substantially increased expression of HNF4-alpha over that expressed by definitive endoderm cells.

"Foregut endoderm cells" or "PDX1 pancreatic endoderm cells" or equivalents thereof, as used herein, refers to cells that express at least one of the following markers: PDX1, FOXA2, CDX2, SOX2, and HNF4-alpha. Foregut endoderm cells may be characterized by an increase in expression of PDX1 compared to gut tube cells.

"Pancreatic foregut precursor cells", or "pancreatic progenitor cells" or "Stage 4 cells" (S4 cells), or equivalents thereof as used herein, refers to cells that express at least one of the following markers: PDX1, NKX6.1, HNF6, SOX9, FOXA2, PTF1a, PROX1 and HNF4 alpha. More specifically, pancreatic foregut precursor cells may be identified by being positive for the expression of at least one of PDX1, NKX6.1 and SOX9 and with low expression of NGN3 and NeuroD.

"Pancreatic endocrine precursor cells" or "Stage 5 cells" (Stage 5 cells) or "pancreatic endoderm cells" or equivalents thereof, as used herein, refers to pancreatic endoderm cells capable of becoming a pancreatic hormone expressing cell and that express at least one of the following markers: NGN3; NKX2.2; NeuroD1; ISL1; PDX1; PAX4; PAX6; NKX6.1, or ARX. Pancreatic endocrine precursor cells may be characterized by their expression of NKX2.2, NKX6.1, PDX1 and NeuroD1.

"Pancreatic endocrine cells," or "Pancreatic hormone expressing cell", or "Cells expressing markers characteristic of the pancreatic endocrine lineage" or "Stage 6 or 7 cells" (S6 or S7 cells) or equivalents thereof as used herein, refer to cells capable of expressing at least one of the following hormones: insulin, glucagon, somatostatin, ghrelin, and pancreatic polypeptide. In addition to these hormones, markers characteristic of pancreatic endocrine cells include one or more of NGN3, NeuroD1, ISL1, PDX1, NKX6.1, PAX4, ARX, NKX2.2, MNX1 (Hb9) and PAX6. Pancreatic endocrine cells expressing markers characteristic of beta-cells can be characterized by their expression of insulin and at least one of the following transcription factors: PDX1, NKX2.2, NKX6.1, NeuroD1, ISL1, HNF3-beta, MAFA, MNX1 and PAX6. "More mature endocrine cells" express markers characteristic of pancreatic endocrine cells, but have a more mature phenotype as compared to immature endocrine cells meaning that the more mature endocrine cells not only are insulin+, MAFA+, NKX6.1+ and PDX1+, but also display glucose responsive insulin secretion.

"Functional pancreatic beta-cell" or "beta-cell" equivalents thereof as used herein, refer to an insulin positive cell capable of being glucose responsive and positive for PDX-1 and NKX6.1 as referred to in US20150353895; or a "SC-beta-cell" as referred to in WO2015002724. Still in some embodiments, the functional pancreatic beta cell expresses at least one marker characteristic of an endogenous mature pancreatic beta-cell selected from the group consisting of insulin, C-peptide, PDX1, MAFA, NKX6-1, PAX6, NEU-ROD1 (or NEUROD), glucokinase (GCK), SLC2A 1, PCS1, KCNJ11, ABCC8, SLC30A8, SNAP25, RAB3A, GAD2, PTPRN, NKX2-2, PAX4, IRX1, and IRX2.

"Appropriate growth factors" or "appropriate factors" or equivalents thereof refers to those particular growth factors and agents used to differentiate a population of cells from one stage to another or further differentiated stage. The appropriate factors or agents for each of the differentiation steps or stages are described in detail in D'Amour, K A. et al. 2005, D'Amour, K A. et al. 2006, Kroon E. et al. 2008, Schulz T. et al. 2012, Rezania A. et al. 2014, Bruin J. et al. 2014, Pagliuca F W. et al. 2014, Agulnick A. D. et al. 2015 (see also WO/2014/160413) and the like.

Cells useful in the methods of the invention may be any population of Stage 4 or Stage 5 pancreatic endocrine precursor cells, or Stage 6 or Stage 7 pancreatic endocrine cells and all cells up to, but not including mature beta-cells, and are collectively referred to as "pancreatic endocrine progenitor cells". Alternatively, cells useful in the methods may further include endocrine cells and in vitro matured pancreatic endocrine cells. Alternatively, cells useful in the invention may be any of a population of immature pancreatic endocrine cells or more mature endocrine cells that are not only insulin+, MAFA+, NKX6.1+, and PDX1+ but also display glucose responsive insulin secretion. Preferably, the cells used in the invention are pancreatic endocrine precursor cells.

"Subject" or equivalents thereof as used herein refers to an animal, preferably a mammal, most preferably a human adult or child. "Obesity" as used herein means an accumulation of body fat that is undesirable or equal to or greater than about 20% of a subject's ideal body weight. "Effective amount" or equivalents thereof of a compound, growth factor or agent refers to that concentration of the compound, growth factor or agent that is sufficient in the presence of the remaining components of the cell culture medium to either maintain the cell in an undifferentiated state (e.g. pluripotent cells) or promote differentiation of a cell. This concentration is readily determined by one of ordinary skill in the art and for many of the cell types described herein, the effective amount is described in detail in at least D'Amour, K A. et al. 2005, D'Amour, K A. et al. 2006, Kroon E. et al. 2008, Schulz T. et al. 2012, Rezania A. et al. 2014, Bruin J. et al. 2014, Pagliuca F W. et al. 2014, Agulnick A. D. et al. 2015 and the like. In some embodiments, the therapeutic effective amount is as compared to cell cultures which do not receive the same treatment or therapeutic effective amount of the compound, growth factor or agent. "Therapeutic effective amount" or equivalents thereof as used herein refer to one or more small molecule anti-diabetic drugs given alone or in combination to provide the desired benefit to the subject.

In some embodiments, the methods and co-therapies of the invention utilize anti-diabetic drugs in addition to implanted, differentiated cells, to treat one or both of obesity and glucose intolerance in a subject. By "anti-diabetic drug" or "anti-diabetic medication" is meant a medication, agent or the like that acts to lower blood sugar levels in a person with T2D.

The anti-diabetic drugs useful in the invention may work by any of a number of ways to lower blood sugar, including simulating insulin release and production from the pancreas, inhibiting glucose release from the liver, inhibiting stomach enzymes that break-down carbohydrates, improving cells sensitivity to insulin, inhibiting glucose reabsorption in the kidneys, or slowing food motility in the stomach. These anti-diabetic drugs include the following oral medications: meglitinides, for example such as repaglinide and nateglinide; sulfonylureas, such as glipizide, glimepiride, and glyburide; dipeptidyl-peptidase 4 ("DPP-4") inhibitors such as saxagliptin, sitagliptin, and linagliptin; biguanides such as metformin; thiazolidinediones such as rosiglitazone and pioglitazone; alpha-glucosidase inhibitors such as acarbose and miglitol; sodium-glucose transporter 2 ("SGLT2") inhibitors such as canagliflozin, dapagliflozin, and empagliflozin; and bile acid sequestrants such as colsevelam. Alternatively, injectable medications, such as amylin mimetics, including pranlintide, and incretin mimetics, including GLP-1 receptor agonists, such as exenatide and liraglutide.

The anti-diabetic drugs are used in "therapeutically effective amounts", meaning the amount of anti-diabetic drug that elicits the biological or medicinal response in a tissue system, animal or human that is being sought by a researcher, veterinarian, medical doctor, or other clinician, which includes alleviation of one or more of the symptoms of the disease or disorder being treated or the reduction of the severity of one or more symptom of the disease or disorder being treated.

Any pluripotent stem cells may be used in the invention to provide the pancreatic endocrine precursor, pancreatic foregut precursor, and mature endocrine cells. Exemplary types of pluripotent stem cells that may be used include established lines of pluripotent cells, including pre-embryonic tissue (such as, a blastocyst), embryonic tissue, or fetal tissue taken any time during gestation, typically but not necessarily, before approximately 10 to 12 weeks gestation. Non-limiting examples are established lines of human embryonic stem cells (hESCs) or human embryonic germ cells, such as, any of the current 362 human embryonic stem cell lines listed on the NIH Human Embryonic Stem Cell Registry including but not limited to H1 (NIH Code: WA01), H7 (NIH Code: WA07), H9 (NIH Code: WA09) (WiCell Research Institute™, Madison, Wis., USA), SA002 (Cellartis A B Corporation™, Goteburg, Sweden), CyT 49 (ViaCyte, Inc.). Pluripotent stem cell markers include, for example, the expression of one or more of the following: ABCG2, cripto, FOXD3, CONNEXIN43, CONNEXIN45, OCT4, SOX2, NANOG, hTERT, UTF1, ZFP42, SSEA-3, SSEA-4, TRA-1-60, TRA-1-81. These may be detectable by RT-PCR or flow cytometry or similar technologies now or later developed.

Cells taken from a pluripotent stem cell population already cultured in the absence of feeder cells are also suitable. Induced pluripotent cells (IPS), or reprogrammed pluripotent cells, derived from adult somatic cells using forced expression of a number of pluripotent related transcription factors, such as OCT4, NANOG, SOX2, KLF4, and ZFP42 (Loh, Y H. et al. 2011,f; see also IPS, Takahashi, K. and Yamanaka, S. 2006) may also be used. The human embryonic stem cells used in the methods of the invention may also be prepared as described by Thomson et al. (U.S. Pat. No. 5,843,780; Thomson, J A. et al. 1998; Thomson, J A. and Marshall, V S. 1998; Thomson, J A. et al. 1995). Mutant human embryonic stem cell lines, such as, BG01v (BresaGen™, Athens, Ga.), or cells derived from adult human somatic cells, such as, cells disclosed in Takahashi et al. 2007 may also be used. In certain embodiments, pluripotent stem cells suitable for use in the present invention may be derived according to the methods described in: Li et al. 2009; Maherali et al. 2007; Stadtfeld et al. 2008; Nakagawa et al. 2008; Takahashi et al. 2007; and U.S. Patent App. Pub. No. 2011/0104805. In certain embodiments, pluripotent stem cells suitable for use in the present invention may be considered "naïve" and derived according to the methods described in: Gafni et al. 2013, and Ware et al. 2014.

In certain embodiments, the pluripotent stem cells may be of non-embryonic origins. Yet other sources of suitable cells include human umbilical cord tissue-derived cells, human amniotic fluid-derived cells, human placental-derived cells, and human parthenotes. In one embodiment, the umbilical cord tissue-derived cells may be obtained by the method of U.S. Pat. No. 7,510,873. In another embodiment, the placental tissue-derived cells may be obtained using the methods of U.S. Patent Application Publication No. 2005/0058631. In another embodiment, the amniotic fluid-derived cells may be obtained using the methods of U.S. Patent App. Pub. No. 2007/0122903. Each of these patent applications is incorporated in its entirety herein as it pertains to the isolation and characterization of the cells.

Pluripotent stem cells are typically cultured on a layer of feeder cells that support the pluripotent stem cells in various ways. Alternatively, the pluripotent stem cells may be cultured in a culture system that is essentially free of feeder cells, but nonetheless supports proliferation of pluripotent stem cells without undergoing substantial differentiation. The growth of pluripotent stem cells in feeder-free culture without differentiation is often supported using a medium conditioned by culturing previously with another cell type. Alternatively, the growth of pluripotent stem cells in feeder-free culture without differentiation can be supported using a chemically defined medium.

Pluripotent cells may be readily expanded in culture using various feeder layers or by using matrix protein coated vessels. Alternatively, chemically defined surfaces in combination with defined media such as media sold under the trademark mTeSR™-1 and TeSR™-2 (StemCell Technologies, Inc.™, Vancouver, B.C., Canada) may be used for routine expansion of the undifferentiated cells. Pluripotent cells may be readily removed from culture plates using enzymatic digestion, mechanical separation, or various calcium chelators such as ethylenediaminetetraacetic acid ("EDTA"). Alternatively, pluripotent cells may be expanded in suspension in the absence of any matrix proteins or feeder layer.

The pluripotent stem cells may be plated onto a suitable culture substrate. An exemplary suitable culture substrate is an extracellular matrix component, such as those derived from basement membrane or that may form part of adhesion molecule receptor-ligand couplings. A suitable culture substrate is a reconstituted basement membrane sold under the trademark MATRIGEL™ (Corning Incorporated™, Corning, N.Y.).

Other extracellular matrix components and component mixtures known in the art are suitable as an alternative. Depending on the cell type being proliferated, this may include laminin, fibronectin, proteoglycan, entactin, heparin sulfate, and the like, alone or in various combinations.

The pluripotent stem cells may be plated onto the substrate in a suitable distribution and in the presence of a medium, which promotes cell survival, propagation, and retention of the desirable characteristics.

As pluripotent cells differentiate towards beta-cells, they differentiate through various stages each of which may be characterized by the presence or absence of particular markers. Differentiation of the cells into these stages is achieved by the specific culturing conditions including the presence and lack of certain factors added to the culture media. In general, this process involves differentiation of pluripotent stem cells into definitive endoderm cells. These definitive endoderm cells may then be further differentiated into gut tube cells, which in turn may then be differentiated into foregut endoderm cells. In one embodiment, foregut endoderm cells may be differentiated into pancreatic foregut precursor cells which may then be further differentiated into pancreatic endocrine precursor cells. These cells may be yet further differentiated into pancreatic hormone producing or secreting cells. In another embodiment, the foregut endoderm cells may be differentiated into pancreatic endocrine precursor cells and further differentiated into pancreatic hormone producing or secreting cells.

In certain embodiments of the invention, to arrive at the cells expressing markers characteristic of the pancreatic endocrine precursor cells, a protocol starting with pluripotent stem cells is employed. This protocol includes:

Stage 1: Pluripotent stem cells such as embryonic stem cells obtained from cell culture lines are treated with the appropriate factors to induce formation of definitive endoderm cells.

Stage 2: Cells resulting from Stage 1 are treated with the appropriate factors to induce formation of cells into markers expressing characteristic of gut tube cells.

Stage 3: Cells resulting from Stage 2 cells are treated with the appropriate factors to induce further differentiation into cells expressing markers characteristic of foregut endoderm cells.

Stage 4: Cells resulting from Stage 3 are treated with the appropriate factors to induce further differentiation into cells expressing markers characteristic of pancreatic pancreatic endoderm lineage expressing at least one of the following markers: PDX1, NKX6.1, HNF1 beta, PTF1 alpha, HNF6, HNF4 alpha, SOX9, HB9 or PROX1. Cells expressing markers characteristic of the pancreatic endoderm lineage do not substantially express CDX2 or SOX2.

Stage 5: Cells resulting from Stage 4 are treated with the appropriate factors to induce further differentiation into cells expressing markers characteristic of pancreatic endocrine precursor cells capable of becoming a pancreatic hormone expressing cell in particular to maximize induction of NGN3. Such a cell can express at least one of the following markers: NGN3, NKX2.2, NeuroD, ISL-1, Pax4, Pax6, or ARX.

Stage 6 or Stage 7: Cells resulting from Stage 5 or 6 are treated with the appropriate factors to induce further differentiation into cells expressing markers characteristic pancreatic endocrine cells expressing insulin are capable of being glucose responsive and positive for PDX-1 and NKX6.1, and often MAFA.

The invention provides methods of treatment, and in particular for treating subjects suffering from one or more of obesity, glucose intolerance, and insulin resistance. In one embodiment, the method of treatment comprises implanting cells obtained or obtainable by a method of the invention into a subject. In one embodiment, the method of treatment comprises differentiating pluripotent cells in vitro into pancreatic precursor cells, pancreatic endocrine cells or mature endocrine cells, for example as described herein, and implanting the differentiated cells into a subject. In another embodiment, the method further comprises the step of culturing pluripotent stem cells, for example as described herein, prior to the step of differentiating the pluripotent stem cells. In a still further embodiment, the method further comprises the step of differentiating the cells in vivo after the step of implantation. In one embodiment, the subject being treated by any of the methods is a mammal and preferably is a human.

In one embodiment, the cells may be implanted as dispersed cells or formed into clusters that may be infused into the vascular system, for example, the hepatic portal vein. Alternatively, the cells may be provided in a biocompatible, porous, polymeric support, degradable devices or non-degradable devices, or encapsulated (macro or micro encapsulation may be use) to protect the cells from the immune system of the host. Cells may be implanted into an appropriate site in a recipient including, for example, the liver, muscle adipose, pancreas, renal subscapular space, omentum, peritoneum, sub-serosal space, intestine, stomach, or a subcutaneous pocket. The site of transplantation, with or without a cell receptacle, may be pre-vascularized prior to cell implantation. For example, a prevascularized subcutaneous site may be prepared for islet cell transplantation (see Pepper A R. et al. 2015). In fact, the inventors have shown that both Stage 4 and Stage 6 cells can survive, mature and function (i.e. showing both glucose-induction and C-peptide release) following subcutaneous transplant without a device using the Pepper A R. et al. 2015 methodology (data not shown).

Attempts to shield beta-cells from the immune destruction using protective capsules have many challenges (see Tang, Q. and Desai, T A. 2016). For example, materials that are used to encapsulate beta-cells must be permeable to glucose and insulin while preventing immune cells and the toxic molecules that they produce from reaching the beta-cells. Sealing beta cells in such capsules can be problematic, since a high proportion of islets die shortly after transplantation as a result of ischemia, a condition that is worsened by encapsulation because the structure may prevent vascularization of the islets. Moreover, encapsulation can reduce the speed at which beta-cells respond to changes in blood glucose levels because of the time needed for glucose and insulin to diffuse across the space between the capsule surface and the beta-cells. With pancreatic islet clusters, there is one capillary adjacent to each beta-cell for the efficient coupling of blood glucose changes with insulin release. Both problems in beta-cell survival and function can be exacerbated by an inflammatory foreign-body response (FBR), which is often induced by the material used to encapsulate the cells. Macrophages in the transplant recipients recognize the materials as foreign and form a fibrous wall to contain them, which may lead to fouling of the device surface and suffocation of the cells within.

To enhance further differentiation, survival or activity of the implanted cells in vivo, additional factors, such as growth factors, antioxidants, or anti-inflammatory agents may be administered before, simultaneously with, or after administration of the cells. These factors can be secreted by endogenous cells and exposed to the administered cells in situ. Implanted cells can be induced to differentiate by any combination of endogenous and exogenously administered growth factors known in the art. Additionally, it may be beneficial to administer one or more immunosuppressive drugs to the subject pre- or post-cell implantation to prevent rejection of the implanted cells.

The amount of cells used in implantation depends on a number of factors including the condition of the implantation subject and response to the implanted therapy and can be determined by one skilled in the art. The cells can be maintained in vitro on a support prior to implantation into the patient. Alternatively, the support containing the cells can be directly implanted in the patient without additional in vitro culturing. The support can optionally be incorporated with at least one pharmaceutical agent that facilitates the survival and function of the transplanted cells.

Transplantation of pancreatic progenitor cells to a host for in vivo maturation exposes the cells to many environmental influences, which may be permissive, prohibitive, detrimental, beneficial or some combination thereof. Furthermore, the many permutations and combinations of these influences are difficult to predict and the influences are bound to be dependent on many factors (for example, the stage of the cell, the type of cell, the host environment (including, disease state, medications etc.)). For example, cell maturation in a T1D model (i.e. absolute insulin deficiency due to islet destruction with a large STZ dose to mimic the autoimmune response in T1D patients, which requires insulin administration, but depending on the type of insulin treatment, exercise and food intake may still result in hyperglycemia or hypoglycemia) is considerably different in a T2D model (i.e. where there is partial damage to the islet cells, wherein they still produce insulin, if a somewhat insufficient amount and insulin resistance leads to increased blood glucose due to inappropriate release of glucose by the liver and inappropriate regulation of metabolism by the CNS). Furthermore, the role of T2D diabetes medications (for example, repaglinide; nateglinide; glipizide; glimepiride; glyburide; saxagliptin; sitagliptin; linagliptin; metformin; rosiglitazone; pioglitazone; acarbose; miglitol; canagliflozin; dapagliflozin; empagliflozin; and colsevelam) on pancreatic progenitor cell maturation in vivo was not previously understood. In fact Calcineurin inhibitors (for example, Cyclosporine and tacrolimus) are reported to block pancreatic regeneration in a ductal ligation model (see for example, Heit, J J. et al. 2006; and Nir, T D. et al. 2007). Furthermore, exposure to a high fat diet did not appear to influence the maturation process in vivo (see Example 3).

It is possible that one might have predicted insulin replacement from transplanted beta-cells could be therapeutic in T2D, despite the paucity of evidence to support it. However, one could not predict how the pre-requisite precursor cell maturation period, prior to insulin secretion, would be impacted when growing within an environment of T2D. There is evidence that both elevated glycemia and insulin resistance (key characteristics of T2D) can impair beta-cell development (see for example, Jonas, J C. et al. 1999; and Kahraman, S. et al. 2014). Similarly, diet has been shown to influence beta-cell development (see for example, O'Dowd, J F. and Stocker, C J. 2013). Accordingly, whether or not the pancreatic precursor cells would mature into beta-cells and subsequently function appropriately in this environment (hyperglycemia, insulin resistance, similar to T2D), and thereby improve glucose homeostasis required experimentation.

As reported herein the differentiation of the progenitors is different in male versus female mice (maturation to glucose-responsive beta-cells is faster in females than males), something we had not predicted (data not shown; see also FIGS. 12 and 13) and it has also been discovered that the setting of hypothyroidism impairs the differentiation of the pancreatic progenitors (see Bruin, J E. et al. "Hypothyroidism impairs human stem cell-derived pancreatic progenitor cell maturation in mice" Diabetes (2016) pii: db151439. [Epub ahead of print]). Thus environmental influences can indeed disrupt both the maturation and function of the transplanted cells, and this may be unpredictable, such that one should not have assumed maturation of precursor cells into functional beta-cells would occur in the setting of T2D-like parameters.

In terms of the influence of other anti-diabetic medicines, we have previously examined short term effect of insulin and exendin-4; both were without significant effect, under the conditions tested (see for example, Bruin, J E. et al. 2013). However, others have reported that drugs can impair beta-cell regeneration, such as immunosuppressive drugs (see for example, Nir T. et al. 2007).

Materials and Methods

In Vitro Differentiation of hESCs and Assessment of Pancreatic Progenitor Cells

The H1 hESC line was obtained from the WiCell Research Institute™. All experiments at The University of British Columbia (UBC) with H1 cells were approved by the Canadian Stem Cell Oversight Committee and the UBC Clinical Research Ethics Board. Pluripotent H1 cells were differentiated into pancreatic progenitor cells according to our 14-day, four-stage protocol as previously described (Bruin et al., 2013). Other differentiation protocols for producing pancreatic progenitors or endocrine precursors and pancreatic endocrine cells are available and have been shown to develop and mature to become at least insulin secreting cells in response to physiological glucose levels (Kroon E. et al. 2008; Schulz T. et al. 2012; Rezania et al. 2014; Pagliuca, F W. et al. 2014; Agulnick, A D. et al. 2015; and Russ, H A, et al. 2015) Expression of key pancreatic progenitor cell markers or endocrine cell markers are assessed prior to transplantation using well known methodologies including custom Taqman™ qPCR Arrays (Applied Biosystems™).

Flow Cytometry

Differentiated cells were released into a single-cell suspension, fixed, permeabilized, and stained for various intracellular markers, as described previously (Rezania et al., 2012). Dead cells were excluded during FACS analysis and gating was determined using isotype antibodies. Refer to TABLE 1 for antibody details.

TABLE 1

Antibody information for FACS

| Type | Antibody | Source | Dilution |
|---|---|---|---|
| Unconjugated Primary antibodies | Mouse anti-NKX6.1 | Developmental Studies Hybridoma Bank University of Iowa (Cat #F55A12) | 1:400 |
| | Rabbit anti-Synaptophysin | Abcam ™ (Cat #ab52636) | 1:800 |
| | Rabbit anti-Chromogranin A | DAKO ™ (Cat# IS502) | 1:10 |
| | Mouse anti-NKX2.2 | Developmental Studies Hybridoma Bank University of Iowa (Cat# 74.5A5) | 1:100 |
| Conjugated primary antibodies | Alexa Fluor 647 mouse anti-human Ki67 | BD ™ cat# 561126 | 1:10 |
| | PE mouse anti-PDX1 | BD ™ cat# 562161 | 1:40 |
| | PE mouse anti-human Pax6 | BD ™ cat# 561552 | 1:20 |
| | Alexa Fluor 647 mouse anti-Oct3/4 | BD ™ cat# 560329 | 1:20 |
| Secondary antibodies | Goat Anti Mouse IgG AF647 | Invitrogen ™ (Cat# A21235) | 1:4000 |
| | PE-Goat anti-Rabbit Fab2 IgG (H + L) | Invitrogen ™ (Cat# A10542) | 1:800 |
| Isotype control antibodies | Purified Rabbit IgG, k Isotype | BD ™ cat# 550875 | 1:1000 |
| | Purified Mouse IgG, k Isotype | BD ™ cat# 557273 | 1:50 |
| | PE Mouse IgG1, k, Isotype Control | BD ™ cat # 555749 | 1:40 |
| | Alexa Fluor 647 IgG1, Isotype Control | BD ™ cat# 557732 | 1:40 |

Animals

Male SCID-beige mice (C.B-Igh-1b/GbmsTac-Prkdcscid-LystbgN7, 8-10 weeks old; Taconic™) were maintained on a 12 hr light/dark cycle throughout the study. All experiments were approved by the UBC Animal Care Committee and carried out in accordance with the Canadian Council on Animal Care guidelines.

Diets and Drug Administration

All mice were given ad libitum access to a standard irradiated diet (Harlan Laboratories™, Teklad™ diet #2918) for 2 weeks to allow for acclimatization following their arrival at UBC. In the first cohort, mice were placed on one of four different diet regimens (Research Diets™) for the 36-week study (n=11 per diet): (1) "10% fat" control diet (D12450K, 10 kcal % fat, 70 kcal % carbohydrate [no sucrose]), (2) "45% fat" diet (D12451, 45 kcal % fat [primarily lard], 35 kcal % carbohydrate), (3) "60% fat" diet (D12492, 60 kcal % fat [primarily lard], 20 kcal % carbohydrate), or (4) "Western" diet (D12079B, 41 kcal % fat [primarily milk fat], 43 kcal % carbohydrate [primarily sucrose]).

In the second cohort, mice were placed on either the 10% fat control diet (D12450K; n=8) for the duration of the study of 60% fat diet (D12492; n=64) for 6 weeks, followed by one of the following treatment regimens for the remainder of the study (n=16 per group): (1) 60% fat diet with no drug (D12492), (2) 60% fat diet containing rosiglitazone (18 mg/kg diet or ~3 mg/kg BW per day; Cayman Chemical™; Research Diets™ custom diet formulation D08121002), (3) 60% fat diet containing sitagliptin (4 g/kg diet or ~750 mg/kg BW per day; sitagliptin phosphate monohydrate, BioVision™; Research Diets™ custom diet formulation D08062502R), or (4) 60% fat diet (D12492) and metformin (1,1-dimethylbiguanide hydrochloride) in drinking water (1.25 mg/ml or ~250 mg/kg BW per day).

To induce Type 1 diabetes (T1D), a single high dose injection of Streptozotocin (STZ), for example, 190 mg/kg, (see Rezania et al. 2012), but may be anywhere above 50 mg/kg, but is typically greater than 150 mg/kg. Although, a single high dose mimics the rapid and near-complete destruction of beta cells, but does lack the autoimmune component of T1D. Alternatively, T1D may be induced a rodent with several low dose injections of STZ to elicit an immune and inflammatory reaction, which often leads to the destruction of beta-cells. In contrast, a single low dose of STZ (anywhere between 15-50 mg/kg) combined with high fat diet (HFD) is thought to better mimic the slow progression of beta-cell destruction in T2D associated with inflammation. Alternatively, a HFD (without low dose STZ) may be used to generate a model of T2D (see Bruin et al. 2015). Nevertheless, where the mice do not respond to HFD with increased blood glucose and weight gain, a low dose of STZ may be administered.

Numerous methods for the production of pancreatic progenitor cells for transplantation, particularly late-stage cells, are well known in the art (see for example, Rezania, A. et al. 2014; Pagliuca, F W. et al. 2014; Agulnick, A D. et al. 2015; and Russ, H A, et al. 2015).

Transplantation of hESC-Derived Pancreatic Progenitor Cells

The procedure used for transplantation of macro-encapsulated pancreatic progenitor cells was as follows. Similar transplantation of macro-encapsulated pancreatic endocrine precursor cells or insulin-producing cells was described in Rezania et al. 2014, Pagliucca et al. 2014 and Agulnick A. D. et al. 2015. All mice were anaesthetized with inhalable isoflurane and transplant recipients received ~5×10$^6$ hESC-derived pancreatic progenitor cells subcutaneously (s.c.) within a 20 1 TheraCyte™ macroencapsulation device (TheraCyte Inc.™, Laguna Hills, Calif.) on the right flank, as previously described (Bruin et al., 2013). Sham mice received the same surgical procedure, but no macroencapsulation device was implanted. In the first cohort, mice were randomly assigned to receive either a cell transplant (Tx, n=7 per diet) or sham surgery (sham, n=4 per diet) after 7 weeks of LFD or HFD feeding. In the second cohort, HFD-fed mice (+/−drug treatment) received either a transplant (n=8 per group) or sham surgery (n=8 per group) 1 week after administration of the antidiabetic drugs. LFD controls all received sham surgery. The treatment groups are summarized in TABLE 2.

TABLE 2

Summary of treatment groups for in vivo transplant (Tx) studies

| Cohort # | Diet | Drug | Tx/Sham | Sample Size |
| --- | --- | --- | --- | --- |
| 1 | 10% fat | None | Tx | 7 |
| 1 | 10% fat | None | Sham | 4 |
| 1 | 45% fat | None | Tx | 7 |
| 1 | 45% fat | None | Sham | 4 |
| 1 | 60% fat | None | Tx | 7 |
| 1 | 60% fat | None | Sham | 4 |
| 1 | Western | None | Tx | 7 |
| 1 | Western | None | Sham | 4 |
| 2 | 10% fat | None | Sham | 8 |
| 2 | 60% fat | None | Tx | 8 |
| 2 | 60% fat | None | Sham | 8 |
| 2 | 60% fat | Rosiglitazone | Tx | 8 |
| 2 | 60% fat | Rosiglitazone | Sham | 8 |
| 2 | 60% fat | Sitagliptin | Tx | 8 |
| 2 | 60% fat | Sitagliptin | Sham | 8 |
| 2 | 60% fat | Metformin | Tx | 8 |
| 2 | 60% fat | Metformin | Sham | 8 |

Metabolic Assessments

All metabolic analyses were performed in conscious, restrained mice and blood samples were collected via the saphenous vein. BW and blood glucose levels were assessed regularly throughout each study following a 4-hr morning fast. For all other metabolic tests, blood was collected after fasting (time 0) and at the indicated time points following administration of various secretagogues.

Glucose tolerance tests (GTTs) were performed following a 6-hour morning fast and administration of glucose by oral gavage or intraperitoneal (i.p.) injection (2 glucose/kg BW, 30% solution; Vétoquinol™, Lavaltrie, QC). Glucose-stimulated human C-peptide secretion from engrafted cells was assessed following an overnight fast and an i.p. injection of glucose (2 g/kg). Insulin tolerance tests (ITTs) were performed following a 4-hour morning fast and administration of human synthetic insulin (0.7 IU/kg body weight; Novolin Ge™ Toronto, Novo Nordisk™, Mississaugua, Canada). For monthly mixed-meal challenges, mice received an oral gavage of Ensure™ (8 uL/g body weight; Abbott Laboratories™, Abbott Park, Ill., USA) following an overnight fast (~16 hours). For arginine tolerance tests (ArgTT), mice received an i.p. injection of arginine (2 g/kg, 40% solution; Sigma-Aldrich™) following a 4-hour morning fast. Blood glucose levels were measured using a handheld glucometer (Lifescan™; Burnaby, Canada). Mouse hormone and lipid profiles were assessed in plasma using the following kits: leptin (Mouse Leptin ELISA, Crystal ChemInc.™, Downers Grove, Ill.), insulin (Ultrasensitive Mouse Insulin ELISA, Alpco Diagnostics™, Salem, N.H.), C-peptide (Mouse C-peptide ELISA, Alpco Diagnostics™), triglycerides (Serum Triglyceride kit, Sigma-Aldrich™), free fatty acids (NEFA-HR(2) kit, Wako Chemical™, Richmond, Va.) and cholesterol (Cholesterol E™ kit, Wako Chemical™). Hormone secretion from engrafted hESC-derived cells was assessed by measuring plasma human C-peptide (C-peptide ELISA, 80-CPTHU-E01.1; Alpco Diagnostics™) and human insulin and glucagon levels (K15160C-2; Meso Scale Discovery™, Gaithersburg, Md.). Hemoglobin A1c (HbA1c) levels were measured with a Siemens DCA 200 Vantage Analyzer™ (Siemens Healthcare Diagnostics™, Tarrytown, N.Y.) from whole blood collected from the saphenous vein with EDTA as an anticoagulant.

Dual-Energy X-Ray Absorptiometry

Body composition was determined using dual-energy X-ray absorptiometry (DEXA) with a PIXImus Mouse Densitometer™ (Inside Outside Sales™). Data are expressed as % fat.

qRT-PCR

Theracyte™ devices were harvested at 29 weeks post-transplantation from cohort 1 and stored for qPCR analysis. The qPCR analysis, human islet donors, and the procedure used to isolate RNA from engrafted tissue are described below.

Theracyte™ devices were cut in half at the time of tissue harvest and stored in RNA Later Stabilization Solution™ (Life Technologies™, Carlsbad, Calif.) at −80° C. until use. Excess mouse tissue was first removed from the outside of the device before placing the device in 2 mL PBS. The edge of the device was cut off, the outer membranes peeled back, and the device isolated and placed into 400 l Qiagen Buffer RLT Plus™ (Qiagen Inc.™, Valencia, Calif.) containing 0.1% (v/v) beta-mercaptoethanol. The PBS was collected and centrifuged at 2000×g for 4 min to collect any cells that spilled out of the device. The cell pellet was resuspended in the same RLT Plus buffer used for lysing the corresponding device. RNA was isolated using Qiagen RNeasy Plus Mini™ kit (Qiagen Inc.™) and eluted in 16 l nuclease-free water. RNA concentration was measured using the NanoDrop8000 (Thermo Scientific™). Human islets were obtained from four organ donors (23-48 years of age; two males and two females) as a positive control for qPCR analysis (ProdoLabs™, Irvine, Calif.). Islet purity ranged from 85-95% and viability from 90-95%. All human islet preparations showed a 2 to 4-fold increase in human insulin secretion after incubation with high glucose concentration (data not shown) using a static glucose-stimulated insulin secretion assay, as previously described (Rezania et al., 2014).

Due to a low amount of human cells/tissue in the device, and the high probability that some of the RNA would be from the surrounding mouse tissue, the amount of human RNA was measured using a standard curve. First, all RNA was converted into cDNA using the High Capacity cDNA Reverse Transcription™ kit (Thermo Fisher Scientific™/Life Technologies™) with the following program: 25° C. for 10 minutes, 37° C. for 2 hours, 4° C. hold. Pre-amplification was performed using a primer pool specific for the genes run (TABLE 3) and TaqMan PreAmp™ 2× Master Mix (Thermo Fisher Scientific™/Life Technologies™) with the following cycling conditions: 95° C. 10 min, 8 cycles of 95° C. 15 s and 60° C. 4 min, 99° C. 10 min, and 4° C. hold. To determine the amount of human cDNA, real-time PCR was performed on the Pre-amplified cDNA using primers specific to human GAPDH and mouse Gapdh and run against a standard curve made from known amounts of cDNA from a human cell line. Sixteen ng of calculated human cDNA was run on a custom TaqMan Low Density Array™ (Thermo Fisher Scientific™/Life Technologies™; TABLE 3) using the Quant Studio 12K Flex Real Time PCR™ instrument (Thermo Fisher Scientific™/Life Technologies™). Data were analyzed using Expression Suite™ software (v1.0.3, Thermo Fisher Scientific"/Life Technologies") and normalized to undifferentiated H1 cells using the delta delta Ct method. Immunofluorescent staining and image quantification to measure endogenous pancreatic beta and alpha cell area three pancreas sections per animal, separated by at least 200 m, were immunostained for insulin and glucagon. Whole slide fluorescence scanning was performed using the Image Xpress Micro TM Imaging System™, and images were stitched together and analyzed using MetaXpress Software™ (Molecular Devices Corporation™, Sunnyvale, Calif.). The beta cell or alpha cell fraction was calculated as the insulin-positive or glucagon-positive area/total pancreas area and the average of three sections per animal was then multiplied by the pancreas weight. To quantify the endocrine composition within devices, the number of DAPI-positive nuclei were counted using the Multi Wavelength Cell Scoring™ n or both hormones was counted manually by an investigator who was blinded to the treatment groups. Primers are listed in TABLE 3.

TABLE 3

List of qPCR primers

| Gene Name | Assay ID |
| --- | --- |
| ABCC8 | Hs00165861_m1 |
| CHGB | Hs01084631_m1 |
| G6PC2 | Hs01549773_m1 |
| GAPDH | Hs99999905_m1 |
| GCG | Hs00174967_m1 |
| GCGR | Hs01026191_g1 |
| IAPP | Hs00169095_m1 |
| INS | Hs00355773_m1 |
| ISL1 | Hs00158126_m1 |
| MAFA | Hs01651425_s1 |
| NKX6.1 | Hs00232355_m1 |
| PAX6 | Hs00240871_m1 |
| PCSK1 | Hs00175619_m1 |
| PCSK2 | Hs01037347_m1 |
| SLC30A8 | Hs00545183_m1 |
| SST | Hs00356144_m1 |
| UCN3 | Hs00846499_s1 |

Immunofluorescent Staining and Image Quantification

Prior to transplantation, a portion of differentiated pancreatic progenitor cells were fixed overnight in 4% paraformaldehyde (PFA) and then embedded in 1% agarose prior to paraffin embedding. In cohort 1, the Theractye™ devices and a variety of tissues (Adipose Tissue, Perirenal; Ileum; Skeletal Muscle; Cecum; Jejunum; Spleen; Colon; Kidney; Stomach, Glandular; Duodenum; Liver; Stomach, Nonglandular; Heart; Lung; and Testis) were harvested at 29 weeks post-transplantation, fixed in 4% PFA, and stored in 70% EtOH prior to paraffin embedding. All paraffin sections (5 mm thick) were prepared by Wax-it Histology Services™. Immunofluorescent staining was performed as previously described (Rezania et al., 2011) and details about the primary antibodies are provided in TABLE 4. H&E staining was performed according to standard procedures and tissue analysis was performed in a blinded fashion by an independent pathologist (Nova Pathology PC™).

TABLE 4

Antibody information for immunofluorescent staining

| Antigen | Species | Source | Dilution |
| --- | --- | --- | --- |
| CK19 | Mouse | Dako ™; Denmark | 1:100 |
| C-Peptide | Guinea Pig | Abcam ™; Cambridge, MA | 1:100 |
| F4/80 | Rat | AbD Serotec ™; Kidlington, UK | 1:100 |
| FGF21 | Rabbit | Abcam ™; Cambridge, MA | 1:50 |
| Glucagon (Ms) | Mouse | Sigma-Aldrich ™; St Louis, MO | 1:1000 |
| Glucagon (Rb) | Rabbit | Cell Signaling ™; Danvers, MA | 1:500 |
| Insulin (GP) | Guinea Pig | Sigma-Aldrich ™; St Louis, MO | 1:1000 |
| Insulin (Rb) | Rabbit | Cell Signaling ™; Danvers, MA | 1:100 |
| Insulin (MAb1) | Mouse | Millipore ™; Billerica, MA | 1:200 |
| MAFA | Rabbit | Custom Antibody; Lifespan Biosciences ™; Seattle, WA | 1:1000 |
| NKX6.1 | Rabbit | Custom Antibody; Lifespan Biosciences ™; Seattle, WA | 1:1000 |
| NKX2.2 | Mouse | Developmental Studies Hybridoma Bank ™; University of Iowa; Iowa City, IA | 1:100 |
| PAX6 | Rabbit | Covance ™; Princeton, NJ | 1:250 |
| PCNA | Mouse | BD Biosciences ™; Mississauga, ON | 1:100 |
| PDX1 | Guinea Pig | Abcam ™; Cambridge, MA | 1:1000 |
| Somatostatin (Ms) | Mouse | Sigma-Aldrich ™; St Louis, MO | 1:100 |
| Somatostatin (Rb) | Rabbit | Sigma-Aldrich ™; St Louis, MO | 1:500 |
| Synaptophysin | Rabbit | Novus Biologicals ™; Littleton, CO | 1:50 |
| Trypsin | Sheep | R&D Systems ™; Minneapolis, MN | 1:100 |

Statistical Analysis

All statistical analyses were performed using GraphPad Prism™ software (GraphPad Software). Two-way repeated measure ANOVAs were performed with a Fisher's LSD post-hoc test to compare HFD mice with LFD controls at different time points. One-way repeated measures ANOVA were performed with Dunnett post-hoc to compare values at different time points to baseline levels (time 0) within each treatment group. One-way ANOVAs were performed with a Dunnett post-hoc test for multiple comparisons to 10% fat controls or a Student-Neuman-Keuls test to compare between multiple groups. The qPCR data was assessed by one-way ANOVA with a Fisher's LSD post-hoc test to compare grafts from various treatment groups with either human islets or HFD-fed mice without drug treatment. Unpaired t-tests were used to compare the effect of transplantation within a single treatment group (i.e. sham vs tx) and paired t-tests were used when comparing samples pre- and post-administration of a insulin or glucagon secretogogue (oral meal, arginine). Area under the curve was calculated with y=0 as the baseline. For ITTs, area above the curve was calculated using the fasting blood glucose level for each animal as the baseline. For all analyses, $p<0.05$ was considered statistically significant. Data are presented as the mean±SEM (line graphs) or as box-and-whisker plots showing individual data points.

Cell Preparation for SH-1533: Advance Differentiation of S4D4 IDP to Advance Day 9

S4D4 IDP cells were thawed into each of two 500 ml PBS-MINI vertical spinners with 400 ml Stage 5 thaw media per spinner. To ensure adequate dilution of DMSO in the cell suspension, while cells were settled on, the bottom of the vial, approximately 3 ml of cryopreservation media was aspirated from each vial prior to transfer of the cells to the PBS-MINI spinner. Subsequently, thaw media was added drop wise to the spinner to dilute the population. The thaw media consisted of DMEM-HG media supplemented with 2% KSR, 1:200 ITS-X, 10 ug/ml Heparin, 100 nM LDN, 1 uM T3, 5 uM ALK5i, 250 nM SANT-1, 50 nM RA, 10 uM Y-27632, and 4 ku/ml DNase. Each vessel was placed on a PBS-MINI base in the BSC set to 25 RPM and 2×5 ml samples were pulled for cell counts using the accutase count method and the NC100 NucleoCounter. The vessels were then cultured overnight in a 37° C. 5% CO2 incubator on a PBS-MINI base set to 20 RPM.

Following overnight culture each vessel containing cells was placed in the BSC for ~5-10 minutes to allow cells to settle to the bottom of the spinner. The majority of the spent culture media was aspirated from the vessel and fresh Stage 5 media containing DMEM-HG media supplemented with 2% KSR, 1:200 ITS-X, 10 ug/ml Heparin, 100 nM LDN, 1 uM T3, 5 uM ALK5i, 250 nM SANT-1, and 50 nM RA. Each vessel was placed on a PBS-MINI base in the BSC set to 25 RPM and 2×5 ml samples were pulled for cell counts using the accutase count method and the NC100 NucleoCounter. The cultures were then again cultured overnight as described above except that the speed of the base was increased to 22 RPM to help decrease clumping of clusters.

On the third day of culture, the media was changed to Stage 6 media containing all Stage 5 components plus the addition of 100 nM gamma secretase inhibitor (XX). The culture continued with daily stage 6 media exchanges until S6D7 complete at which time the cells were transferred to a perfusion spinner for washing and aliquoting. Cells were aliquoted into 5 million cells/aliquot using the sampling port on the spinner flask and a 10 cc syringe and then transferred to a 1.5 ml centrifuge tube for kidney capsule transplant. Kidney capsule aliquots were transferred immediately to the transplant site via courier at ambient temperature in a DMEM-HG basal media supplemented with 2% KSR, 1:200 ITS-X, and 10 ug/ml Heparin. A biomarker expression check was done on the cell population at S6D7 via FACS, PCR, IHC, and phase contrast imaging. Sterility samples were collected from the reagents and the residual media from all kidney capsule aliquots prior to transplantation.

Figure 12A:
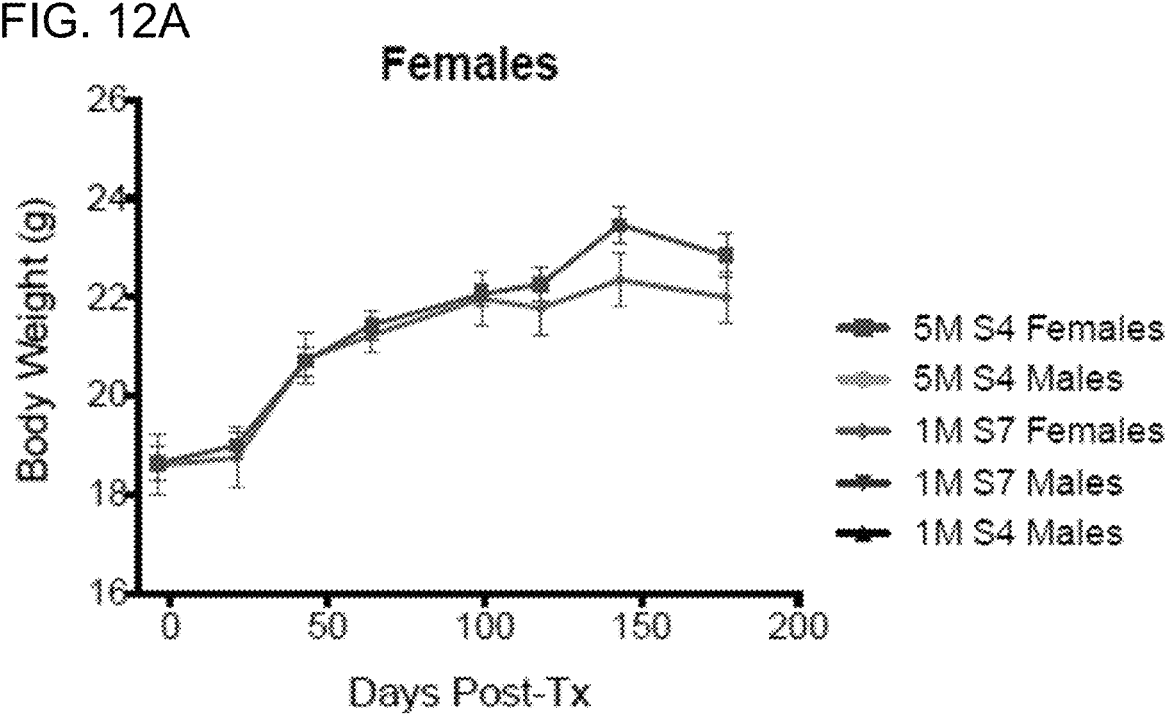
FIGS. 12A and 12B show two graphs of body weight in grams plotted against time post transplant in days for female (12A) and male (12B) mice, wherein 1M=1 million, 5M=5 million, S4=Stage 4 cells and S7=Stage 7 cells. Mice were weighted about 4 days before transplant and about every 2-4 weeks after the transplant following a 4 hour fast (usually 7 am-11 am) and zero (0) is the day of the transplant.
Figure 12B:
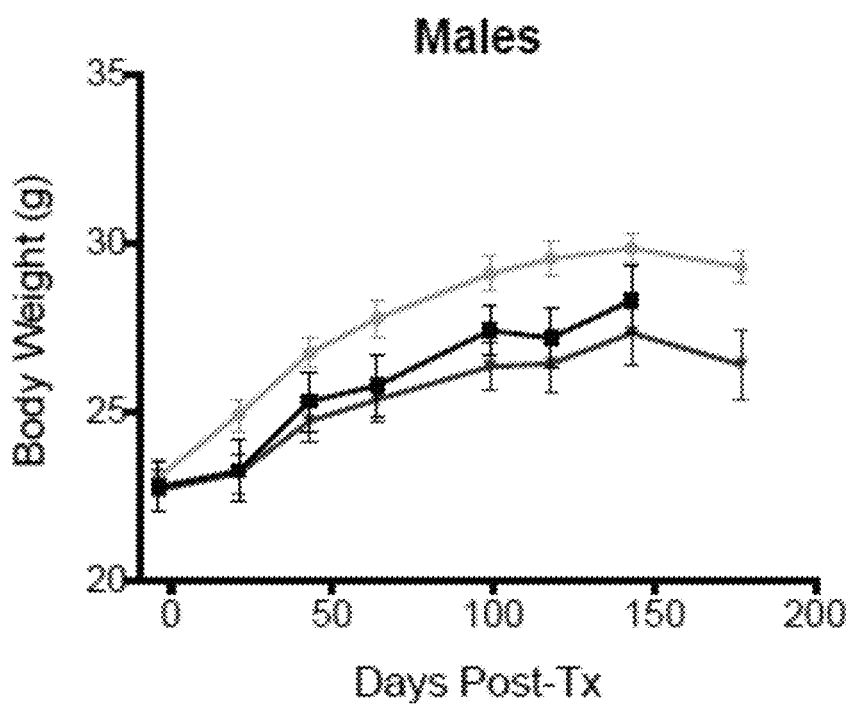
Figure 13A:
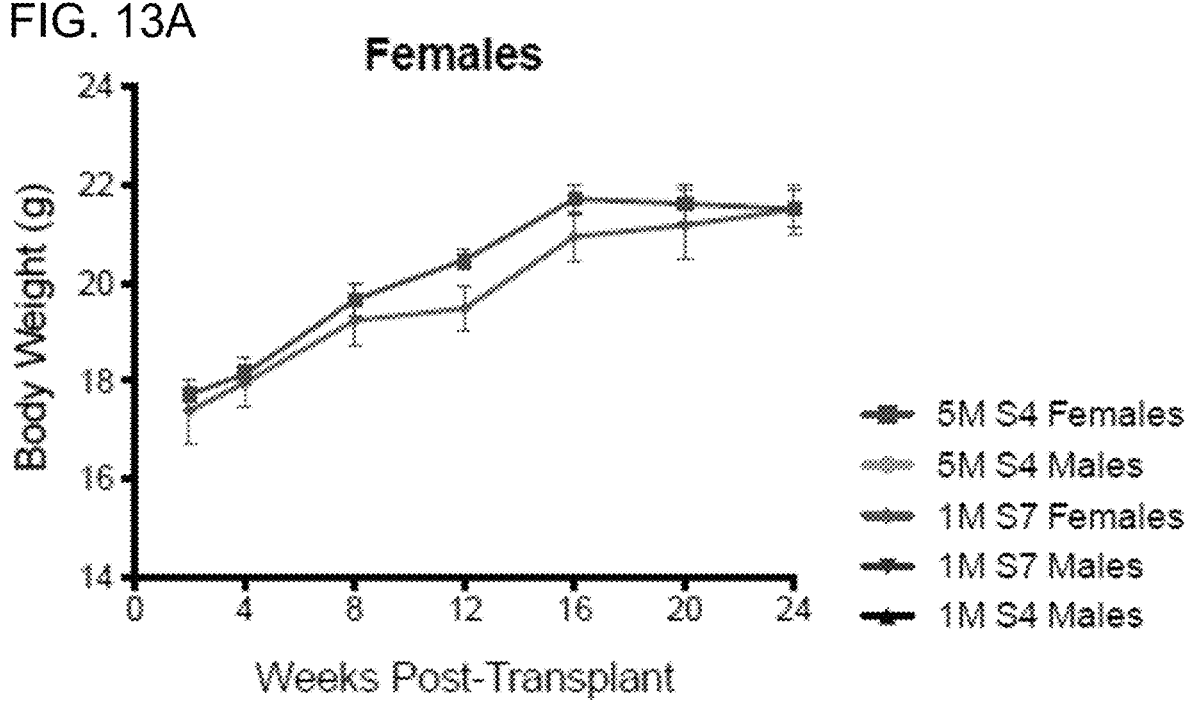
FIGS. 13A and 13B show two graphs of body weight in grams plotted against time post transplant in weeks for female (13A) and male (13B) mice, wherein 1M=1 million, 5M=5 million, S4=Stage 4 cells and S7=Stage 7 cells. Mice were weighted at 2, 4, 8, 12, 16, 20 and 24 weeks post-transplant following an overnight fast (usually 5 pm-8 am~15 hrs.) and zero (0) is the day of the transplant.
Figure 13B:
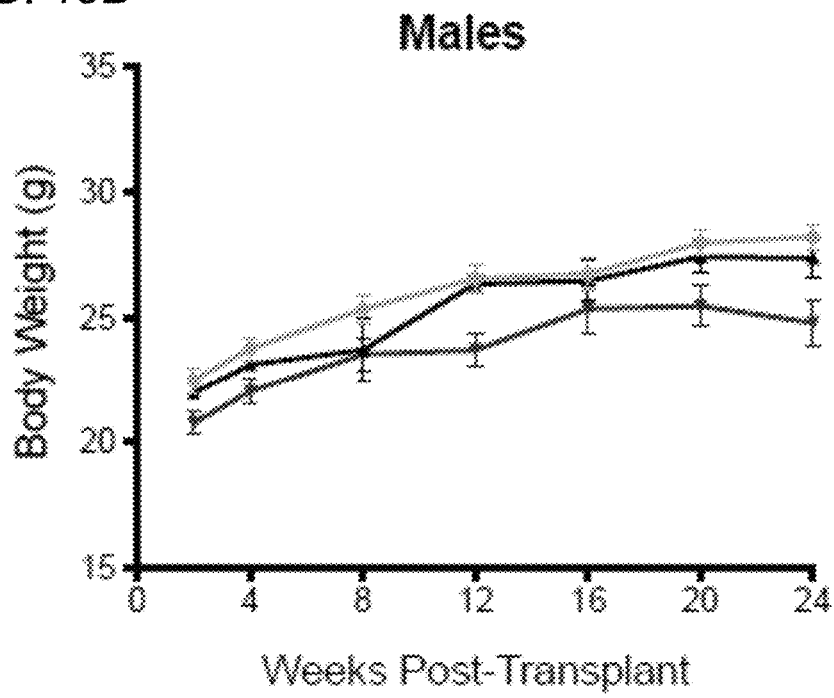

FIGS. 12, 13—Male and female SCID-Beige mice (C.B-Igh-1b/GbmsTac-Prkdc$^{scid}$-Lyst$^{bg}$N7; Taconic, Hudson, N.Y.) received ad libitum access to a standard irradiated diet (Teklad Diet #2918—Harlan Laboratories, Madison, Wis., USA) and were maintained on a 12 h light/dark cycle throughout the study. At 7 weeks old, all mice were anaesthetized with inhalable isoflurane and transplant recipients received either ~5×10$^6$ stage 4 cells (5M S4), ~1×10$^6$ stage 4 cells (1M S4), or ~1×10$^6$ stage 7 cells (1M S7) under the kidney capsule on the left flank: 5M S4 females (N=10), 5M S4 males (N=11), 1M S4 males (N=5), 1M S7 females (N=9), 1M S7 males (N=9). Differentiated human ES cells were produced using the methods described in Rezania, A. et al. 2014. Body weight was assessed bi-weekly or monthly throughout the study following a 4-hour morning fast.

FIG. 14—Six week old immunocompromised SCID Beige mice were acclimatized for 1 week post arrival. Animals were then injected with a single dose of 190 mg/kg of the beta-cell toxin streptozotocin (STZ) to induce a model of type 1 diabetes. 1.5 Million Stage 7 cells produced using the methods described in Rezania, A. et al. 2014, or ~6000 isolated human islet equivalents (IEQs) were transplanted under the kidney capsule. Control mice received neither STZ nor cell transplants. Mice were subsequently monitored weekly for 4 h fasting blood glucose levels and body weight. Human islet recipient mice consisted of mice that had previously been injected with STZ but returned to normoglycemia, except for one animal that was hyperglycemic, in addition to non-STZ treated mice.

Figure 15A:
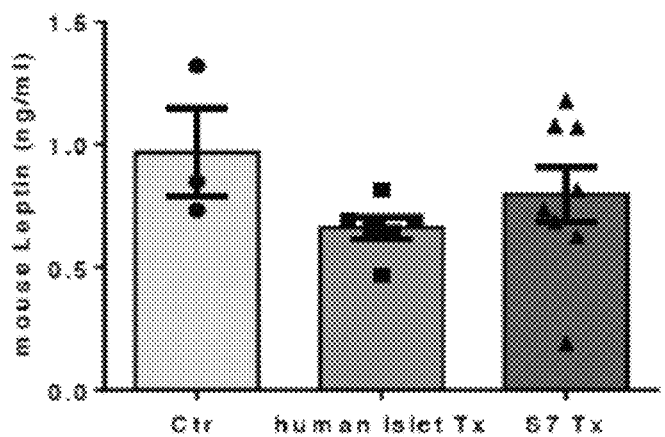
FIGS. 15A-15C show three graphs comparing control mice to mice transplanted with Stage 7 cells (S7) and mice transplanted with human islet cells (same mice from FIG. 14), where (15A) mouse Leptin (ng/ml) was measured in random fed mice, (15B) fat mass (g) from dual-energy X-ray absorptiometry (DEXA) and (15C) mouse Leptin (ng/ml) in random fed mice divided by grams of fat.

FIG. 15A—Blood for glucose measurements and sampling were from the saphenous vein of conscious restrained mice. For hormone detection blood was collected in heparinized capillaries, transferred on ice into 1.5 ml tubes and the plasma separated from blood cells after a 9 min spin at 7000 rpm. Samples were stored at −30° C. before assaying for leptin by ELISA.

FIGS. 15B to 17—Body composition of mice was measured on the day following metabolic cage analysis via dual energy X-ray absorptiometry (DEXA) measurements on isoflurane anesthetized mice. Fat pad and organ weights were determined by dissection and immediate weighing of tissues.

Figure 18A:
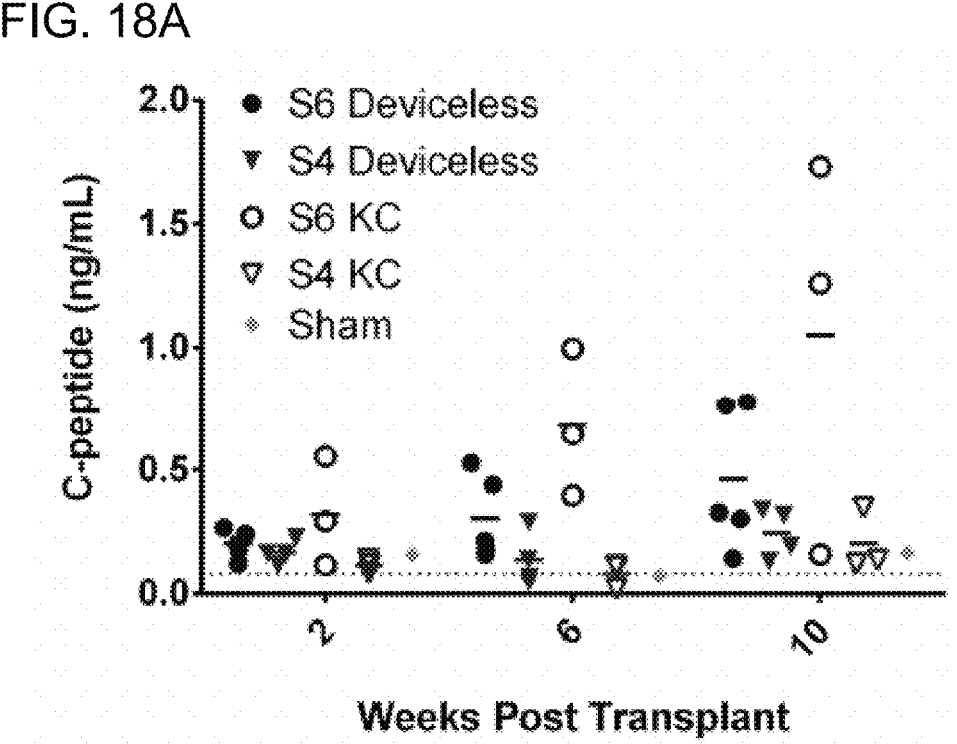
FIGS. 18A-18C show 3 graphs comparing Stage 4 and Stage 6 cell transplants to control mice (no cell transplant—sham operation) in subcutaneous deviceless and kidney capsule (KC) implanted mice showing C-peptide ng/ml (18A); body weight (18B); and weekly fasting blood glucose (18C).

FIG. 18—To differentiate cryostored Stage 4 cells to Stage 6 cells, cells were thawed into each of two 500 ml PBS-MINI vertical spinners with 400 ml Stage 5 thaw media per spinner. To ensure adequate dilution of DMSO in the cell suspension, while cells were settled on the bottom of the vial, approximately 3 ml of cryopreservation media was aspirated from each vial prior to transfer of the cells to the PBS-MINI spinner. Subsequently, thaw media was added drop wise to the spinner to dilute the population. The thaw media consisted of DMEM-HG media supplemented with 2% KSR, 1:200 ITS-X, 10 µg/ml Heparin, 100 nM LDN, 1 µM T3, 5 µM ALK5i, 250 nM SANT-1, 50 nM RA, 10 µM Y-27632, and 4 ku/ml DNase. Each vessel was placed on a PBS-MINI base in the BSC set to 25 RPM and 2×5 ml samples were pulled for cell counts using the accutase count method and the NC100 NucleoCounter. The vessels were then cultured overnight in a 37° C. 5% CO2 incubator on a PBS-MINI base set to 20 RPM. Following overnight culture each vessel containing cells was placed in the BSC for ~5-10 minutes to allow cells to settle to the bottom of the spinner. The majority of the spent culture media was aspirated from the vessel and fresh Stage 5 media containing DMEM-HG media supplemented with 2% KSR, 1:200 ITS-X, 10 µg/ml Heparin, 100 nM LDN, 1 µM T3, 5 µM ALK5i, 250 nM SANT-1, and 50 nM RA. Each vessel was placed on a PBS-MINI base in the BSC set to 25 RPM and 2×5 ml samples were pulled for cell counts using the accutase count method and the NC100 NucleoCounter. The cultures were then again cultured overnight as described above except that the speed of the base was increased to 22 RPM to help decrease clumping of clusters. On the third day of culture, the media was changed to Stage 6 media containing all Stage 5 components plus the addition of 100 nM gamma secretase inhibitor (XX). The culture continued with daily stage 6 media exchanges until S6D7 complete at which time the cells were transferred to a perfusion spinner for washing and aliquoting. Cells were aliquoted for transplant.

Cell transplants were either under the kidney capsule or in a subcutaneous deviceless pocket as described by Pepper, A R. et al. 2015 Specifically 4 weeks before cell transplant, 2-cm segments of a 5-French (Fr.) textured nylon radiopaque angiographic catheter were implanted subcutaneously into the lower left quadrant of SCID Beige mice. A 4-mm lateral transverse incision was made caudal to the rib cage allowing for a small pocket to be created inferior to the incision line using blunt dissection. An adequate void (1 cm by 3 cm) was created. The catheter segment was implanted into the space such that the catheter laid parallel to the midline. The incision was sutured closed. Once implanted, the catheter became adherent with blood proteins, leading to the formation of densely vascularized tissue, which exhibited a minimally visible profile. At the time of transplant, removal of the catheter revealed a vascularized lumen allowing for cellular transplant infusion.

Deviceless-recipient mice were maintained under anesthesia with inhalant isoflurane and placed in a supine position. A field surrounding the implanted catheter was prepared by shaving and disinfecting the surface. Cranial to the superior edge of the implanted catheter, a small (4 mm) incision was made to gain access to the catheter. The tissue matrix surrounding the superior margin of the catheter was dissected to withdraw and remove the catheter. The cells were then delivered into the space using a pipette tip. The incision was sutured closed. Prior to recovery, recipients received a 0.1 mg/kg subcutaneous bolus of buprenorphine.

Control animals received the same dose of cells under the kidney capsule, the standard site for rodent islet transplantation. For all experiments cells were pooled, batched and transplanted in random allocation to either the DL or KC sites. To facilitate the KC transplants, a left lateral paralumbar subcostal incision was made and the left kidney was delivered into the wound. The renal capsule was incised and space was made under the capsule to allow transplantation of the cells using PE-50 tubing. The subcostal incision was closed in two layers.

Animals were monitored at regular intervals for body weight, and 4 hour fasting glycemia. Blood was collected from the saphenous vein of random fed mice 2, 6 and 10 weeks post transplant and plasma was assayed for human C-peptide by ELISA (Alpco).

The invention will be further clarified by a consideration of the following, non-limiting examples.

EXAMPLES

All metabolic analyses used in these Examples were performed using blood samples collected via saphenous vein. Body weight and blood glucose levels were assessed regularly throughout each study following a 4-hour morning fast. For all other metabolic tests, blood was collected after fasting (time zero) and at the indicated time points following administration of various secretagogues. Body composition was determined using dual-energy X-ray absorptiometry ("DEXA") with a PIXImus Mouse Densitometer™ (Inside Outside Sales™, Madison, Wis.). Data are expressed as % fat.

Example 1: Development of a Model of Obesity and Type 2 Diabetes (T2D) in Immunodeficient Mice For purposes of carrying out the examples, 8 to 10 week old male, SCID-beige mice (C.B-Igh-1b/GbmsTac- Prkdc$^{scid}$-Lyst$^{bg}$N7; Taconic™, Hudson, N.Y.) were maintained on a 12 hour light/dark cycle. All mice received ad libitum access to a standard irradiated diet (Harlan Laboratories™, Teklad Diet™ #2918, Madison, Wis.) for 2 weeks to allow for acclimatization. Mice were placed on one of four different diet regimens (Research Diets™, New Brunswick, N.J., USA) for the 36 week study (n=11 per diet): 1) "10% fat" control diet (D12450K—10 kcal % fat; 70 kcal % carbohydrate, no sucrose); 2) "45% fat" diet (D12451—45 kcal % fat, primarily lard; 35 kcal % carbohydrate); 3) "60% fat" diet (D12492—60 kcal % fat, primarily lard; 20 kcal % carbohydrate); or 4) "western" diet (D12079B—41 kcal % fat, primarily milk fat; 43 kcal % carbohydrate, primarily sucrose).

Blood glucose levels were measured using a handheld glucometer (Lifescan™, Milpitas, Calif.). Mouse hormone and lipid profiles were assessed in plasma using the following kits: leptin (Mouse Leptin ELISA, Crystal Chem Inc.™, Downers Grove, Ill.), insulin (Ultrasensitive Mouse Insulin ELISA, Alpco Diagnostics™, Salem, N.H.), C-peptide (Mouse C-peptide ELISA, Alpco Diagnostics™), triglycerides (Serum Triglyceride™ kit, Sigma-Aldrich™), free fatty acids (NEFA-HR(2) kit, Wako Chemical™, Richmond, Va.) and cholesterol (Cholesterol E Kit™, Wako Chemical™). Hormone secretion from engrafted hESC-derived cells was assessed by measuring plasma human C-peptide (C-peptide ELISA, 80-CPTHU-E01.1; Alpco Diagnostics™) and human insulin and glucagon levels (K15160C-2; Meso Scale Discovery™, Gaithersburg, Md.). Hemoglobin A1c (HbA1c) levels were measured with a Siemens DCA 200 Vantage Analyzer™ (Siemens Healthcare Diagnostics™, Tarrytown, N.Y.) from whole blood collected from the saphenous vein with EDTA as an anticoagulant.

FIG. 1 and FIG. 7 display body weight gain, measures of glucose homeostasis and adipocyte characterization in mice on the various diets. All three high fat diets (HFD; 45% fat, 60% fat, and western) induced rapid increases in fasting body weight (FIG. 1A) and blood glucose levels (FIG. 1B) compared to low fat diet (LFD) controls (10% fat). Moreover, after five days, mice in all three HFD groups were severely glucose intolerant relative to LFD controls (FIG. 7A), prior to differences in body weight (FIG. 7B). At 32 days, HFD mice were both glucose intolerant (FIG. 7C) and significantly heavier (FIG. 7D) than LFD controls. Mice fed 45% and 60% fat diets were overtly insulin resistant at day 42 (higher glucose levels at 10 and 60-120 minutes post-insulin, and reduced area above the curve relative to LFD controls), whereas Western diet mice only showed significant insulin resistance at 10 minutes after insulin administration (FIG. 1E).

Figure 1D:
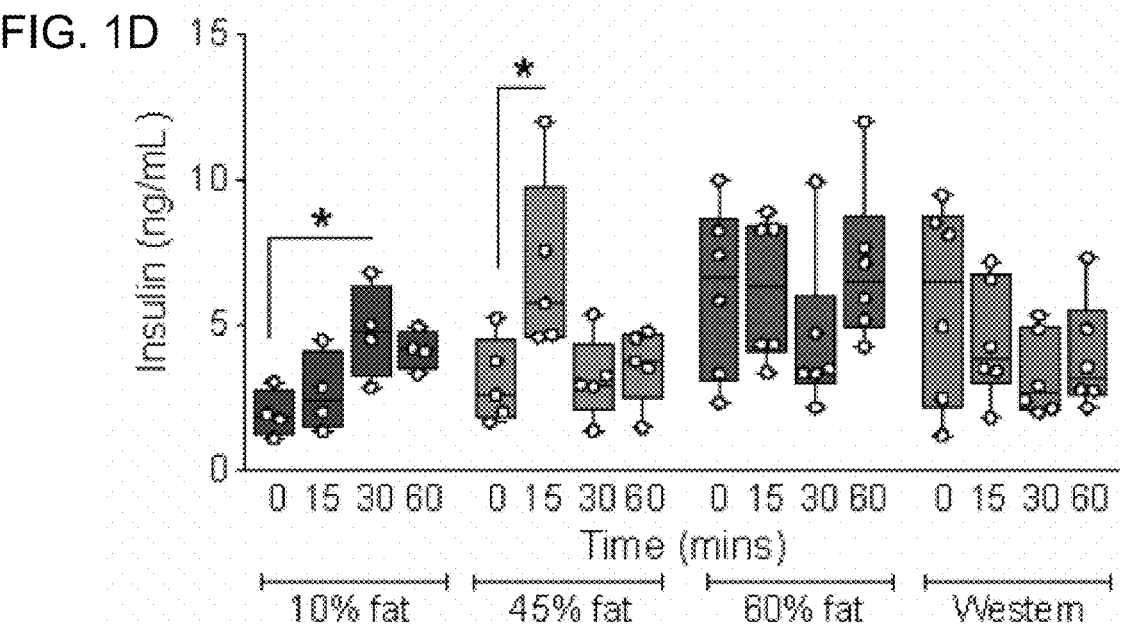
FIG. 1D shows a graph of the insulin levels of the Example 1 mice in samples collected during the oral glucose challenge at Day 47.
Figure 1E:
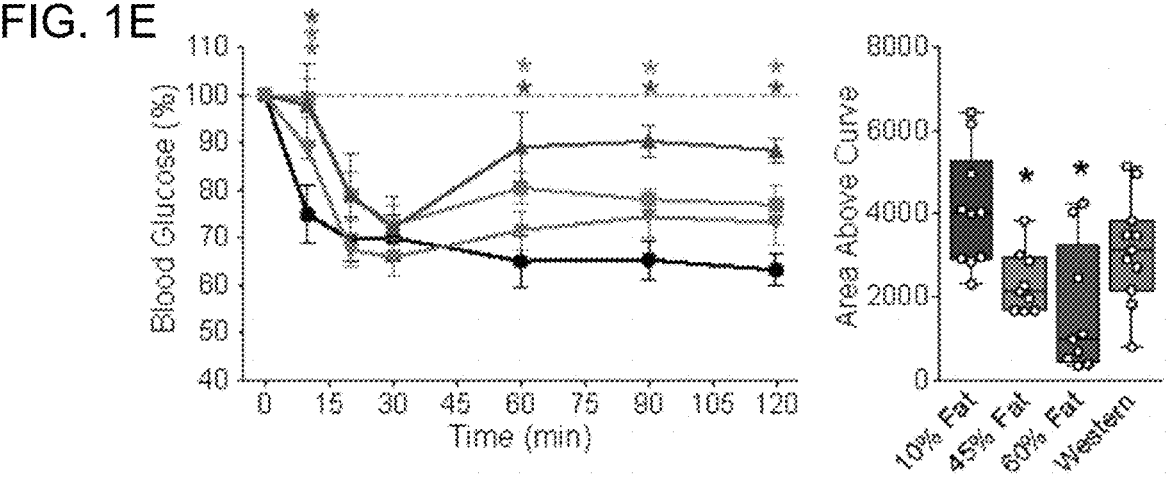
FIG. 1E shows a graph of the results of an insulin tolerance test performed at Day 42 on the mice of Example 1.
Figure 1F:
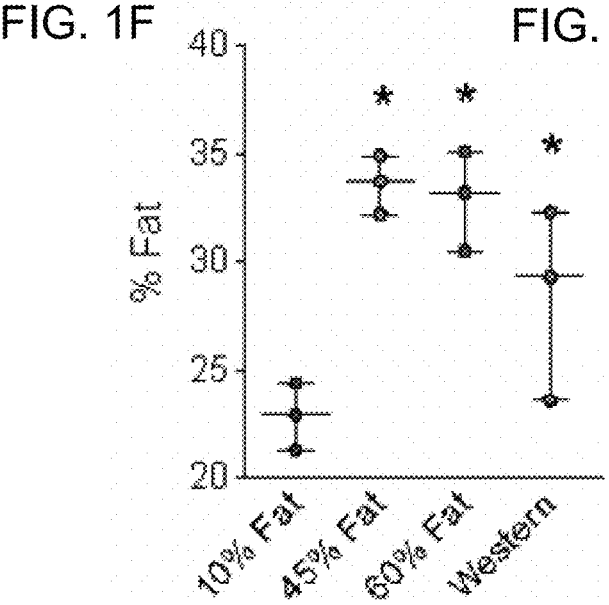
FIG. 1F shows the results of dual-energy X-ray absorptiometry (DEXA) assessment of recent fat of a subset of the mice of Example 1 at Day 43.
Figure 1G:
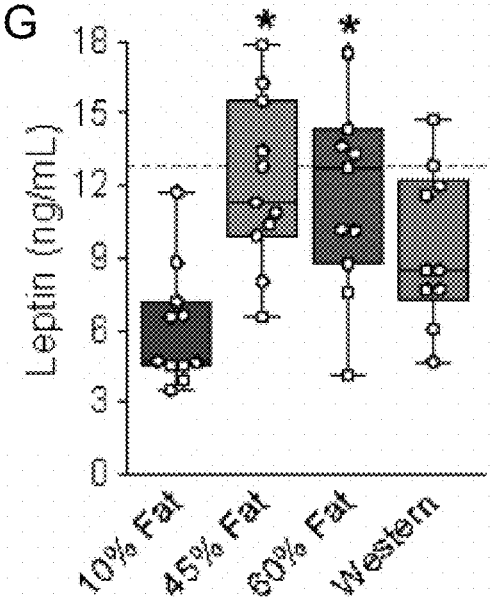
FIG. 1G shows the leptin levels measured at days 47 through 49 and after a four to six hour morning fast of the mice of Example 1.
Figure 7A:
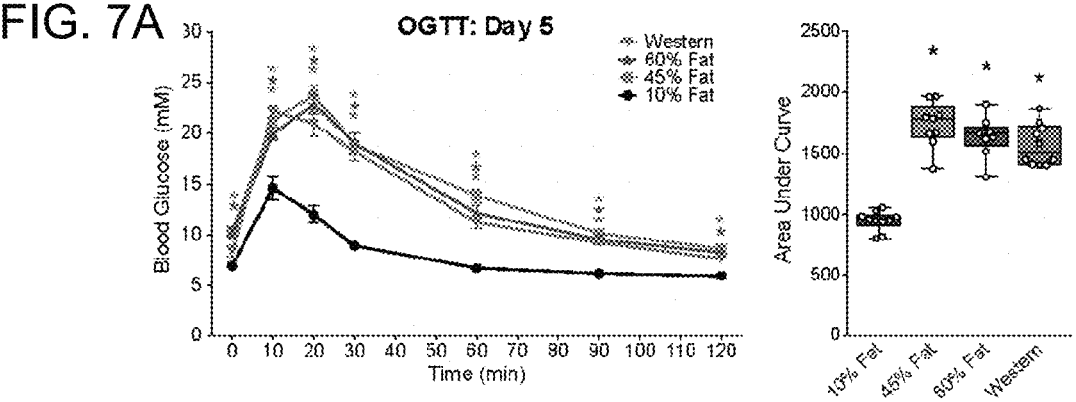
FIGS. 7A and 7C show graphs of the results of oral glucose tolerance tests at day 5 (7A) and day 32 (7C) after administration of the diets of Example 1 to the mice (these are additional time points that go with FIG. 1).
Figure 7B:
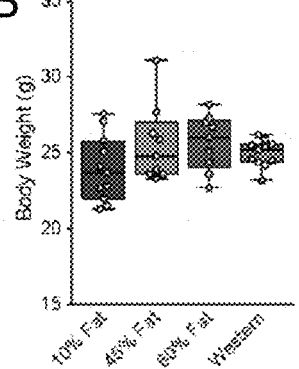
FIGS. 7B and 7D show graphs of the body weight of the Example 1 mice at day 5 (7B) and day 32 (7D).
Figure 7C:
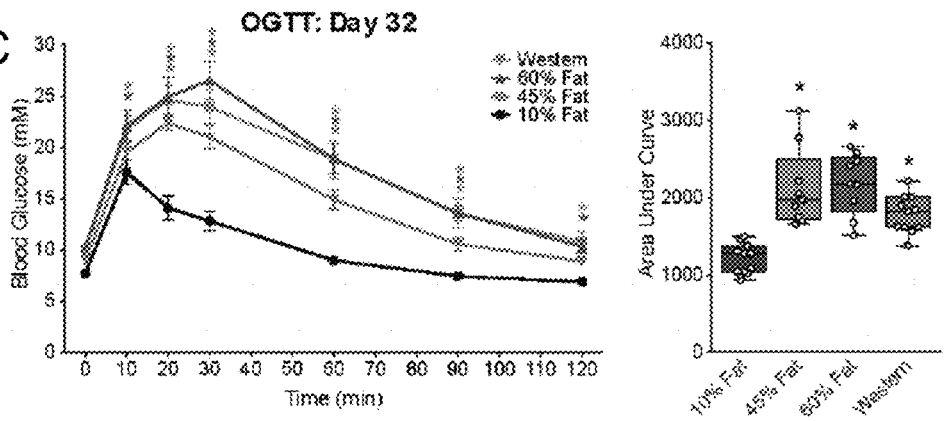
Figure 7D:
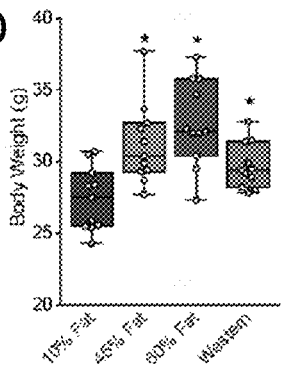
Figure 7E:
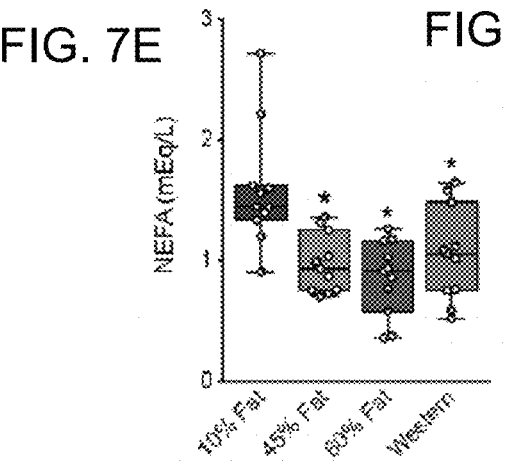
FIGS. 7E, 7F, and 7G show plasma levels, following a four to six hour morning fast, in the Example 1 mice between days 47 and 49. 7E is a graph of free fatty acids, 7F is a graph of triglycerides and 7G is a graph of cholesterol.
Figure 7F:
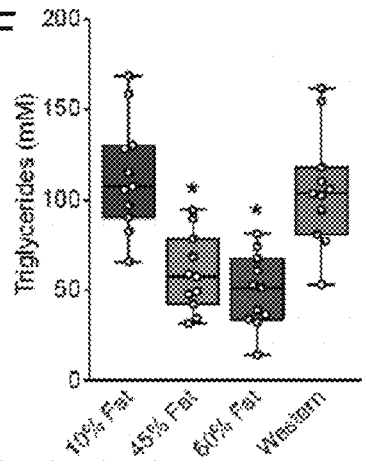
Figure 7G:
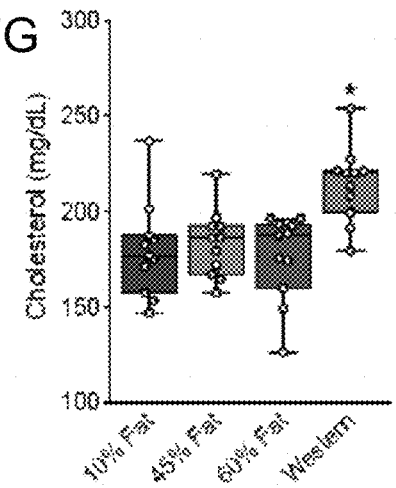

Mice in all HFD groups developed glucose intolerance (day 47, FIG. 1C) and had insulin secretion kinetics that differed from LFD controls (either no glucose-induced insulin secretion or altered timing of peak insulin levels; FIG. 1D). All HFD mice were significantly overweight (FIG. 1A) and had increased adiposity (FIG. 1F) compared to LFD controls; mice fed 45% and 60% fat diets also had significantly elevated circulating leptin levels (FIG. 1G). Exposure to HFDs caused dyslipidemia, including significantly reduced plasma free fatty acid levels in all HFD-fed mice (FIG. 7E), reduced triglyceride levels in 45% and 60% fat groups (FIG. 7F), and elevated cholesterol levels in the western diet group compared to LFD controls (FIG. 7G). The HFD-induced metabolic defects in immune-deficient mice were not associated with macrophage infiltration in adipose tissue (marked by F4/80 immuno-reactivity, whereas significant accumulation of F4/80-positive crown-like structures were observed in the epididymal fat of ob/ob mice, an immunocompetent model of T2D (micrographs not shown). The immuno-fluorescent staining of epididymal fat from the mice of Example 1 fed either 10% or 60% fat diets for 36 weeks and of an ob/ob mouse was carried out, wherein F4/80 and FGF21 are, respectively, a macrophage and an adipocyte markers.

Example 2: In Vitro Generation of Pancreatic Endocrine Progenitor Cells from Human Embryonic Stem Cells Cells of the human embryonic stem cell line H1 (WA01 cells, WiCell Research Institute™, Madison, Wis.) were seeded as single cells at 1×10$^5$ cells/cm$^2$ on 1:30 diluted MATRIGEL™ (Becton Dickinson BioSciences™, Franklin Lakes, N.J.; Catalogue ("Cat.") No. 356231) coated dishes in mTeSR-1™ (Stem Cell Technologies™, Vancouver, BC; Cat. no. 05850). At ~70-80% confluency, the H1 cell cultures were rinsed with 1× Dulbeccos's phosphate buffered saline without Mg2+ and Ca2+(Invitrogen™, Carlsbad, Calif.; Cat. No. 14190) followed by incubation with 0.02% Versene™ ("EDTA") (Lonza™, Walkersville, Md.; Cat. No. 17-711E) for 12 mins at room temperature. Released single cells were rinsed with mTeSR-1™, and spun at 1000 rpm for 5 mins. The resulting cell pellet was re-suspended in mTeSR-1™ medium supplemented with 10 μM of the ROCK inhibitor Y-27632™ (Sigma-Aldrich™, St. Louis Mo.; Cat. No. Y0503) and the single cell suspension was seeded at approximately 1.3×10$^5$ cells/cm$^2$. Cultures were fed every day and differentiation was initiated 48 hrs following seeding, resulting in ~90% starting confluency. The cultures were differentiated using the following protocol.

Stage 1 (3 days): Undifferentiated H1 cells plated on MATRIGEL™ coated surfaces (90% confluent) were exposed to RPMI 1640™ medium (Invitrogen™, Cat. No. 22400) supplemented with 1.2 g/L sodium bicarbonate (Sigma-Aldrich™, Cat. No. S6297), 0.2% fetal bovine serum ("FBS") (Hyclone™, South Logan, Utah; Cat. No. SH30071.02), 100 ng/mL activin-A ("AA") (Peprotech™, Rocky Hill, N.J.; Cat. No. 338-AC-010), and 20 ng/mL of Wnt3A (R&D Systems, Inc.™, Minneapolis, Minn.; Cat. No. 5036-WN) for day one only. For the next two days, cells were cultured in RPMI with 0.5% FBS, 1.2 g/L sodium bicarbonate, and 100 ng/mL AA.

Stage 2 (3 days): Stage 1 cells were cultured in DMEM-F12 medium (Invitrogen™ (Gibco™); Cat. No. 10565-018) supplemented with 2 g/L sodium bicarbonate, 2% FBS and 50 ng/mL of FGF7 (Peprotech™, Cat. No. 100-19) for three days.

Stage 3 (4 days): Stage 2 cells were cultured in DMEM-HG (high glucose) medium (Invitrogen™. Cat. No. 10569-044) supplemented with 0.25 μM SANT-1 (N-[(3,5-dimethyl-1-phenyl-1H-pyrazol-4-yl)methylene]-4-(phenylmethyl)-1-piperazineamine) (Sigma-Aldrich™, Cat. No. S4572), 2 μM retinoic acid ("RA") (Sigma-Aldrich™, Catalog No. R2625), 100 ng/mL of Noggin™ (R&D Systems™, Cat. No. 6057-NG), and 1% (v/v) B27 (Invitrogen™ (Gibco™), Cat. No. 17504-044).

Stage 4 (5 days): Stage 3 cells were cultured for 4 days in DMEM-HG medium supplemented with 0.1 μm 2-(3-(6-methylpyridin-2-yl)-1H-pyrazol-4-yl)-1,5-naphthyridine ("ALK5 inhibitor II", "ALK5i") (Axxora™, San Diego, Calif.; Cat. No. ALK-70-445), 100 ng/mL Noggin, 500 nM (2S,5S)-(E,E)-8-(5-(4-(trifluoromethyl)

phenyl)-2,4-pentadienoylamino)benzolactam ("TPB") (Shanghai ChemPartner Co., LTD™, China) and 1% B27. For the last day of culture, cells were treated with 5 mg/mL Dispase™ for 5 min at 37° C., followed by gentle pipetting to break the cells into cell clusters (<100 m). The cell clusters were transferred into a polystyrene 125-500 ml Spinner Flask (Corning™), and spun at 80-100 rpm overnight in suspension with DMEM-HG supplemented with 0.2 M ALK5i, 100 nM (6-(4-(2-(piperidin-1-yl)ethoxy)phenyl)-3-(pyridin-4-yl)pyrazolo[1,5-a]pyrimidine, hydrochloride)) ("LDN") a BMP receptor inhibitor (Stemgent™, San Diego, Calif.; Cat. No. 04-0074) and 1% B27.

As shown in (FIG. S2), the resulting pancreatic endocrine precursor cells were assessed by fluorescence-activated flow cytometry ("FACS") and immuno-fluorescent staining (micrographs not shown). FACS staining was conducted as described in Diabetes, 61, 2016, 2012 and using the antibodies listed in TABLE 5. In brief, cells were incubated in TrypLE™ Express (Life Technologies™, Catalog No. 12604) for 3-5 minutes at 37° C. and released into single cell suspensions after which they were washed twice with a staining buffer of PBS containing 0.2% BSA (BD Sciences™, Cat. No. 554657). Cells ($1 \times 10^5$ to $1 \times 10^6$) were re-suspended in 100 µl blocking buffer of 0.5% human gamma globulin diluted 1:4 in staining buffer for surface marking. Added to the cells at a final dilution of 1:20 were directly conjugated primary antibodies followed by incubation at 4° C. for 30 minutes. The stained cells were twice washed in the staining buffer, followed by re-suspension in 200 µl staining buffer and then incubated in 15 µl of 7-AAD for live/dead discrimination before FACS analysis on the BD Canto II. Intracellular antibody staining was accomplished by first incubating with Green Fluorescent LIVE/DEAD cell dye (Life Technologies™, Cat. No. L23101) at 4° C. for 20 minutes followed by a single wash in cold PBS. Fixing of cells was in 250 µl of Cytofix/Cytoperm™ buffer (BD Sciences™, Cat. No. 554723) followed by re-suspension of the cells in 100 µl of Perm™ wash buffer staining/blocking solution with 2% normal goat serum. Cells were incubated at 4° C. for 30 minutes with primary antibodies at empirically pre-determined dilutions followed by two washes in Perm/Wash buffer. Cells were then incubated with the appropriate antibodies at 4° C. for 30 minutes and then washed twice prior to analysis on the BD FACS Canto II™. The concentrations of antibodies used are shown on TABLE 5. The antibodies for pancreas markers were tested for specificity using human islets or undifferentiated H1 cells as a positive control. For secondary antibodies, the following were added and incubated at 4° C. for 30 minutes: anti-mouse Alexa Fluor™ 647 at 1:500 (Life Technologies™), goat anti-rabbit PE at 1:200 (v) or donkey anti-goat Alexa 647™ at 1:800 (Life Technologies™) followed by a final wash in perm Wash buffer and analysis on BD FACS Canto II using BD FACS Diva Software™ with at least 30,000 events being acquired.

Figure 8A:
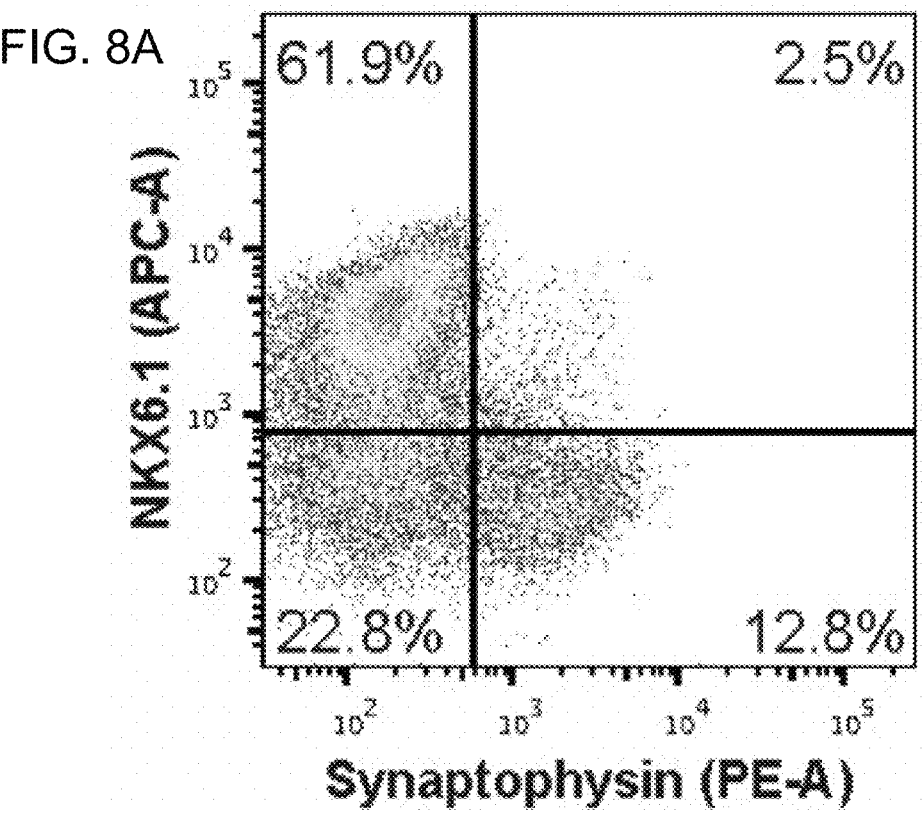
FIGS. 8A-8D show graphs of flow cytometry results of key markers of the Stage 4, day 4 cells of Example 2 showing co-expression of synaptophysin and NKX6.1, chromogranin and NKX2.2, PDX1 and Ki67, and PAX4 and OCT 3/4.
Figure 8B:
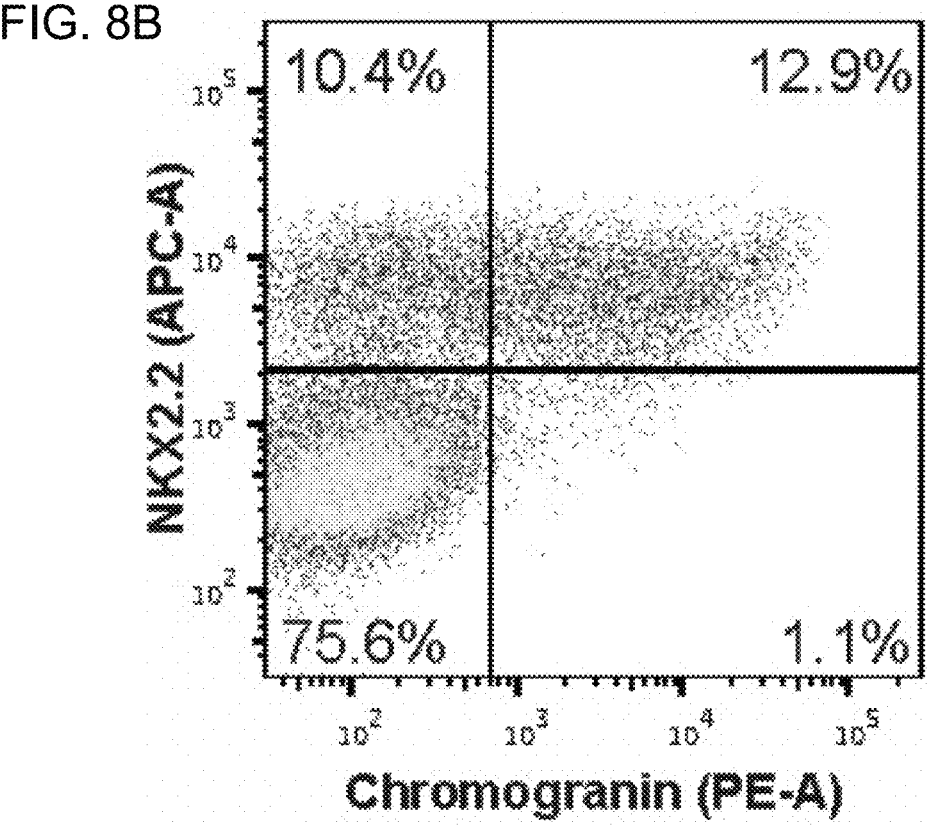
Figure 8C:
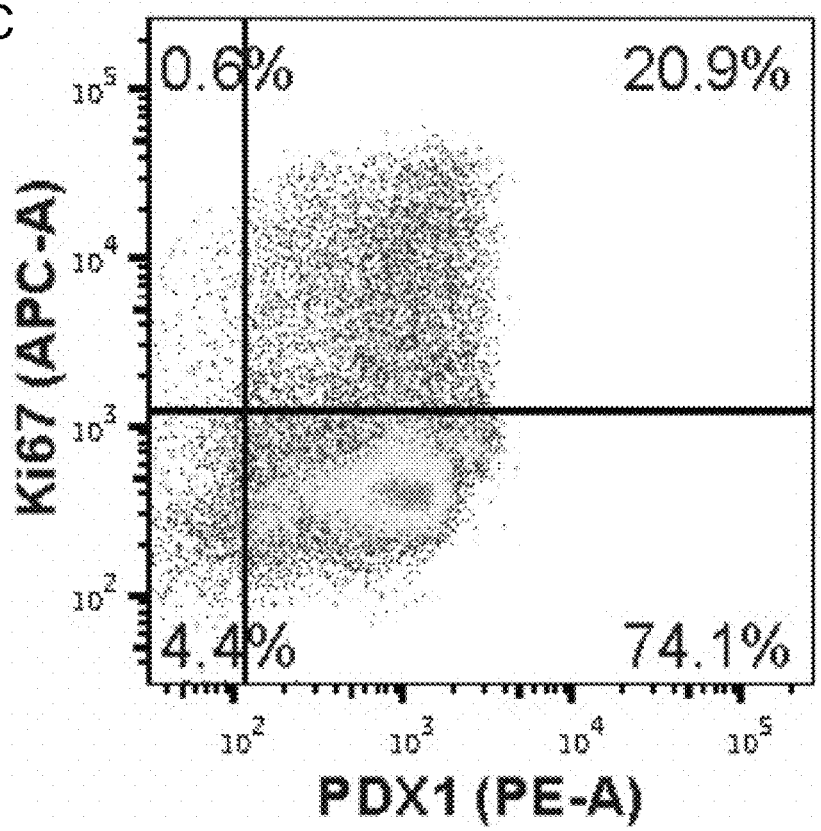
Figure 8D:
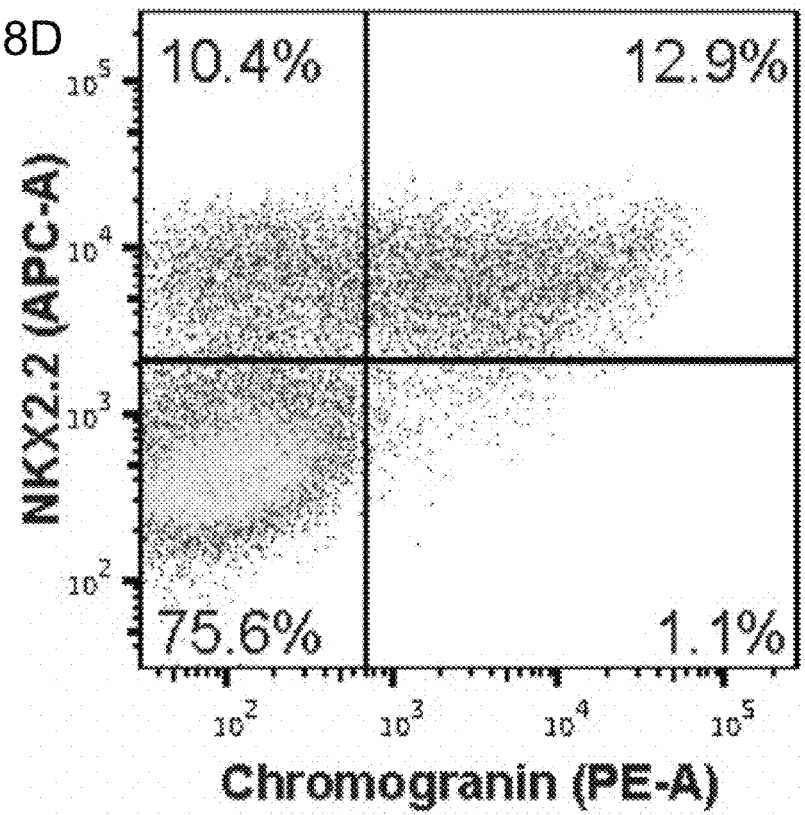

Following in vitro differentiation, 98.8% of cells expressed PDX1 and 71.7% expressed NKX6.1 (FIGS. 8A, 8C, 8D and 8G), two key markers of pancreatic endoderm. Approximately 20% of PDX1-positive cells were in the cell cycle, as indicated by Ki67 or PCNA expression (FIGS. 8A and 8D), and the pluripotency marker OCT 3/4 was not detected (FIG. 8A). Although ~16% of progenitor cells expressed endocrine markers (FIGS. 8A and 8B), only 2.8% of synaptophysin-positive cells co-expressed NKX6.1 (FIG. 8A) and most were polyhormonal (FIG. 8F), indicative of an immature endocrine population. Insulin/C-peptide-positive cells only rarely co-expressed PAX6 (FIG. 8E) or NKX6.1 (FIG. 8C) at this stage of differentiation.

TABLE 5

List of Antibodies used for FACS analysis

| Antigen | Species | Source/Catalogue Number | Dilution |
| --- | --- | --- | --- |
| Glucagon | Mouse | Sigma-Aldrich ™/G2654 | 1:250 |
| Insulin | Rabbit | Cell Signaling Technology Inc. ™, Danvers. MA/3014B | 1:10 |
| NKX6.1 | Mouse | Developmental Studies Hybridoma Bank ™ Iowa City, Iowa/F55A12 | 1:50 |
| NKX2.2 | Mouse | Developmental Studies Hybridoma Bank/74.5A5 | 1:100 |
| PDX1 | Mouse | BD BioSciences ™, San Jose, CA/562161 | 1:50 |
| Ki67 | Mouse | BD Biosciences ™, 558595 | 1:20 |
| Pax6 | Mouse | BD Biosciences ™, 561552 | 1:20 |
| Chromogranin A | Rabbit | Dako, Carpinteria ™, CA/A0430 | 1:40 |
| ISL-1 | Mouse | BD Biosciences ™, 562547 | 1:20 |
| NeuroD | Mouse | BD Bioscience ™, 563001 | 1:40 |
| FOXA2 | Mouse | BD Bioscience ™, 561589 | 1:80 |
| OCT3/4 | Mouse | BD Biosciences ™, 560329 | 1:20 |

Example 3: Exposure to HFDs Did not Affect the Function of hESC-Derived Endocrine Cells In Vivo The pancreatic endocrine precursor cells of Example 2 were encapsulated within a 20 l Theracyte™ macro-encapsulation device (TheraCyte Inc.™, Laguna Hills, Calif.) as follows. Approximately $5 \times 10^6$ endocrine precursor cells (in cluster form) were placed into a positive displacement pipette. Using slight pressure, the tip of the capillary/piston tip containing cells was placed snug in the hub of the 24 gauge catheter and the cells dispensed from the positive displacement pipette through the catheter into the device. The device was sealed using a titanium barb. The encapsulated pancreatic endocrine precursor cells were then transplanted subcutaneously into seven SCID-beige mice from each of the four diet regimens. All mice were anaesthetized with inhalable isoflurane and transplant recipients received approximately $5 \times 10^6$ pancreatic endocrine precursor cells subcutaneously on the right flank. Four sham mice received the same surgical procedure, but no macro-encapsulation device was implanted.

Figure 2A:
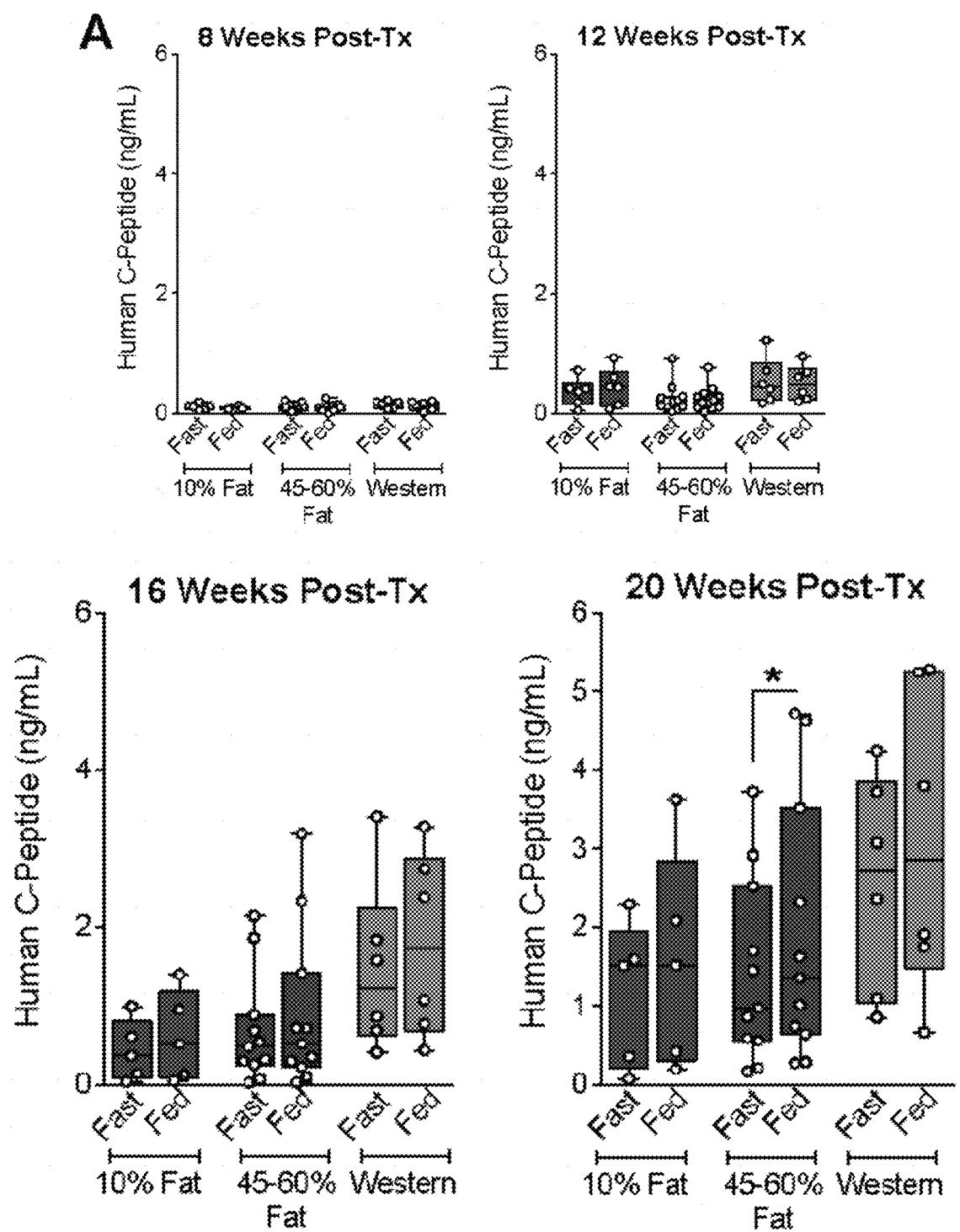
FIG. 2A shows a graph of human C-peptide levels measured after an overnight fast and 40 minutes after an oral mixed-meal challenge at 8, 12, 16, and 20 weeks after transplant in the mice of Example 2.
Figure 2D:
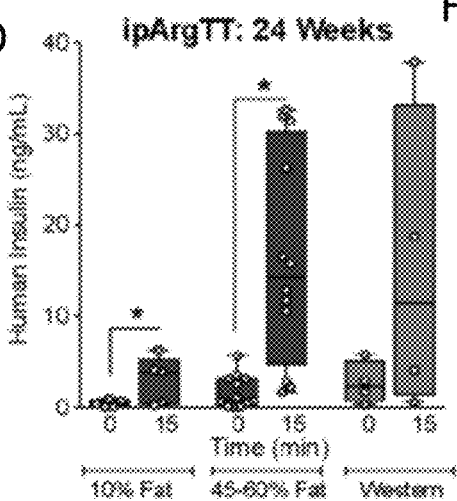
FIGS. 2D-2F show the results of human insulin and glucagon at 24 weeks post-transplant following an arginine tolerance test in the mice of Example 3, wherein (E) shows glucagon levels at 0 and 15 minutes in transplant recipients, and (F) shows glucagon levels in sham-treated mice (Sham, striped bars) and transplant recipients (Tx, solid bars) at 15 minutes only.
Figure 2E:
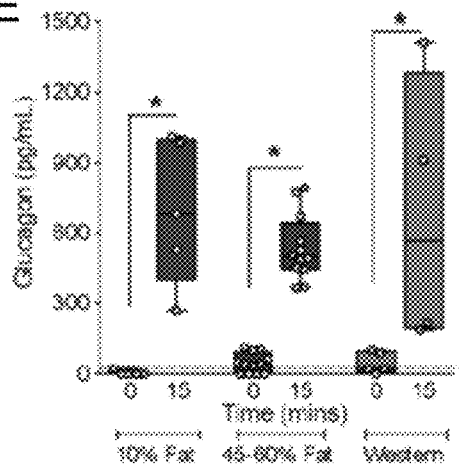
Figure 2F:
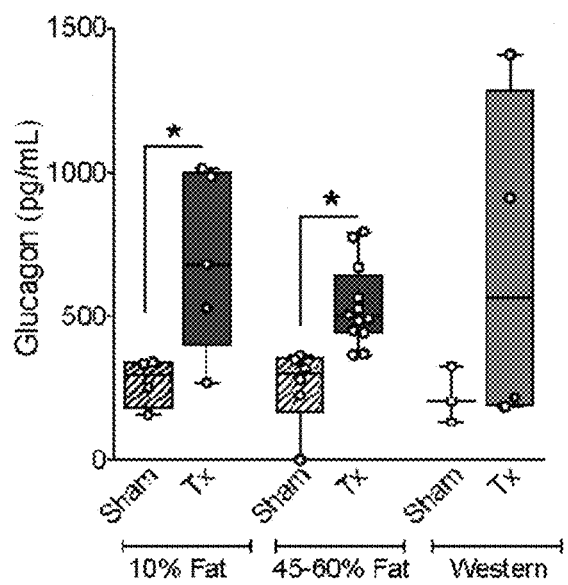

Following transplantation, the pancreatic endocrine precursor cells further differentiated in vivo and the resulting cells, from all diet groups, secreted similar levels of human C-peptide under basal and fed conditions between 8 and 20 weeks (FIG. 2A) and produced robust glucose-stimulated human C-peptide secretion at 18 weeks (FIGS. 2B,C). Similarly, human insulin secretion was induced by an arginine challenge in all diet groups at 24 weeks (FIG. 2D). A trend towards increased basal glucagon secretion in the HFD groups was observed, but because four out of five mice in the LFD group had undetectable fasting glucagon levels, it was not possible to do a statistical analysis (FIG. 2E). Arginine-stimulated glucagon levels were similar between diet groups (FIGS. 2E,F) and it was estimated that approximately half of the circulating glucagon may have originated from the hESC-derived cells, as indicated by the difference between transplanted and sham glucagon levels (FIG. 2F).

The Theracyte™ devices were cut in half at the time of tissue harvest and stored in RNAlater Stabilization Solution™ (Qiagen, Inc.™, Valencia, Calif.; Cat. No. 76106) at −80° C. until use. Excess mouse tissue was first removed from the outside of the device before placing the device in 2 mL PBS. The edge of the device was cut off, the outer membranes peeled back, and the device isolated and placed into 400 µl Qiagen™ Buffer RLT Plus (Qiagen Inc.™, Cat. No. 79216) containing 0.1% (v/v) beta-mercaptoethanol. The PBS was collected and centrifuged at 2000×g for 4 min to collect any cells that spilled out of the device. The cell pellet was re-suspended in the same RLT Plus buffer used for lysing the corresponding device. RNA was isolated using Qiagen RNeasy Plus Mini™ kit (Qiagen Inc.™; Cat. No 74316) and eluted in 16 µl nuclease-free water. RNA concentration was measured using the NanoDrop8000™ (Thermo Scientific™).

Human islets were obtained from four organ donors (23-48 years of age; two males and two females) as a positive control for quantitative polymerase chain reaction ("qPCR") analysis (Prodo Labs; Irvine, Calif.). Islet purity ranged from 85-95% and viability from 90-95%. All human islet preparations showed a 2 to 4-fold increase in human insulin secretion after incubation with high glucose concentration (data not shown) using a static glucose-stimulated insulin secretion assay. In brief, human islet cells (approximately 20 to 50 islet cells) were rinsed twice with Krebs buffer (129 mM NaCl, 4.8 mM KCL, 2.5 mM CaCl 2, 1.2 mM $MgSO_4$. 1 mM $Na_2HPO_4$, 1.2 mM $KH_2PO_4$, 5 mM $NaHCO_3$, 10 mM HEPES, and 0.1% BSA in deionized water and then sterile filtered) and then pre-incubated in Krebs buffer for 40 mins. Cells were then incubated in Krebs buffer spiked with 3.3 mM glucose for 60 mins. The cells were then transferred to another plate containing Krebs buffer spiked with 16.7 mM glucose and incubated for an additional 60 mins. Supernatant samples were collected after each incubation period and frozen at −70° C. for human C-peptide ELISA (Mercodia™, Winston-Salem, N.C.; Cat. No. 10-1141-01) measurement.

Due to a low amount of human cells/tissue in the device, and the high probability that some of the RNA would be from the surrounding mouse tissue, the amount of human RNA was measured using a standard curve. First, all RNA was converted into cDNA using the High Capacity cDNA Reverse Transcription Kit™ (Thermo Fisher Scientific™/ Life Technologies™) with the following program: 25° C. for 10 minutes, 37° C. for 2 hours, 4° C. hold. Pre-amplification was performed using a primer pool specific for the genes run (TABLE 3) and TaqMan PreAmp 2× Master Mix™ (Thermo Fisher Scientific™/Life Technologies™) with the following cycling conditions: 95° C. 10 min, 8 cycles of 95° C. 15 s and 60° C. 4 min, 99° C. 10 min, and 4° C. hold.

To determine the amount of human cDNA, real-time PCR was performed on the Pre-amplified cDNA using primers specific to human GAPDH and mouse Gapdh and run against a standard curve made from known amounts of cDNA from a human cell line. Sixteen ng of calculated human cDNA was run on a custom TaqMan Low Density Array™ (Thermo Fisher Scientific™/Life Technologies™; TABLE 3) using the Quant Studio 12K Flex Real Time PCR™ instrument (Thermo Fisher Scientific/Life Technologies). Data were analyzed using Expression Suite™ software (v1.0.3, Thermo Fisher Scientific™/Life Technologies™) and normalized to undifferentiated H1 cells using the delta delta Ct method.

Prior to transplant, a portion of the pancreatic endocrine precursor cells were fixed overnight in 4% paraformaldehyde ("PFA") and then embedded in 1% agarose prior to paraffin-embedding. Theractye™ devices, as well as a variety of tissues (listed in TABLE 3 above), were harvested at 29 weeks post-transplant, fixed in 4% PFA and stored in 70% ethyl alcohol prior to paraffin-embedding. All paraffin sections (5 m thickness) were prepared by Wax-it Histology Services™ (Vancouver, BC). Primary antibodies are provided in TABLE 4, above. Hemotoxyline and eosin ("H&E") staining was performed using standard procedures and tissue analysis was performed in a blinded fashion by an independent pathologist (Nova Pathology PC™, Bellingham, Wash., USA).

At 29 weeks post-transplant, the encapsulated hESC-derived grafts had similar or significantly higher levels of islet-related genes compared to human islets and there were no significant differences among different LFD or HFD groups (data not shown—CHGB; INS; CGC; SST; NKX6.1; PAX6; ISL1; MAFA; ABCC8; IAPP; PCSK1; PCSK2; GCGR; G6PC2; SLC30A8; and UCN3). In particular, genes CHGB, INS, CGC, SST, MAFA and PCSK1, had similar gene expression in encapsulated hESC-derived grafts (i.e. for 10% fat; 45% fat; 60% fat and Western diets) when compared to human islets. However, when NKX6.1, PAX6, ABCC8, IAPP, PCSK2, GCGR, G6PC2, SLC30A8 and UCN3 gene expression in encapsulated hESC-derived grafts (i.e. for 10% fat; 45% fat; 60% fat and Western diets) was compared to human islets, the hESC-derived graft cells generally had significantly higher levels of gene expression than the human islets.

The majority of cells within the harvested devices were immuno-reactive for the endocrine marker synaptophysin, and a small proportion expressed the ductal marker CK19; trypsin-positive exocrine cells were rarely observed (micrographs not shown). The grafts were largely composed of cells expressing either insulin, glucagon or somatostatin, and the percentage of mono-hormonal insulin-positive and glucagon-positive cells was similar between diet groups (FIG. 3). A minor, but significantly higher percentage of cells that were immuno-reactive for both insulin and glucagon in the HFD grafts compared to LFD grafts (FIG. 3) were noted. Aside from these rare polyhormonal cells, exposure to HFDs did not appear to generally influence the maturation state of hESC-derived insulin-secreting cells; the majority of insulin-positive cells in all transplant recipients co-expressed PDX1, NKX2.2, NKX6.1, and MAFA at 29 weeks post-transplant (micrographs not shown).

Example 4: hESC-Derived Insulin Secreting Cells Improved Diet-Induced Dysglycemia and Insulin Resistance Glucose tolerance tests ("GTTs") were performed at 18 and 24 weeks post-transplant following a 6-hour morning fast and administration of glucose by oral gavage or intraperitoneal ("i.p.") injection (2 g glucose/kg BW, 30% solution; Vétoquinol™, Lavaltrie, QC). Glucose-stimulated human C-peptide secretion from engrafted cells was assessed following an overnight fast and an i.p. injection of glucose (2 g/kg). Insulin tolerance tests ("ITTs") were performed 22 weeks-post-transplant following a 4-hour morning fast and administration of human synthetic insulin (0.7 IU/kg body weight; Novolin Ge™ Toronto, Novo Nordisk™, Mississauga, Canada). For monthly mixed-meal challenges, mice received an oral gavage of Ensure™ (8 uL/g body weight; Abbott Laboratories™, Abbott Park, Ill., USA) following an overnight fast (~16 hours). For arginine tolerance tests ("ArgTT"), mice received an i.p. injection of arginine (2 g/kg, 40% solution; Sigma-Aldrich™) following a 4-hour morning fast.

Figure 9C:
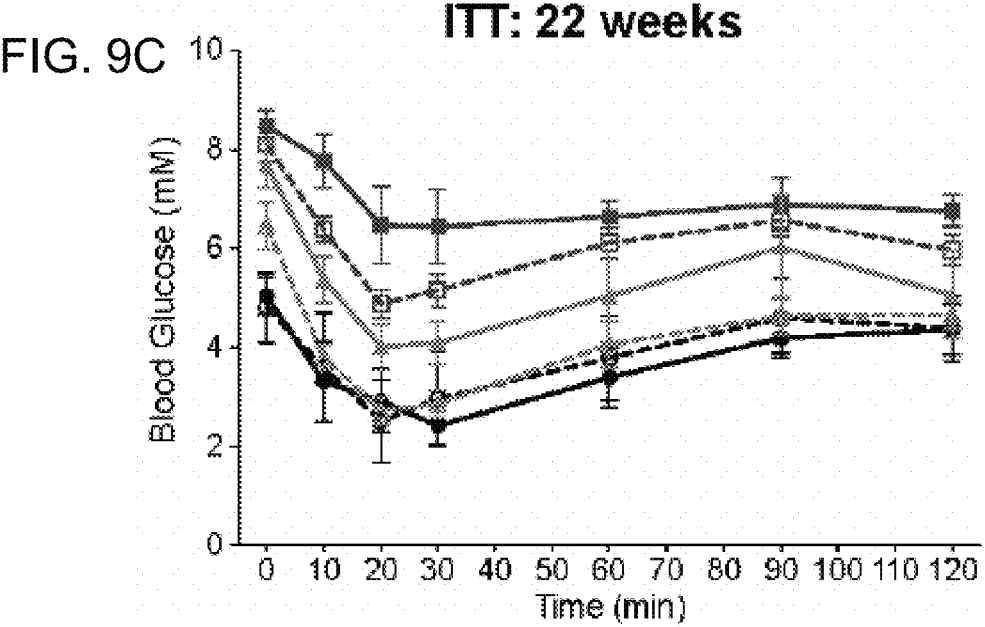
FIGS. 9C and 9D show graphs of the results of insulin tolerance tests performed on the mice of Example 4 at 22 weeks post-transplant.
Figure 9D:
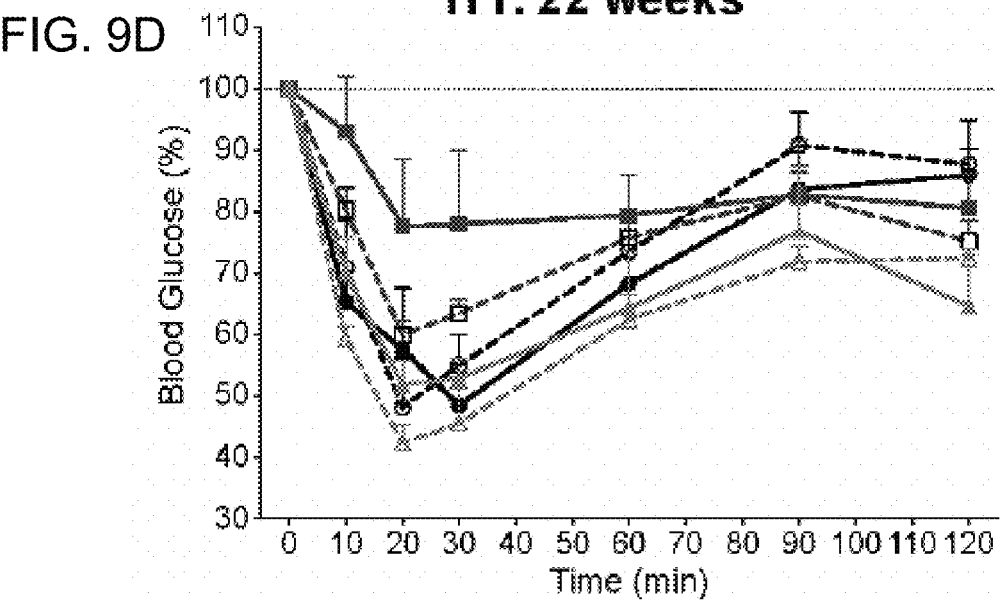

All HFD groups continued to be overweight and hyperglycemic under fasting conditions compared to LFD controls throughout the duration of the study. Transplantation of the encapsulated cells did not affect either body weight or fasting blood glucose levels compared to sham surgery (data not shown). However, significant improvements in long-term glycemic control, as measured by HbA1C, following transplantation alone (FIGS. 4A and B) was observed. HbA1C levels were elevated at 12 and 24 weeks in all HFD sham mice compared to LFD sham controls and significantly reduced by transplantation in the 45-60% fat group at both ages (FIGS. 4A and 4B). Transplant recipients on 45-60% fat diets also displayed a significantly lower glucose excursion following a mixed-meal stimulus compared to sham mice at 20 weeks (FIG. 4C) and all HFD transplant recipients had significantly improved glucose tolerance at 24 weeks post-transplant (FIG. 4E, FIG. 9B); these improvements were not yet evident at 18 weeks (FIG. 4D, FIG. 9A). Glucose tolerance in the 45-60% group was not completely ameliorated at 24 weeks, but transplant recipients in the western group had an area under the curve that was indistinguishable from controls (FIG. 4E; FIG. 9B). A significant improvement in insulin sensitivity at 22 weeks in transplanted HFD-fed mice compared to shams (FIG. 4F; FIGS. 9C and 9D) was also observed, which may have contributed to the improved glucose tolerance in HFD transplant recipients (FIG. 4E).

To measure endogenous pancreatic beta and alpha cell area three pancreas sections per animal, separated by at least 200 m, were immuno-stained for insulin and glucagon. Whole slide fluorescence scanning was performed using the ImageXpress Micro Imaging System™, and images were stitched together and analyzed using MetaXpress Software™ (Molecular Devices Corporation™, Sunnyvale, Calif.). The beta cell or alpha cell fraction was calculated as the insulin-positive or glucagon-positive area/total pancreas area and the average of three sections per animal was then multiplied by the pancreas weight. To quantify the endocrine composition within devices, the number of DAPI-positive nuclei were counted using the Multi Wavelength Cell Scoring™ module in MetaXpress™ and the number of cells that were immuno-reactive for insulin, glucagon or both hormones was counted manually by an investigator who was blinded to the treatment groups.

Figure 10A:
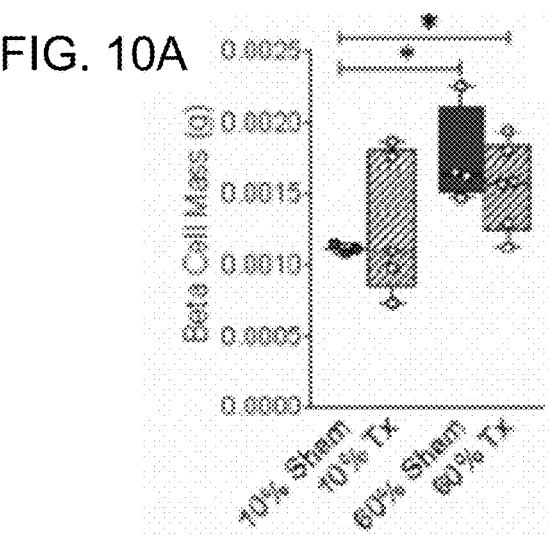
FIGS. 10A, 10B and 10C show graphs of the beta cell mass (10A), alpha cell mass (10B) and the ratio of insulin to glucagon (10C) immuno-staining in pancreas sections from mice of Example 4, 29 weeks post-transplantation or sham surgery and at 36 weeks after administration of the diets.
Figure 10B:
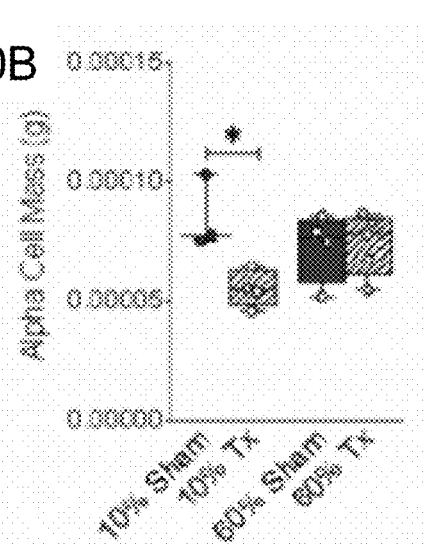
Figure 10C:
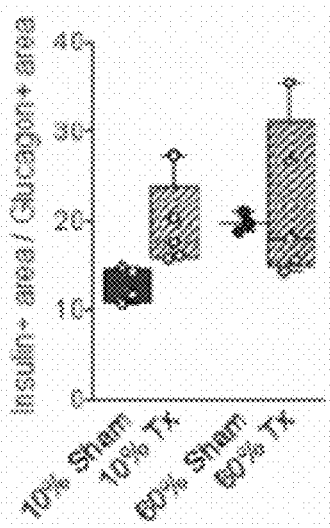

Beta cell mass was significantly higher in all mice on 60% fat diets compared to LFD sham controls, and there was no difference between sham and transplanted mice in either diet group (FIG. 10A). There was no effect of HFDs on alpha cell mass, but a significant reduction in alpha cell mass was observed in LFD transplant recipients compared to LFD shams (FIG. 10B). There were no significant differences in the ratio of insulin-positive to glucagon-positive area in the pancreas of mice on either diet (FIG. 10C).

Example 5: Cell Therapy Alone Had No Effect on the Obesity Phenotype

Figure 10D:
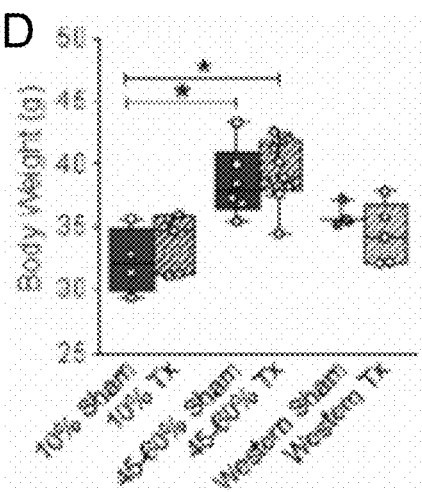
FIG. 10D-10G show graphs of the body weight (10D), epididymal fat weight (10E), plasma leptin levels (10F) and liver weight (10G) of the mice of Example 4.
Figure 10E:
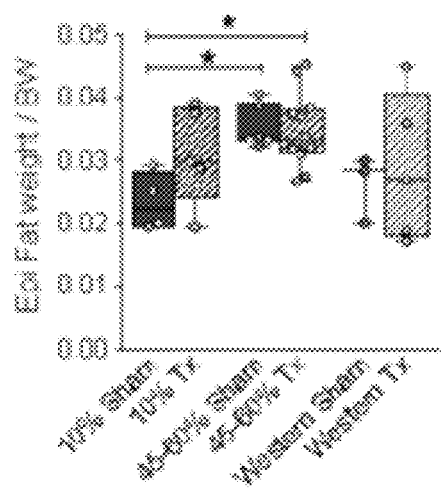
Figure 10F:
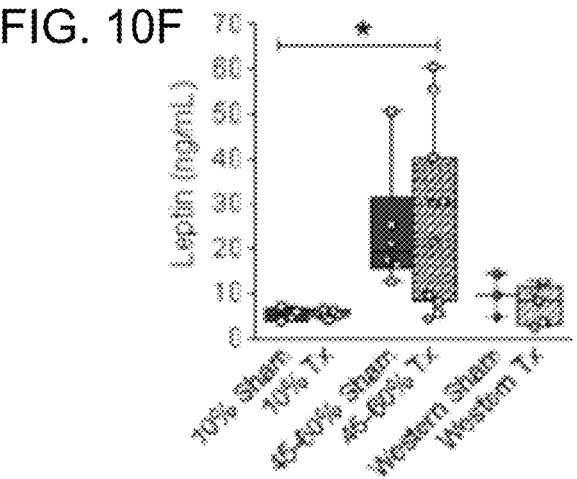
Figure 10G:
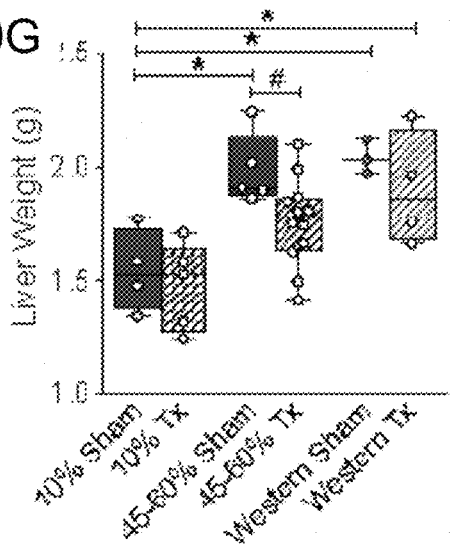

Although the encapsulated hESC-derived cells improved glucose homeostasis in HFD-fed mice, there was no apparent effect on the obesity phenotype. At the end of the study (29 weeks post-transplant and 36 weeks post-diet) mice on the 45-60% fat diets (sham and treated) had significantly higher body weight, adiposity (epididymal fat pad weight as a proportion of body weight) and circulating leptin levels than LFD shams (FIGS. 10D-10F). The obesity phenotype was more subtle in western diet mice during the first seven weeks (FIG. 1A) and by the end of the study there were no significant differences in body weight, adiposity or leptin levels between Western-fed mice (sham and tx) and LFD sham controls (FIGS. 10D-10F). All HFD groups had significantly higher liver weight (FIG. 10G) and evidence of cytoplasmic vacuolation, consistent with dietary lipidosis in the liver (not shown) compared to LFD controls. Transplant recipients fed 45-60% fat diets had significantly reduced liver weight relative to shams (not shown), although a pathology assessment did not reveal differences in cytoplasmic vacuolation in H&E-stained liver sections (not shown). Similarly, vacuolation of renal tubular epithelium was observed in kidney sections from all HFD groups (consistent with dietary lipidosis) and there was no effect of cell transplantation on this phenotype. Other tissue pathologies (Adipose Tissue, Perirenal; Ileum; Skeletal Muscle; Cecum; Jejunum; Spleen; Colon; Kidney; Stomach, Glandular; Duodenum; Liver; Stomach, Nonglandular; Heart; Lung; and Testis) were consistent with spontaneous age- and sex-related events and considered to be unrelated to exposure to diets or cell transplants.

Figure 11C:
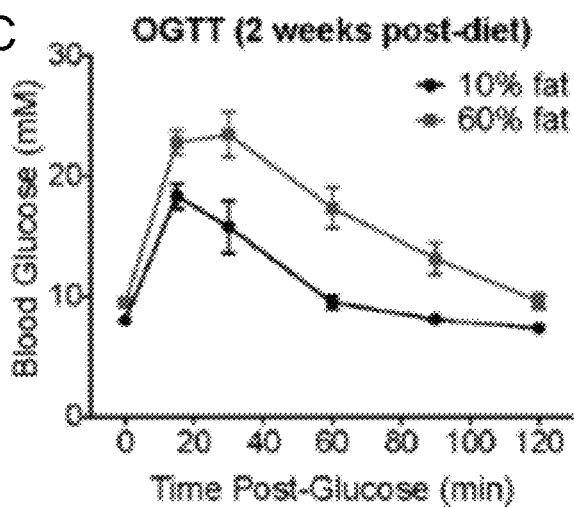
FIG. 11C shows a graph of the results of an oral glucose tolerance test 2 weeks after administration of either a low fat diet or a high fat diet to Example 6 mice.
Figure 11D:
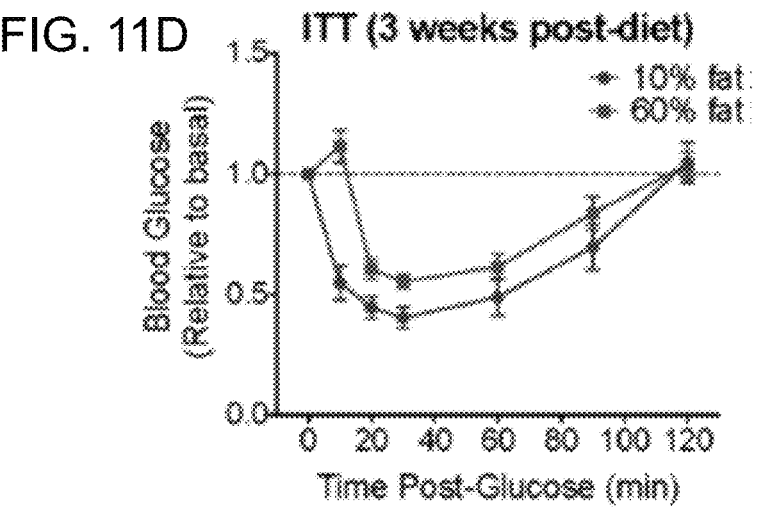
FIG. 11D shows a graph of the results of an insulin tolerance test 3 weeks after administration of either a low fat diet or a high fat diet to Example 6 mice.

Example 6: Combined Treatment with Pancreatic Endocrine Precursor Cell Transplants and an Antidiabetic Drug Improved Diet-Induced Obesity and Glucose Tolerance Mice were placed on either the 10% fat control diet (D12450K; n=8) for the duration of the study or 60% fat diet (D12492; n=64) for 6 weeks, followed by one of the following treatment regimens for the remainder of the study (n=16 per group): 1) 60% fat diet with no drug (D12492); 2) custom-made 60% fat diet containing rosiglitazone (18 mg/kg diet or ~3 mg/kg BW per day; Cayman Chemical™, Ann Arbor, Mich.; Research Diets™ custom diet formulation D08121002); 3) custom-made 60% fat diet containing sitagliptin (4 g/kg diet or ~750 mg/kg BW per day; sitagliptin phosphate monohydrate, BioVision Inc.™, Milpitas, Calif.; Research Diets™ custom diet formulation D08062502R); or 4) 60% fat diet (D12492) and metformin in drinking water (1.25 mg/mL or ~250 mg/kg BW per day; 1,1-Dimethylbiguanide hydrochloride, Sigma-Aldrich™). Treatment groups are summarized in TABLE 2, above. Mice rapidly developed attributes of T2D following HFD administration (FIG. 11).

Figure 5A:
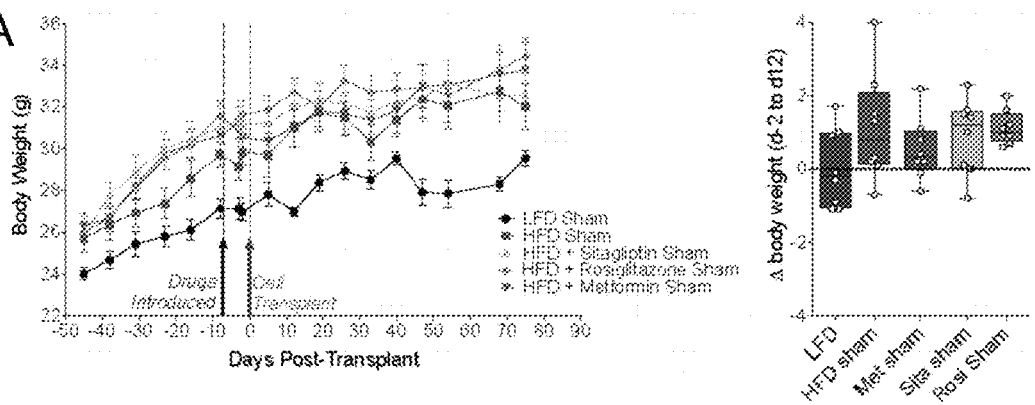
FIG. 5A-5F show diet-induced obesity was reversed following progenitor cell transplantation combined with an antidiabetic Drug, wherein fasting body weight was assessed in mice fed a 10% fat diet without drug (black/gray; all panels; n=8 mice), 60% fat diet without drug (A and B; n=7-8 mice per group), 60% fat diet plus metformin (A and C; n=7-8 mice per group), 60% fat diet plus sitagliptin (A and D; n=8 mice per group), or 60% fat diet plus rosiglitazone (A and E; n=8 mice per group). Body weight tracking for sham mice from all treatment groups is shown in (A). Sham mice (solid lines, closed symbols) and transplant recipients (Tx; dashed lines, open symbols) from each treatment group are shown together with the LFD control as a reference (B-E). The change in body weight from day 2 to day 12 is shown in box-and-whisker plots to the right of each line graph, with each data point representing an individual mouse. Data on line graphs are represented as mean±SEM. (F) Body weight pre-transplant (day 2) and post-transplantation (day 75).
Figure 5B:
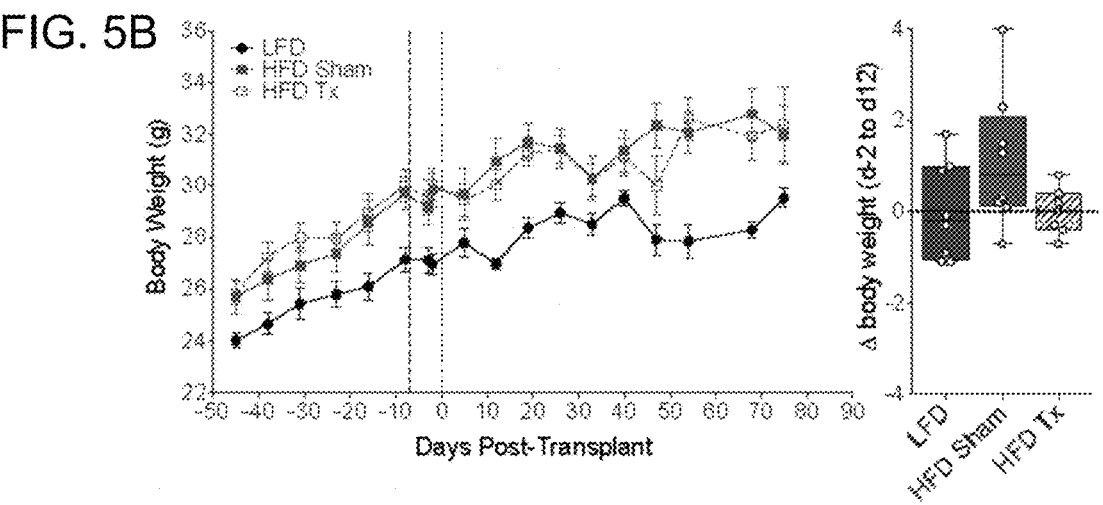
Figure 5C:
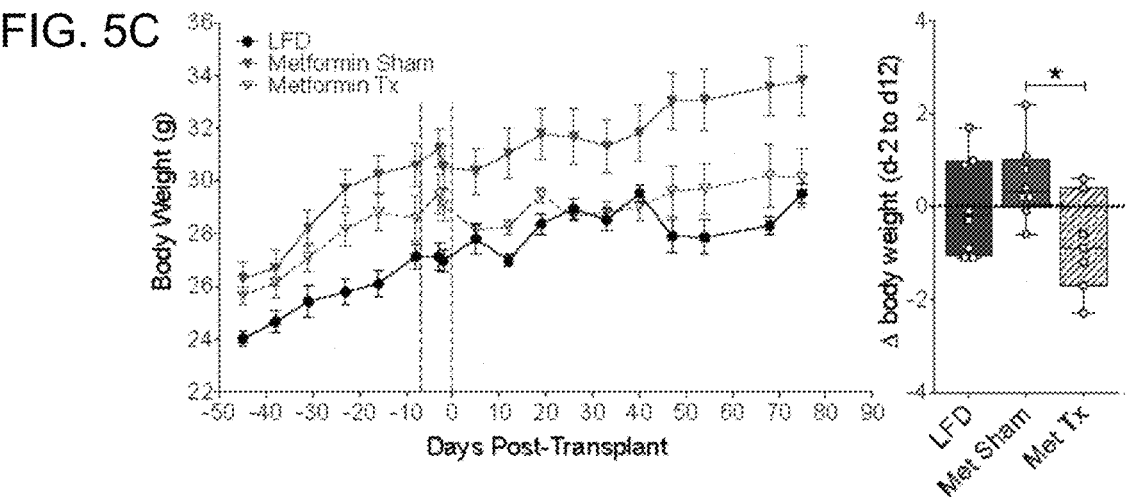
Figure 5D:
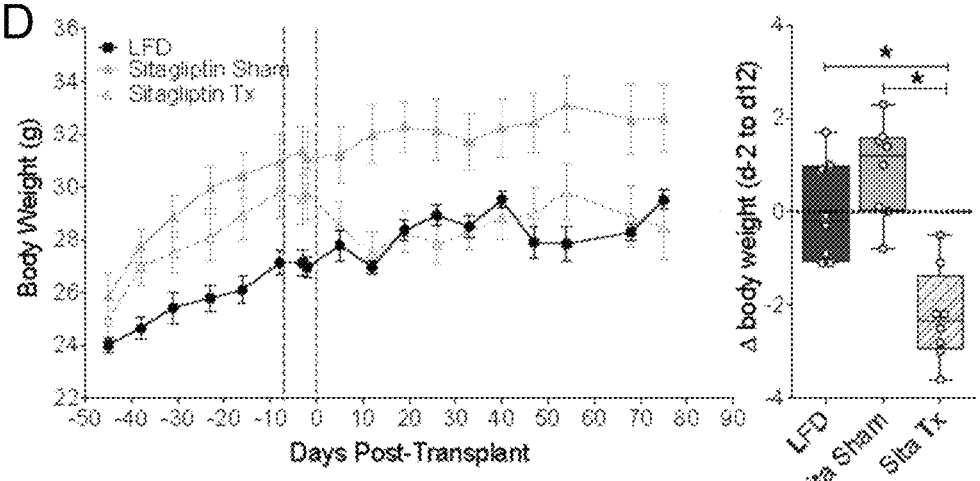
Figure 5E:
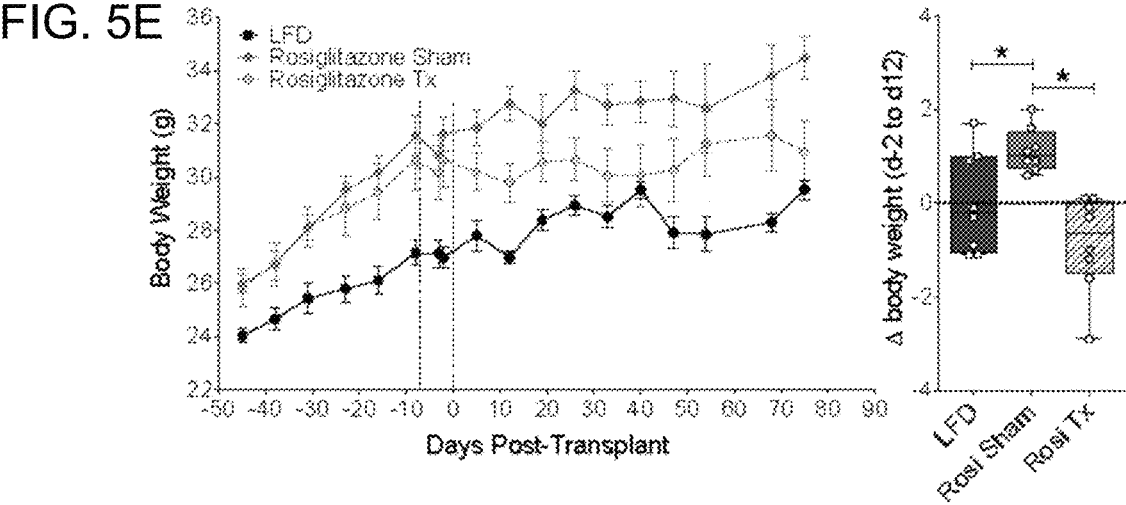
Figure 5F:
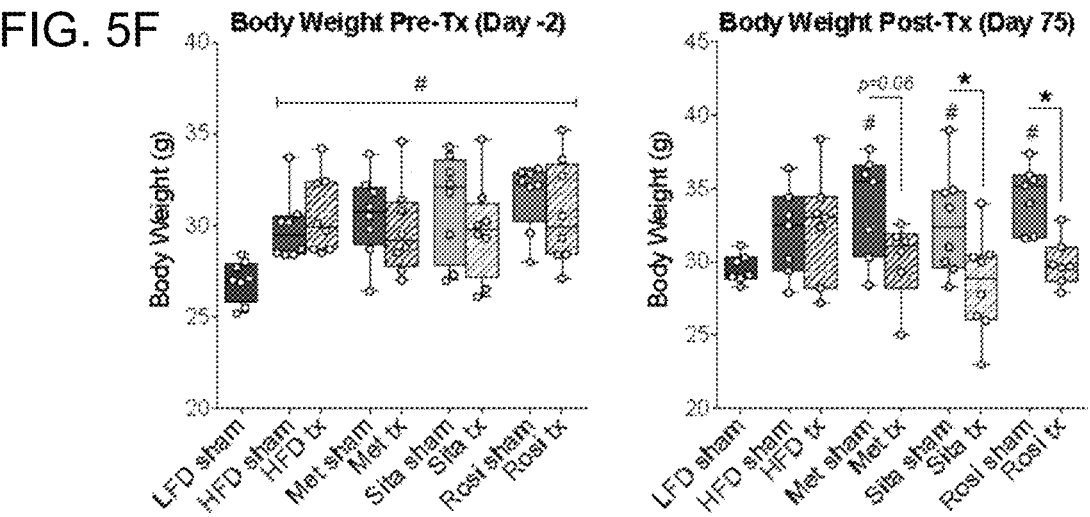
Figure 5G:
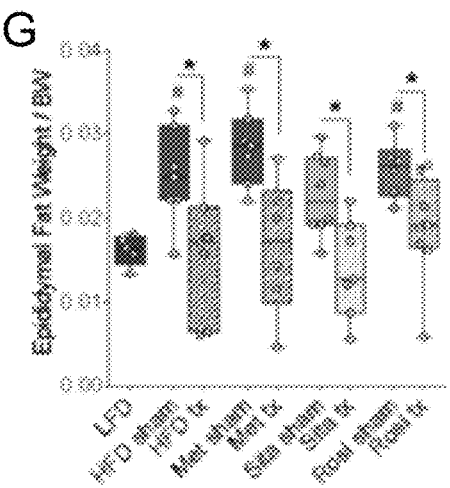
FIG. 5G shows a graph depicting the relative epididymal fat pad weight to body weight of Example 6 mice at 20 weeks post transplant.
Figure 5H:
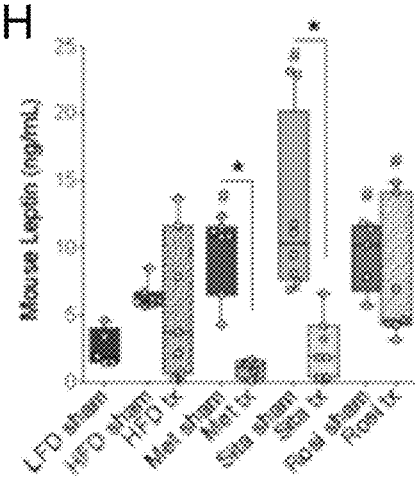
FIG. 5H shows a graph of plasma mouse leptin levels in Example 6 mice assessed 20 weeks post-transplant.

At the time of transplantation (one week after drug administration), all HFD-fed mice were significantly heavier than LFD controls (FIG. 5F). Weight loss was observed within the first two weeks following transplantation in HFD-fed mice on antidiabetic drugs (FIGS. 5C, 5D and 5E). In contrast, no change in body weight was observed during this time in either HFD transplant recipients without drug treatment (FIG. 5B), or sham mice on any drug (FIGS. 5A-E). All transplant recipients receiving antidiabetic drugs had significantly lower body weight on day 75 (FIG. 5F) and reduced epididymal fat pad weight (relative to body weight; FIG. 5G) compared to sham mice, such that neither parameter was different from LFD-fed sham controls. There was no effect of transplantation on body weight (FIG. 5B and F) or circulating leptin levels (FIG. 5H) in HFD-fed mice without drug treatment, although we did observe a reduction in relative epididymal fat pad weight in this cohort (FIG. 5G). The combination of a cell transplant with either metformin or sitagliptin resulted in significantly reduced circulating leptin levels compared to their respective sham controls (FIG. 5G). There was no effect of the cell therapy on restoring leptin levels in the rosiglitazone group (FIG. 5G).

It appears that there is some "synergy" with the combination therapy of pancreatic progenitor cell transplant and T2D small molecule treatment with regards to body weight since neither treatment alone had any effect on body weight (see FIGS. 5A and 5B). Similarly, at 12 weeks post-transplant, neither treatment alone had any effect on glucose tolerance (see FIGS. 6A and 6B), whereas the combinations tested caused significant improvements in blood glucose and body weight. Therefore, the effect of combination is greater than the sum of the treatments alone. The only exception to this might be Sitagliptin, which on its own showed a mild reduction in glucose tolerance.

Figure 6C:
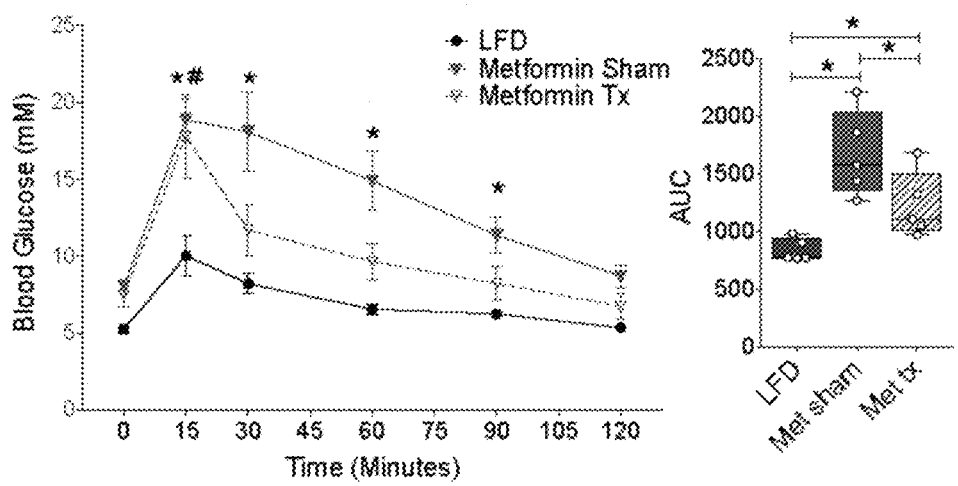
Figure 6D:
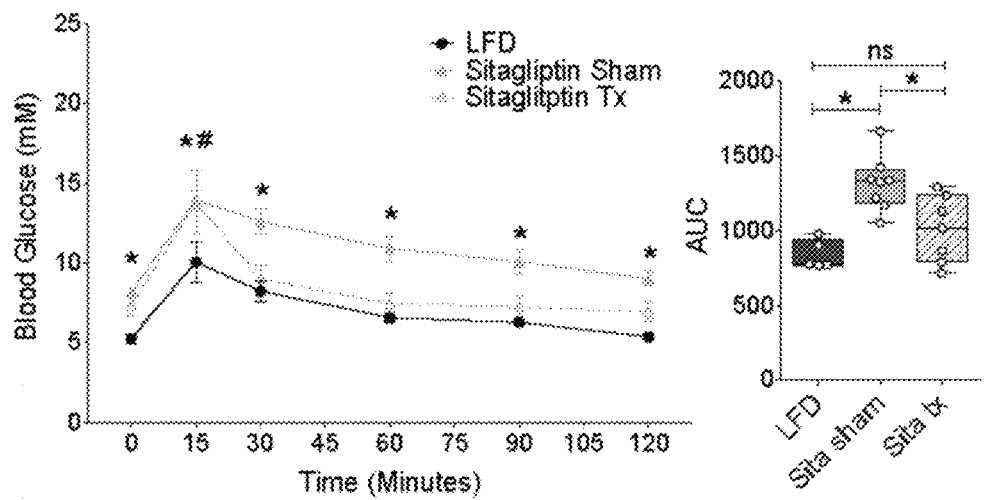
Figure 6E:
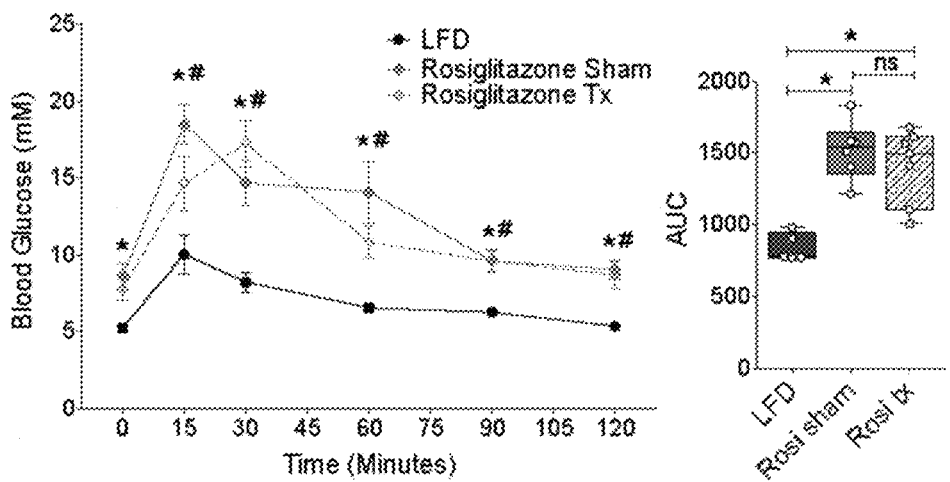
Figure 6F:
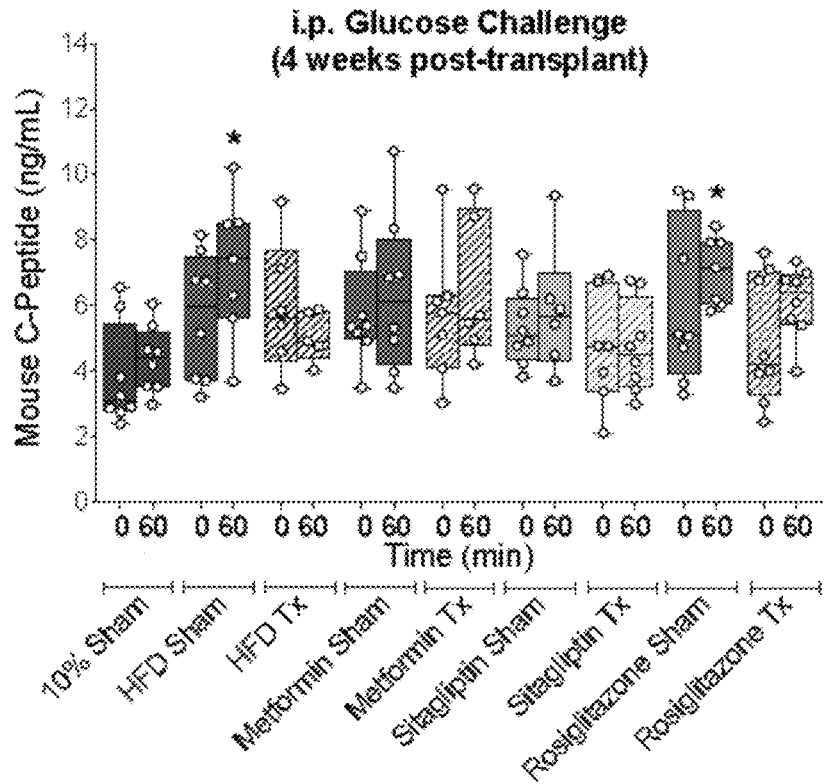
FIG. 6F shows a graph depicting mouse C-peptide levels for Example 6 mice 4 weeks (6F) post-transplant either before (0) or after 60 minutes after (60) a intraperitoneal injection of glucose.
Figure 6G:
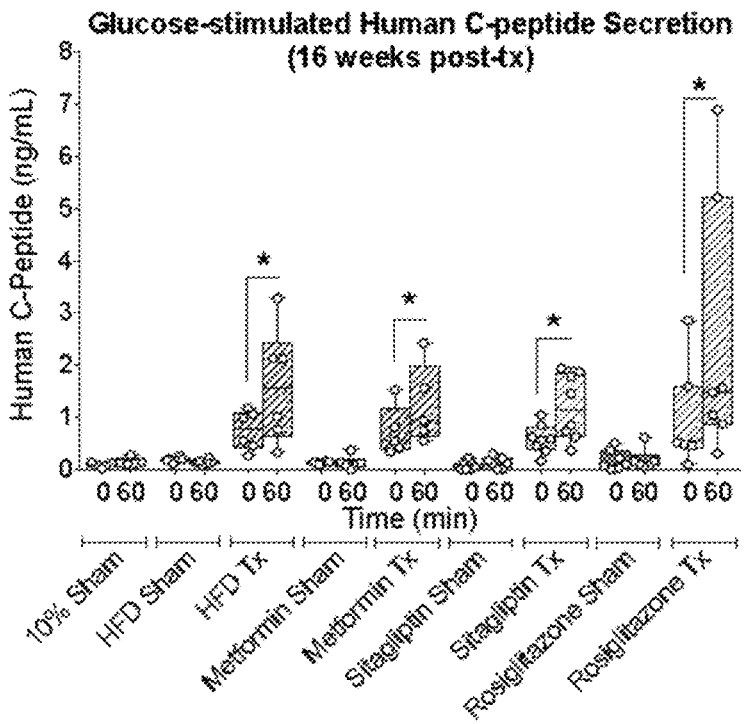
FIG. 6G shows the results of human C-peptide secretion in the Example 6 mice measured after an overnight fast and 60 minutes following an intraperitoneal glucose challenge.

Fasting blood glucose levels were not affected by any of the combination therapies throughout the study duration (data not shown). At 12 weeks post-transplant, mice in all HFD sham groups were glucose intolerant compared to LFD controls, regardless of drug treatment (FIG. 6A). There was no effect of the cell therapy on glucose tolerance at 12 weeks post-transplant in the HFD-fed mice without drug treatment (FIG. 6B) and likewise, the combination with rosiglitazone was also ineffective at this time (FIG. 6E). The cell therapy significantly improved glucose tolerance at 12 weeks post-transplant when combined with either metformin (FIG. 6C) or sitagliptin treatment (FIG. 6D). Glycemic control during an oral glucose challenge was indistinguishable between the LFD controls and HFD-fed mice receiving sitagliptin with the cell therapy, with the exception only of a marginally higher peak glucose level at 15 minutes post-gavage (FIG. 6D). The improved glucose tolerance in cell transplant recipients from the metformin- and sitagliptin-treated mice was associated with significantly reduced fasting mouse C-peptide levels compared to their respective sham controls at 16 weeks post-transplant (FIG. 6G), an effect that was not yet evident at 4 weeks (FIG. 6F). The improvements in glucose tolerance were not associated with differences in the function of hESC-derived grafts. All transplant recipients showed robust glucose-responsive human C-peptide secretion at 16 weeks and there were no differences in human C-peptide levels between HFD-fed mice treated with different antidiabetic drugs (FIG. 6G).

Example 7: Comparison of Stage 4 (S4) and Stage 7 (S7) Cell Transplants in Male and Female Mice Stage 4 cells pancreatic progenitors (similar to those in the above examples) were compared to Stage 7 cells, which are more differentiated pancreatic endocrine cells, were both transplanted into normal, health male or female mice, on a normal diet. Following transplantation the body weights of the mice were compared following a 4 hour fast (FIG. 12) and an overnight fast (FIG. 13). In these studies, mice receiving Stage 7 cells tended to weigh less than mice receiving Stage 4 cells, whether weighted after a 4 hr (FIG. 12) or overnight (FIG. 13) fast. Accordingly, some Stage 7 cells may be slightly preferable for reducing weight gain.

Example 8: Comparison of Stage 7 (S7) Cell Transplants with Human Islet Cell Transplants in Mice Stage 7 cells and human islet cells were compared in mice that were either diabetic (i.e. given STZ) or not (i.e. not given STZ) prior to transplantation, wherein body weight (FIG. 14A) and blood glucose (FIG. 14B) were compared post transplant. However, there was not a control that was given STZ, but not transplanted. Animals that received the cell transplants tended to gain less weight than control animals (FIG. 14A). As shown in FIG. 14 B, those animals that received transplants appeared more able to regulate blood glucose post transplant similar to control mice. However, the there was a greater time lag (i.e. ~120 days post Tx) for S7 Tx mice as compared to Human Islet TX mice (i.e. ~15 days post Tx), as would be expected. It is important to note that S7 recipients have normal glucose by ~100 days, and soon there after are actually lower than controls (hypoglycemic), similar to that of human islet recipients. The blood glucose level achieved is hypoglycemic for the mice, but since humans have naturally lower blood glucose levels and since the cells being transplanted are human cells, the blood glucose levels would not be considered hypoglycemic for humans. It is possible that the lower blood glucose reflects the fact that we are transplanting human cells, which have a lower set point for glucose levels than mice. Alternatively or in addition, it could also reflect the fact that an excess numbers of cells were transplanted.

Figure 15B:
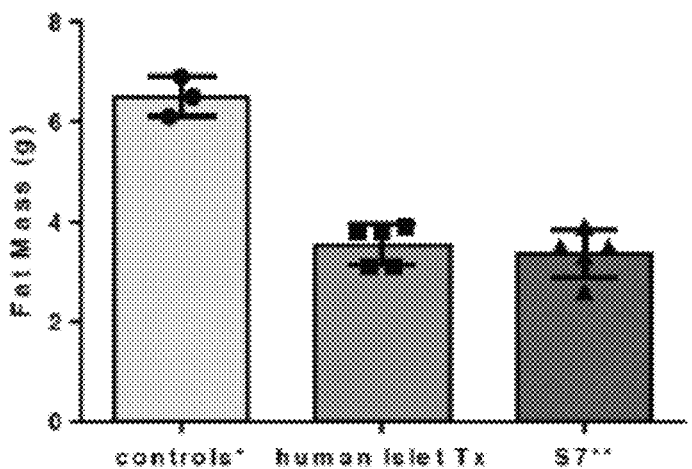
Figure 15C:
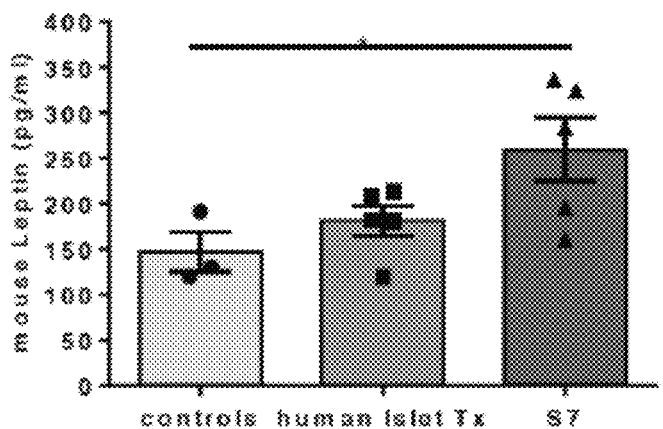
Figure 16A:
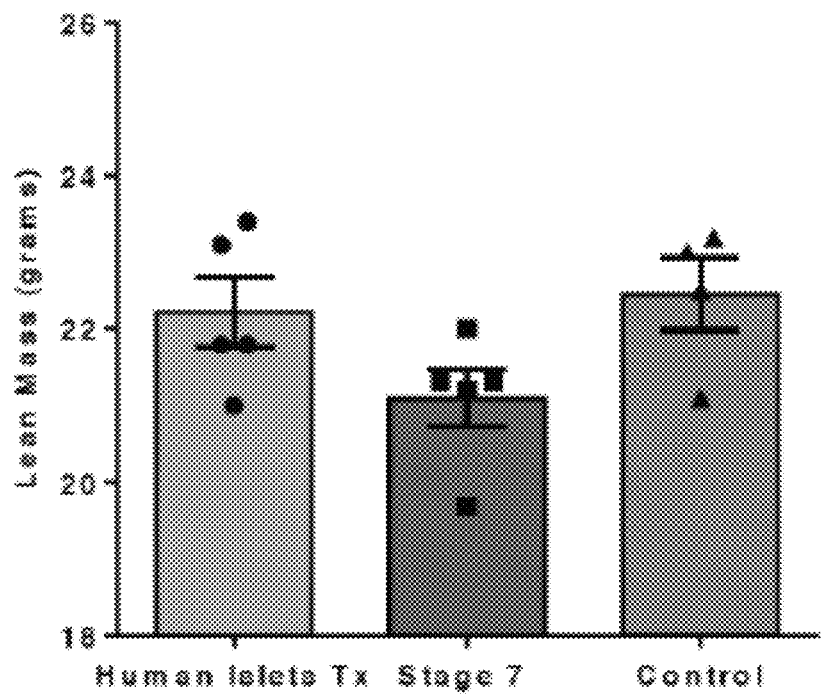
FIGS. 16A-16C show three graphs comparing control mice to mice transplanted with Stage 7 cells (S7) and mice transplanted with human islet cells (same mice from FIGS. 14 and 15), where (16A) lean body mass, (16B) fat mass and (16C) % body fat measured by dual-energy X-ray absorptiometry (DEXA).
Figure 16B:
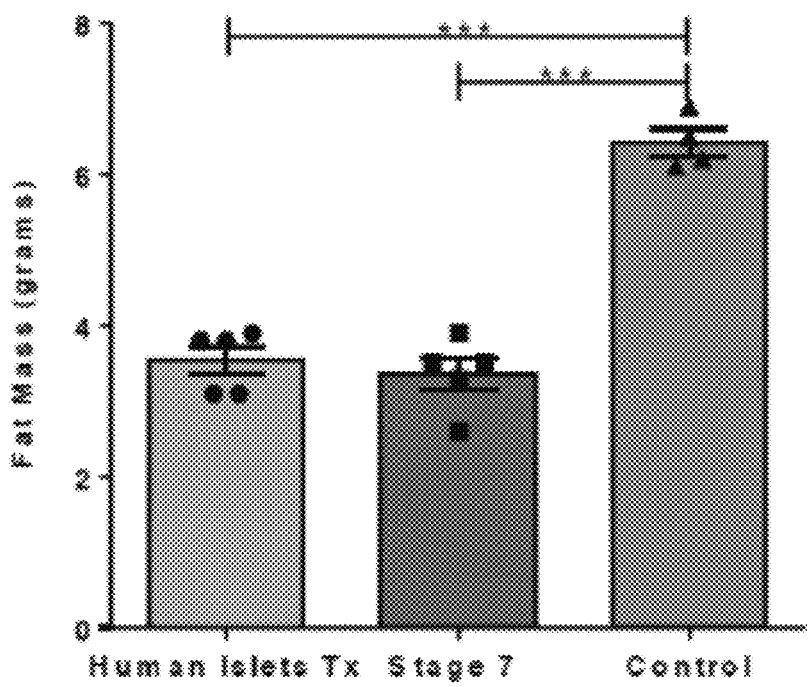
Figure 16C:
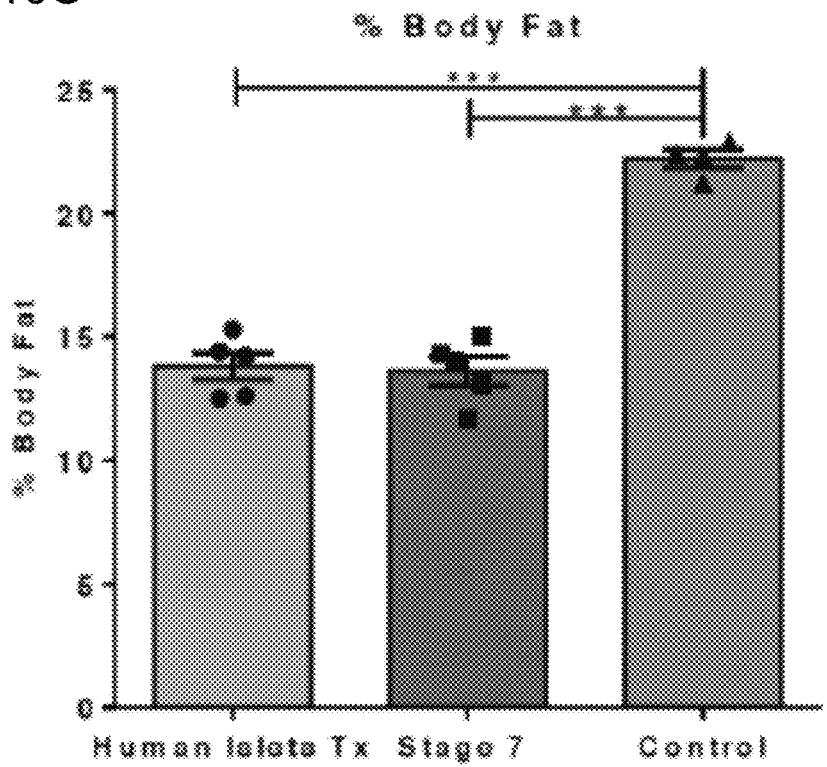

When the same animals studied in FIGS. 14A and 14B were compared for mouse leptin levels (FIG. 15A) leptin was consistently lower in the transplanted mice (either Stage 7 or human islet) than controls. Leptin is typically proportional to fat mass and when fat mass was measured by DEXA, both the human islet and Stage 7 cells had lower fat mass (FIG. 15B). Similarly, when body composition was compared between controls, human islet Tx mice and Stage 7 cell Tx mice the TX mice consistently had lower lean body mass (FIG. 16A), fat mass (FIG. 16B) and % body fat (FIG. 16C).

Figure 17A:
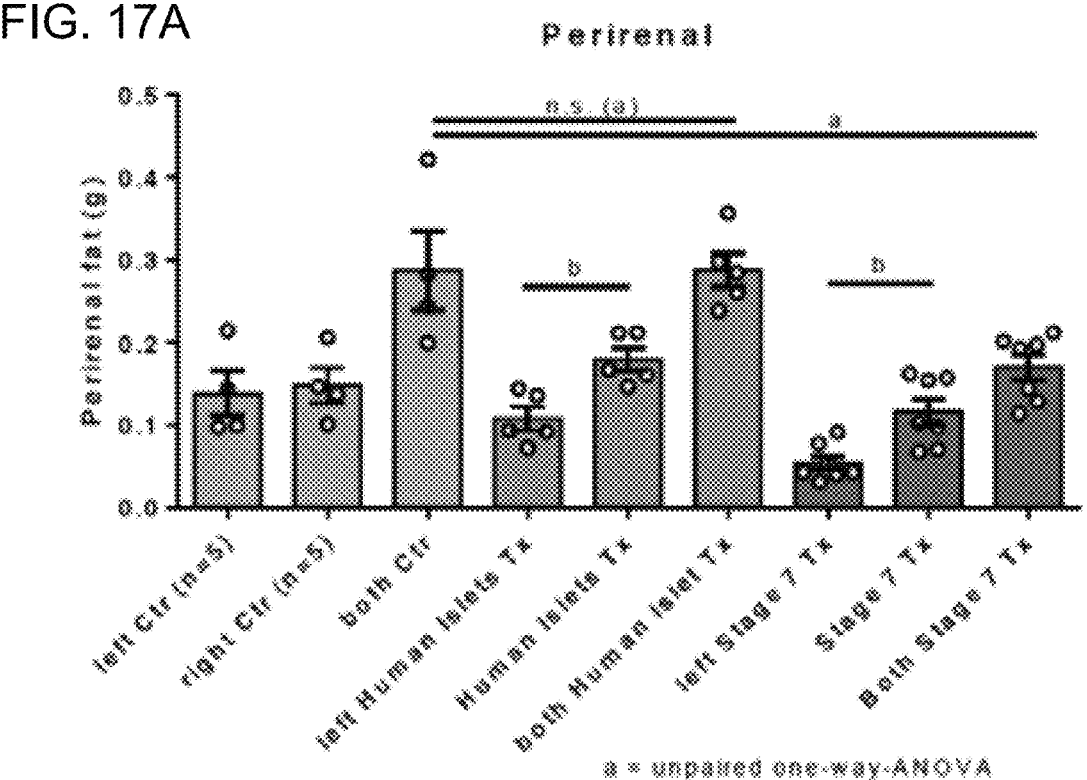
FIGS. 17A-17D show four graphs comparing control mice to mice transplanted with Stage 7 cells (S7) and mice transplanted with human islet cells (same mice from FIGS. 14 and 15) FIG. 17A) is the perirenal fat weight of either the left kidney or right kidney (graft bearing kidney) or both.
Figure 17B:
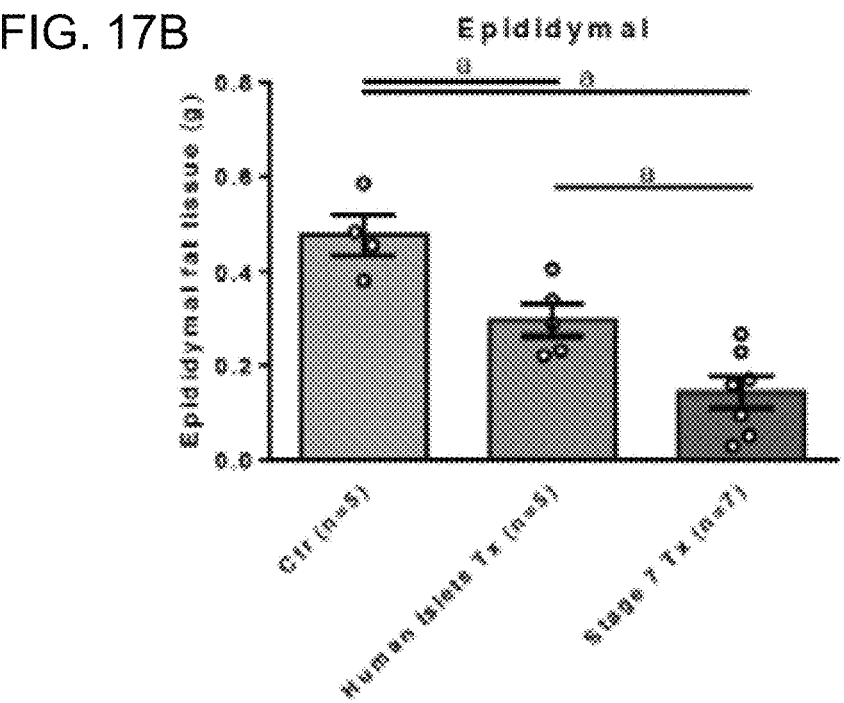
Figure 17C:
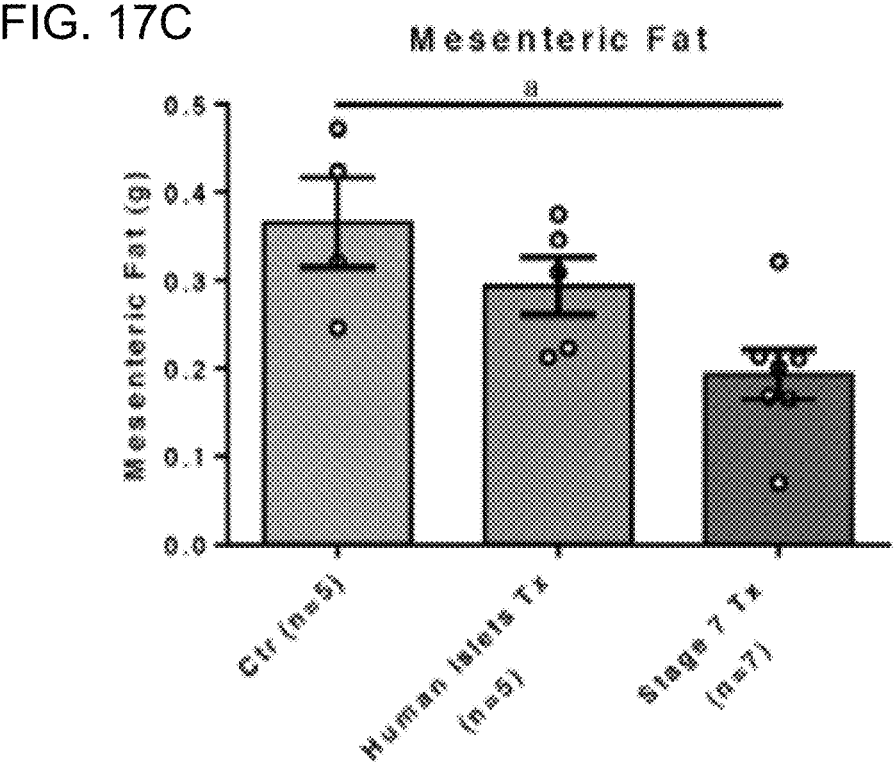
Figure 17D:
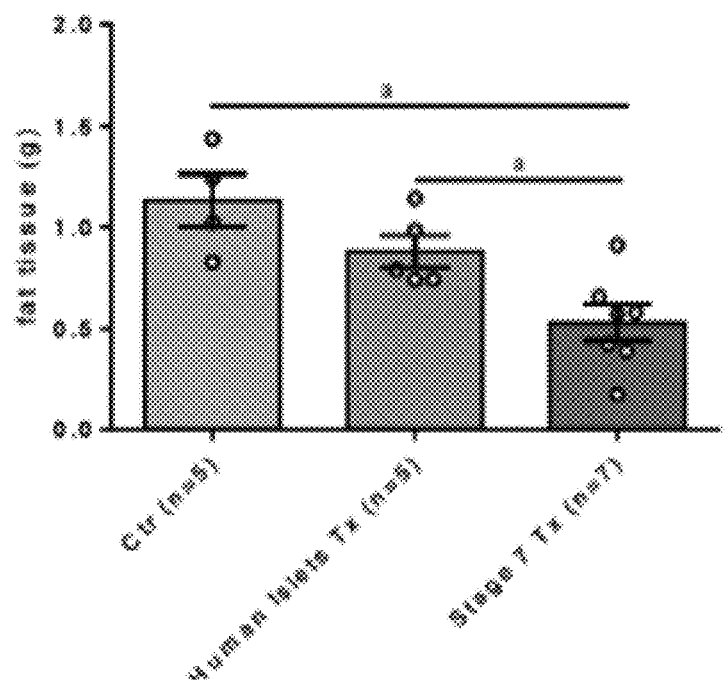

Similarly, FIGS. 17A-D show reduced fat weight when comparing Stage 7 transplanted cells with either Human islet transplants or control cells in perirenal tissues (FIG. 17C), epididymal tissues (FIG. 17D), mesenteric fat (FIG. 17E) and in all fat pads (FIG. 17F), which were collected at sacrifice. (Note, for human islet n=5, which includes 4 mice that got STZ and one that did not get STZ). Accordingly, transplantation of Stage 7 human pancreatic progenitor cells appear to be more effective at reducing fat than human islet cells in diabetic model mice. In FIG. 17A, there is shown data for both left and right kidneys and it is noted that the peri-renal fat around the left kidney as compared to the right kidney (except for the control the "right" kidney is labeled either "Human Islets Tx" or "Stage 7 Tx"), and when the data is combined for the right and left kidney the bar on the graph is designated "both". In mice that got either islets or stage 7 cells, cells were transplanted into the right kidney, which sees greater fat accumulation than the left kidney, except in the controls. It is likely that we see more fat accumulation around the kidney into which the cells were transplanted, because we speculate that there is local accumulation of insulin, and insulin is adipogenic.

Therefore, transplant of human islets and human Stage 7 cells may produce weight loss. There are some reports of patients with T1D who receive an islet transplant and subsequently lose weight. This has been assumed to be due to the surgical procedure, immunosuppressive drugs, and/or life style changes. However, perhaps the weight loss is due to the islet cells themselves. It has been found that both human islets and differentiated human stem cells produce the peptide Glucagon-like peptide-1 (GLP-1). GLP-1 is an incretin (i.e. a metabolic hormone) that is known to increase the amount of insulin released by pancreatic beta-cells and may subsequently decrease blood glucose. Furthermore, when injected into animals or humans, GLP-1 can produce weight loss and is now used as a drug in patients with T2D. In these patients weight loss has been reported.

Also, when cells are transplanted in combination with the drug Sitagliptin, the most weight loss was observed (see FIG. 5D). Sitagliptin is a known inhibitor of the enzyme dipeptidyl peptidase-4 (DPP-4), which degrades and inactivates GLP-1. Accordingly, it is possible that one mechanism by which the cells reduce weight gain is by producing GLP-1, and this affect is enhanced by stabilizing the GLP-1 with Sitagliptin.

Example 9: Comparison of Stage 7 (S7) Macro-Encapsulated Cell Transplants in Mice At the moment, encapsulation is proposed to be the best way to avoid an immune response in a clinically setting. However, this has yet to be determined as we are unable to experimentally confirm this in an animal model (the macro-encapsulation device we used, made by TheraCyte, does not prevent xenograft rejection). Early results released from ViaCyte suggest that their similar devices may be working in a patient. Of note, while the stage 4 progenitor cells have done well in these devices, it was uncertain whether more mature differentiated cells (i.e. Stages >4) would survive. Indeed studies with fetal versus mature islets have shown fetal islets (akin to Stage 4 cells) do survive, mature and function within TheraCyte devices while adult islets have poor survival (Lee, S H. et al. 2009). Therefore, one may have predicted that the more islet-like cells from advanced differentiation protocols would also not work well. However, recently we have obtained data (see FIGS. 19 and 20) that demonstrate that Stage 7 cells can indeed survive and function within these macro-encapsulation devices.

While we have tested macro-encapsulation, others are investigating micro-encapsulation as an alternative strategy (see for example, Vegas, A J. et al. 2016). Aside from encapsulation, inducing immune tolerance has also been explored as a strategy to avoid an immune response in vivo (Szot, G L. et al. 2015). It remains to be determined if this is a clinically relevant approach.

Figure 18B:
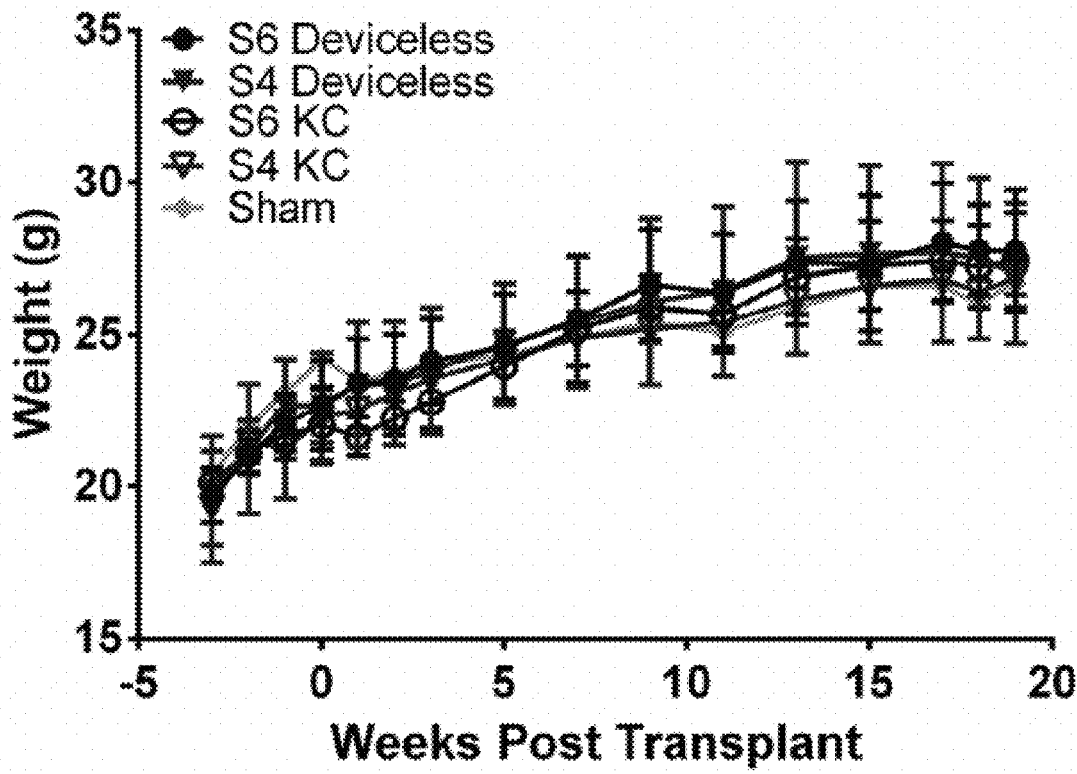
Figure 18C:
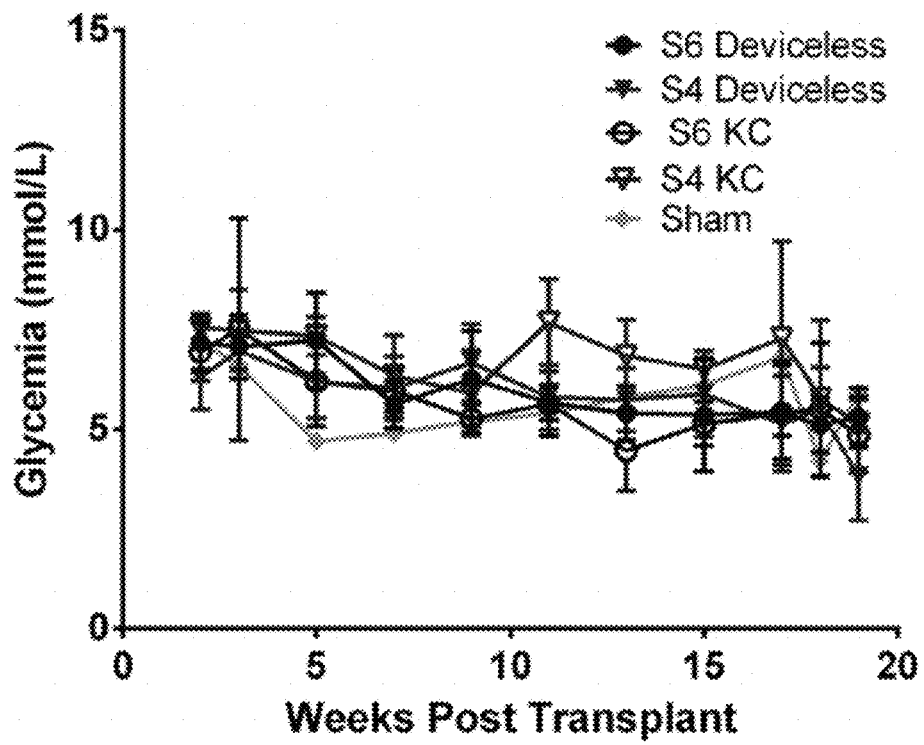

Weekly fasting blood glucose and body weight monitoring showed that there were no differences in between mean weight or glycemia of animals in any groups (see FIGS. 18B and 18C). However, when comparing Stage 4 and Stage 6 cell transplants in deviceless and kidney capsule (KC) implanted mice C-peptide levels were significantly higher in S6 KC cells within 10 weeks of the transplant (see FIG. 18A).

Figure 19:
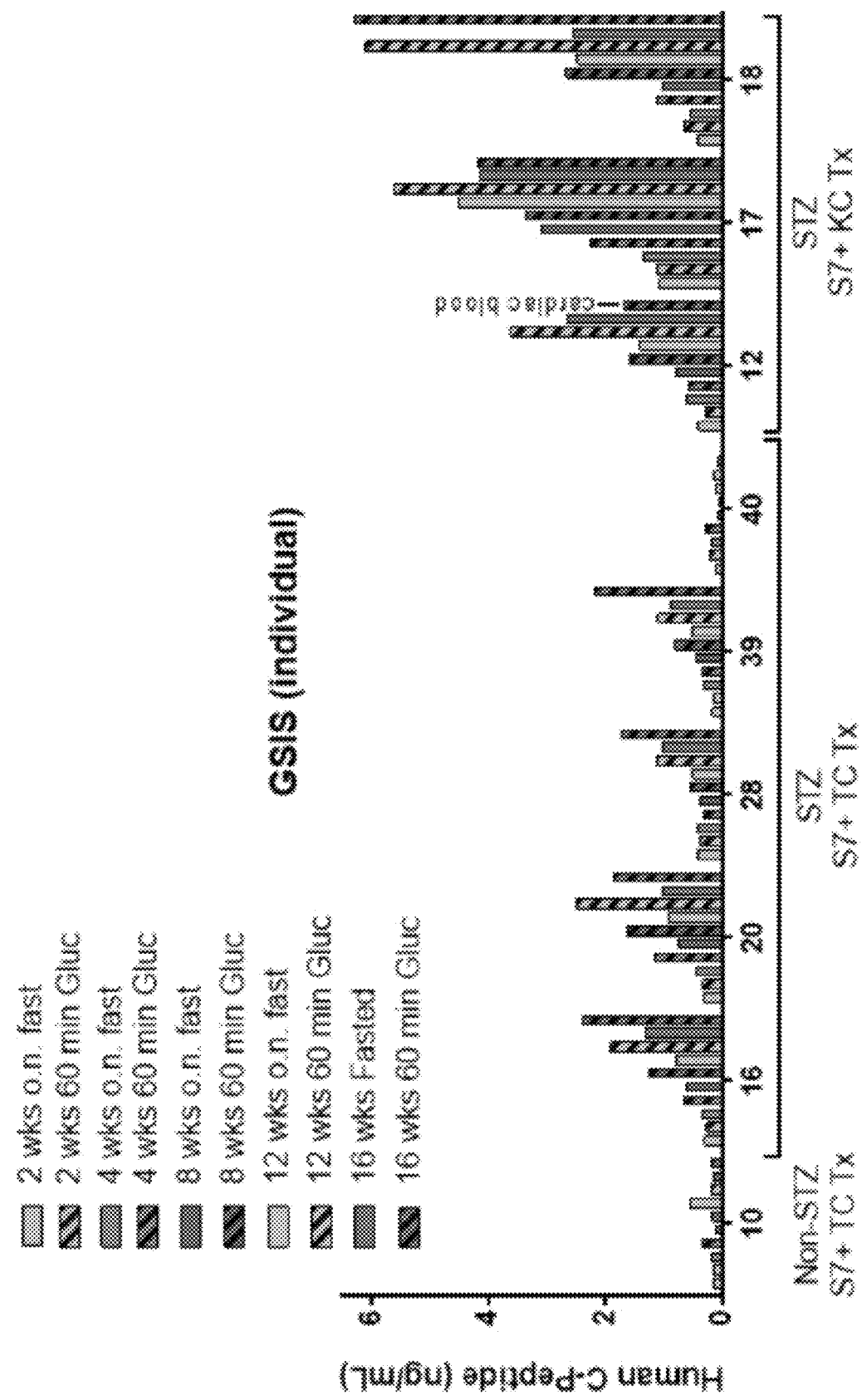
FIG. 19 shows a graph tracking of human C-peptide in individual mice (animals numbers on X-axis) at the indicating time points post transplant of Stage 7 cells within TheraCyte devices, transplanted subcutaneously (S7+Tc Tx), or without encapsulation and transplanted beneath the kidney capsule (KC), with transplants unsuccessful in animal numbers 10 and 40.
Figure 20:
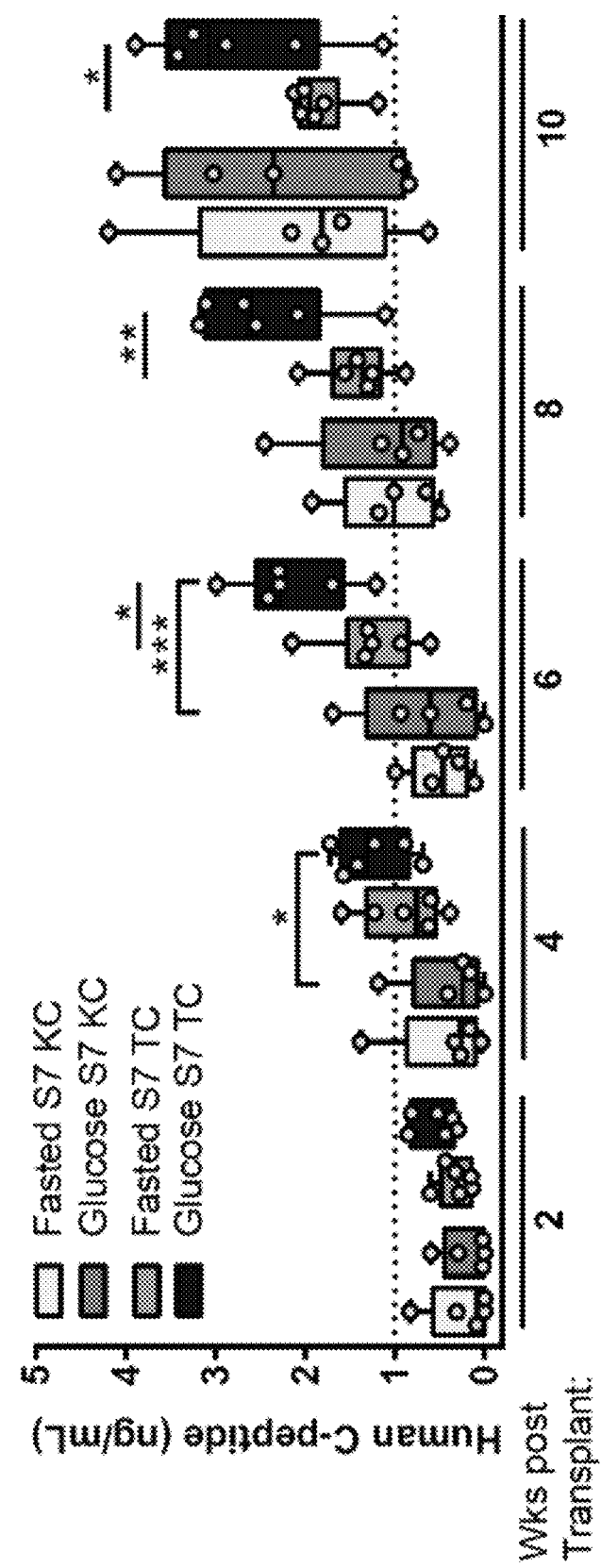
FIG. 20 shows graph tracking of human C-peptide in mice at the indicating time points post transplant of Stage 7 cells within TheraCyte devices (TC), transplanted subcutaneously, or without encapsulation and transplanted beneath the kidney capsule (KC).

The graft retrieval after transplant followed by immunohistochemical analysis showed the TheraCyte devices used in FIGS. 19 and 20 contained predominantly what appeared to be endocrine cells (Synaptophysin positive). The cells appeared to be functioning well with good glucose responsive C-peptide production.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to an embodiment of the present invention. The invention includes all embodiments and variations substantially as hereinbefore described and with reference to the examples and drawings.

REFERENCES

Agulnick, A. D. et al. "Insulin-Producing Endocrine Cells Differentiated In Vitro From Human Embryonic Stem Cells Function in Macroencapsulation Devices In Vivo" Stem Cells Trans Med (2015) 2015 4(10):1214-1222.

Agulnick, A. D. et al. International Application WO/2014/160413.

Bruin, JE, Rezania A, Xu J, Narayan K, Fox J K, O'Neil J J, Kieffer T J. "Maturation and function of human embryonic stem cell-derived pancreatic progenitors in macro-encapsulation devices following transplant into mice." Diabetologia (2013) 56(9)1987-98.

Bruin, JE. Erener S. Vela J. et al. "Characterization of polyhormonal insulin-producing cells derived in vitro from human embryonic stem cells." Stem Cell Res. (2014) 12(1):194-208.

Bruin, JE. Saber N. Braun N. et al. "Treating diet-induced diabetes and obesity with human embryonic stem cell-derived pancreatic progenitor cells and antidiabetic drugs." Stem Cell Reports (2015) 4(4)605-620.

D'Amour, K A. et al. "Efficient differentiation of human embryonic stem cells to definitive endoderm" Nature Biotechnology (2005) 23:1534-1541.

D'Amour, K A. et al. "Production of pancreatic hormone-expressing endocrine cells from human embryonic stem cells." Nature Biotechnology (2006) 24(11):1392-401. Epub 2006 Oct. 19.

Fung, R. and Fryer B. U.S. Patent Application Publication No. 2011/0104805.

Gafni, O. et al. "Derivation of novel human ground state naive pluripotent stem cells." Nature (2013) 504:282-286.

Heit, J J., et al. "Calcineurin/NFAT signalling regulates pancreatic beta cell growth and function." Nature (2006) 443(7109): 345-349.

Kahraman, S. et al. "Maternal insulin resistance and transient hyperglycemia impact the metabolic and endocrine phenotypes of offspring." AJP: Endocrinology and Metabolism (2014) 307(10): E906.

Kelly, O G. et al. "Cell-surface markers for the isolation of pancreatic cell types derived from human embryonic stem cells." Nature Biotechnology (2011) 29(8):750-756.

Kihm, A. et al. United States Patent Publication No. 2005/0058631.

Kroon, E. et al. Pancreatic endoderm derived from human embryonic stem cells generates glucose-responsive insulin-secreting cell in vivo. Nature Biotechnology (2008) 26:443-452.

Jonas, J C. et al. "Chronic hyperglycemia triggers loss of pancreatic beta cell differentiation in an animal model of diabetes." J Biol Chem. (1999) 274(20):14112-21.

Lee, S H. et al. "Human beta-cell precursors mature into functional insulin-producing cells in an immunoisolation device: implications for diabetes cell therapies." Transplantation (2009) 87(7):983-91.

Li, W. et al. "Generation of rat and human induced pluripotent stem cells by combining genetic reprogramming and chemical inhibitors." Cell Stem Cell (2009) 4(1): 16-19.

Loh, Y H. et al. "Genomic approaches to deconstruct pluripotency." Annu Rev Genomics Hum Genet (2011) 12:165-185.

Maherali, N. et al. "Directly reprogrammed fibroblasts show global epigenetic remodeling and widespread tissue contribution." Cell Stem Cell (2007) 1(1): 55-70.

Mistry, S. et al. U.S. Pat. No. 7,510,873.

Nakagawa, M. et al. "Generation of induced pluripotent stem cells without Myc from mouse and human fibroblasts." Nature Biotechnol (2008) 26(1): 101-106.

Ng, M. et al., "Global, Regional & National Prevalence of Overweight and Obesity in Children and Adults During 1980-2013: A Systematic Analysis for the Global Burden of Disease Study 2013" Lancet (2014) 384(9945)766-781.

Nir, T., D. A. Melton and Y. Dor "Recovery from diabetes in mice by beta cell regeneration." J. Clin Invest (2007) 117(9)2553-2561.

O'Dowd, J F. and Stocker, CJ. "Endocrine pancreatic development: impact of obesity and diet" Front Physiol. (2013) 4:170.

Pagliuca, F W. et al. "Generation of functional human pancreatic cells in vitro". Cell 2014 159(2)428-39.

Pepper, A R. et al. "A prevascularized subcutaneous device-less site for islet and cellular transplantation" Nature Biotechnology (2015) 33(5):518-523.

Rezania, A. Riedel M J. Wideman R D. et al. "Production of functional glucagon-secreting-cells from human embryonic stem cells." Diabetes (2011) 60(1):239-247.

Rezania, A. Bruin J E. Riedel M J. et al. "Maturation of human embryonic stem cell-derived pancreatic progenitors into functional islets capable of treating pre-existing diabetes in mice." Diabetes (2012) 61(8):2016-29.

Rezania, A. Bruin J E. Xu J. et al. "Enrichment of human embryonic stem cell-derived NKX6.1-expressing pancreatic progenitor cells accelerates the maturation of insulin-secreting cells in vivo." Stem Cells (2013) 31(11):2432-2442.

Rezania, A., Bruin, J. E., Arora, P. et al. "Reversal of diabetes with insulin-producing cells derived in vitro from human pluripotent stem cells." Nat Biotechnol (2014) 32(11):1121-1133.

Rezania, A. United States Patent Publication US20090170198.

Russ H A, et al. "Controlled induction of human pancreatic progenitors produces functional beta-like cells in vitro." EMBO J. (2015) 34(13)1759-72.

Schulz, T. et al. "A Scalable System for Production of Functional Pancreatic Progenitors from Human Embryonic Stem Cells". Public Library of Science One (2012) 7(5):e37004.

Stadtfeld, M. et al. "Defining molecular cornerstones during fibroblast to iPS cell reprogramming in mouse." Cell Stem Cell (2008) 2(3): 230-240.

Szot, G L. et al. "Tolerance induction and reversal of diabetes in mice transplanted with human embryonic stem cell-derived pancreatic endoderm" Cell Stem Cell (2015) 16(2):148-157.

Takahashi, K. et al. "Induction of pluripotent stem cells from adult human fibroblasts by defined factors." Cell (2007) 131: 861-872.

Takahashi, K. and Yamanaka, S. "Induction of pluripotent stem cells from mouse embryonic and adult fibroblast cultures by defined factors." Cell (2006) 126(4): 663-676.

Tang, Q. and Desai, TA. "Approaching a cure for type 1 diabetes" Nature Medicine (2016) 22(3):236-237.

Thomson, J A. et al. "Isolation of a primate embryonic stem cell line." Proc Natl Acad Sci U.S.A. (1995) 92(17):7844-7848.

Thomson, J A. and Marshall, VS. "Primate embryonic stem cells." Curr Top Dev Biol (1998) 38:133-165.

Thomson, J A. et al. "Embryonic stem cell lines derived from human blastocysts." Science (1998) 282(5391): 1145-1147.

Thomson, JA. U.S. Pat. No. 5,843,780.

Thomson, JA. and Xu, J. U.S. Patent App. Pub. No. 2007/0122903.

Vegas, A J. et al. "Long-term glycemic control using polymer-encapsulated human stem cell-derived beta cells in immune-competent mice." Nature Medicine (2016) 22:306-311.

Ware, C B. et al. "Derivation of naive human embryonic stem cells." Proc Natl Acad Sci USA. (2014) 111: 4484-4489.

Xu, J. United States Patent Publication US20120039955.

What is claimed is:

1. A method for treating obesity, glucose intolerance or insulin resistance in a subject with type 2 diabetes (T2D), the method comprising: implanting a population of pancreatic endocrine progenitor cells into the subject, wherein the pancreatic endocrine progenitor cells mature in vivo to produce a population comprising pancreatic endocrine cells.

2. The method of claim 1, the method further comprising administering a therapeutically effective amount of one or more small molecule anti-diabetic drugs to the subject.

3. The method of claim 1, wherein the pancreatic endocrine progenitor cells mature in vivo to produce a population comprising at least 2% pancreatic endocrine cells.

4. The method of claim 2, wherein the one or more small molecule anti-diabetic drugs are selected from the following: meglitinides; sulfonylureas; dipeptidyl-peptidase 4 (DPP-4) inhibitors; biguanides; thiazolidinediones; alpha-glucosidase inhibitors; sodium-glucose transporter 2 (SGLT-2) inhibitors; and bile acid sequestrants.

5. The method of claim 2, wherein the small molecule anti-diabetic drug is selected from the group consisting of: repaglinide; nateglinide; glipizide; glimepiride; glyburide; saxagliptin; sitagliptin; linagliptin; metformin; rosiglitazone; pioglitazone; acarbose; miglitol; canagliflozin; dapagliflozin; empagliflozin; and colsevelam.

6. The method of claim 2, wherein the anti-diabetic drug is selected from the group consisting of: sitagliptin; metformin; and rosiglitazone.

7. The method of claim 1, wherein the method comprises treating glucose intolerance in the subject.

8. The method of claim 1, wherein the method comprises treating insulin resistance in the subject.

9. A method for treating obesity, glucose intolerance or insulin resistance in a subject with type 2 diabetes (T2D), the method comprising:
implanting a population of pancreatic endocrine progenitor cells into the subject, wherein the pancreatic endocrine progenitor cells mature in vivo to produce a population comprising pancreatic endocrine cells; and
administering to the subject a therapeutically effective amount of one or more of sitagliptin; metformin; and rosiglitazone.

10. The method of claim 9, wherein the pancreatic endocrine progenitor cells mature in vivo to produce a population comprising at least 2% pancreatic endocrine cells.

11. The method of claim 9, wherein the method comprises treating obesity in the subject.

12. The method of claim 9, wherein the method comprises treating glucose intolerance in the subject.

13. The method of claim 9, wherein the method comprises treating insulin resistance in the subject.

14. A method for treating obesity, glucose intolerance or insulin resistance in a subject with type 2 diabetes (T2D) to whom a therapeutically effective amount of an anti-diabetic drug has been administered, the method comprising:

implanting a population of pancreatic endocrine progenitor cells into the subject wherein the pancreatic endocrine progenitor cells mature in vivo to produce a population comprising pancreatic endocrine cells;

wherein the anti-diabetic drug is sitagliptin, metformin, or rosiglitazone.

15. The method of claim 14, wherein the pancreatic endocrine progenitor cells mature in vivo to produce a population comprising at least 2% pancreatic endocrine cells.

16. The method of claim 14, wherein the method comprises treating obesity in the subject.

17. The method of claim 14, wherein the method comprises treating glucose intolerance in the subject.

18. The method of claim 14, wherein the method comprises treating insulin resistance in the subject.

* * * * *

UNITED STATES PATENT AND TRADEMARK OFFICE
CERTIFICATE OF CORRECTION

PATENT NO. : 10,772,917 B2
APPLICATION NO. : 15/556907
DATED : September 15, 2020
INVENTOR(S) : Timothy J. Kieffer et al.

It is certified that error appears in the above-identified patent and that said Letters Patent is hereby corrected as shown below:

In the Claims

At Column 42, Line 18, Claim 1:
Delete "obesity," and replace with --A method for treating glucose intolerance or insulin resistance in a subject with type 2 diabetes (T2D), the method comprising: implanting a population of pancreatic endocrine progenitor cells into the subject, wherein the pancreatic endocrine progenitor cells mature in vivo to produce a population comprising pancreatic endocrine cells.--

Signed and Sealed this
Seventeenth Day of November, 2020

Andrei Iancu
*Director of the United States Patent and Trademark Office*